US011367534B2

United States Patent
Mc Namara et al.

(10) Patent No.: US 11,367,534 B2
(45) Date of Patent: Jun. 21, 2022

(54) SYSTEMS AND METHODS FOR CONTAGIOUS DISEASE RISK MANAGEMENT

(71) Applicant: Johnson Controls Tyco IP Holdings LLP, Milwaukee, WI (US)

(72) Inventors: Edward Gerard Mc Namara, County Limerick (IE); James Callanan, Cork (IE); Tim Murphy, Maryborough Hill (IE); Robert Artur Dubisz, County Cork (IE); Matthew Breed Myung-Sun Scott, Cork (IE); Amit Kumar, Cork (IE); Sarah O'Connell, Cork (IE); Rachel D. M. Ellerman, Shorewood, WI (US); Vikas Sharma, New Delhi (IN); Sourabh Taranath Joshi, Maharashtra (IN); Akshay Chavan, Maharashtra (IN)

(73) Assignee: Johnson Controls Tyco IP Holdings LLP, Milwaukee, WI (US)

( * ) Notice: Subject to any disclaimer, the term of this patent is extended or adjusted under 35 U.S.C. 154(b) by 0 days.

(21) Appl. No.: 17/220,795

(22) Filed: Apr. 1, 2021

(65) Prior Publication Data

US 2021/0313075 A1 Oct. 7, 2021

Related U.S. Application Data

(60) Provisional application No. 63/004,269, filed on Apr. 2, 2020.

(30) Foreign Application Priority Data

Jul. 31, 2020 (IN) .............................. 202011032928

(51) Int. Cl.
  *G16H 70/20* (2018.01)
  *G08B 21/02* (2006.01)
  *G16H 50/30* (2018.01)

(52) U.S. Cl.
  CPC ............. *G16H 70/20* (2018.01); *G08B 21/02* (2013.01); *G16H 50/30* (2018.01)

(58) Field of Classification Search
  CPC ......... G16H 70/20; G16H 50/30; G08B 21/02
  See application file for complete search history.

(56) References Cited

U.S. PATENT DOCUMENTS

| 6,968,179 | B1 | 11/2005 | Devries |
| 7,099,895 | B2 | 8/2006 | Dempsey |

(Continued)

FOREIGN PATENT DOCUMENTS

| JP | 2010-128976 A | 6/2010 |
| KR | 20200047457 A | 5/2020 |
| WO | WO-2021/258116 A1 | 12/2021 |

OTHER PUBLICATIONS

Condeco Group, "Meeting Room & Desk Booking Systems," URL: www.condecosoftware.com/, Retrieved from Internet Sep. 9, 2020, 10 Pages.

(Continued)

*Primary Examiner* — Hongmin Fan
(74) *Attorney, Agent, or Firm* — Foley & Lardner LLP

(57) ABSTRACT

A building system of a building, the building system including one or more memory devices configured to store instructions thereon that, when executed by one or more processors, cause the one or more processors to receive occupancy data of occupants from an occupant tracking system, the occupancy data indicating locations of the occupants within a building space of the building. The instructions cause the one or more processors to determine, based on the occupancy data, whether one or more occupants of the occupants (Continued)

have violated a social distancing policy that reduces a spread of an infectious disease within the building based on the locations of at least two of the occupants, the social distancing policy based on one or more characteristics of the building space and perform one or more operations to improve compliance with the social distancing policy within the building.

24 Claims, 33 Drawing Sheets

(56) References Cited

U.S. PATENT DOCUMENTS

| | | | |
|---|---|---|---|
| 7,394,370 | B2 | 7/2008 | Chan |
| 7,598,854 | B2 | 10/2009 | Wong |
| 7,705,723 | B2 | 4/2010 | Kahn et al. |
| 7,817,046 | B2 | 10/2010 | Coveley et al. |
| 7,941,096 | B2 | 5/2011 | Perkins et al. |
| 7,993,266 | B2 | 8/2011 | Colston et al. |
| 8,049,614 | B2 | 11/2011 | Kahn et al. |
| 8,405,503 | B2 | 3/2013 | Wong |
| 8,867,993 | B1 | 10/2014 | Perkins et al. |
| 9,075,909 | B2 | 7/2015 | Almogy et al. |
| 9,741,233 | B2 | 8/2017 | Laufer et al. |
| 10,068,116 | B2 | 9/2018 | Good et al. |
| 10,198,779 | B2 | 2/2019 | Pittman et al. |
| 10,251,610 | B2 | 4/2019 | Parthasarathy et al. |
| 10,257,642 | B2 | 4/2019 | Pittman et al. |
| 10,803,993 | B2 | 10/2020 | Huang |
| 2006/0036619 | A1 | 2/2006 | Fuerst et al. |
| 2006/0085483 | A1 | 4/2006 | Mooney et al. |
| 2012/0056720 | A1* | 3/2012 | Barvick ............. G06K 7/10009 340/10.1 |
| 2014/0049376 | A1* | 2/2014 | Ng ........................ A47B 91/00 340/10.1 |
| 2016/0005300 | A1 | 1/2016 | Laufer et al. |
| 2017/0123440 | A1 | 5/2017 | Mangsuli et al. |
| 2017/0124850 | A1* | 5/2017 | Kramer ............. G08B 21/0277 |
| 2017/0206334 | A1 | 7/2017 | Huang |
| 2018/0052970 | A1 | 2/2018 | Boss et al. |
| 2018/0104162 | A1 | 4/2018 | Park |
| 2018/0204162 | A1 | 7/2018 | Endel et al. |
| 2019/0228348 | A1 | 7/2019 | O'Keefe-Sally et al. |
| 2020/0176124 | A1* | 6/2020 | Chatterjea ............. G16H 50/80 |
| 2020/0176125 | A1 | 6/2020 | Chatterjea et al. |
| 2021/0193309 | A1 | 6/2021 | Boisvert et al. |
| 2021/0313075 | A1 | 10/2021 | Mc Namara et al. |
| 2021/0390807 | A1 | 12/2021 | Chaurasia et al. |
| 2021/0390812 | A1 | 12/2021 | Chaurasia et al. |
| 2021/0391089 | A1 | 12/2021 | Eswara et al. |
| 2021/0398659 | A1 | 12/2021 | Sharma et al. |
| 2021/0398690 | A1 | 12/2021 | Gibson et al. |
| 2021/0398691 | A1 | 12/2021 | Dhamija et al. |
| 2022/0060856 | A1 | 2/2022 | Wellig et al. |

OTHER PUBLICATIONS

Condeco, "Back to the new normal," 2020, 12 Pages.
Condeco, "How tomorrow will work: returning to the office after COVID-19 Guide," URL: https://www.condecosoftware.com/modern-workplace/asset/ebooks/returning-to-the-office-after-covid-19-guide/, Retrieved from Internet Dec. 14, 2021, 8 Pages.
Condeco, "Making your employees safety a priority when coming into the office," URL: https://www.condecosoftware.com/blog/employee-office-safety/, Sep. 27, 2020, 5 Pages.
Condeco, "Office layouts for the post COVID-19 workplace," URL: https://www.condecosoftware.com/blog/office-design-post-covid-19-workplace/, Jun. 25, 2020, 6 Pages.
Condeco, "Putting your employees health and well-being first—post-pandemic mental health tips," URL: https://www.condecosoftware.com/blog/employee-health-well-being-post-pandemic/, Sep. 17, 2020, 5 Pages.
Condeco, "Rethinking and reshaping your workspace," URL: https://www.condecosoftware.com/blog/rethinking-reshaping-workspace/, May 27, 2021, 5 Pages.
Condeco, "Returning to the office after COVID-19." URL: https://www.condecosoftware.com/modern-workplace/wp-content/uploads/sites/10/2020/05/TL-SOL-226-EN_Returning-to-the-office-after-COVID-19.pdf, Retrieved from Internet Dec. 14, 2021, 23 Pages.
Condeco, "Returning to the Office Post COVID-19: and why businesses can't afford to get this wrong.," URL:https://www.condecosoftware.com/blog/returning-to-the-office-post-covid-19/, May 6, 2020, 5 Pages.
Condeco, "Safe social distancing measures on your return to the office," URL: https://www.condecosoftware.com/blog/safe-office-social-distancing-measures/, May 26, 2020, 6 Pages.
Condeco, "The future of the workplace and effective workspace scheduling," URL: https://www.condecosoftware.com/blog/future-workspace-scheduling/, Oct. 24, 2020, 5 Pages.
Condeco, "The post-COVID workplace." URL: https://www.condecosoftware.com/modern-workplace/asset/ebooks/post-covid-workplace/, Retrieved from Internet Dec. 14, 2021, 7 Pages.
Condeco, "The work-related COVID-19 questions we're all asking," URL: https://www.condecosoftware.com/blog/work-related-covid-questions/, Oct. 29, 2020, 5 Pages.
Condeco, "What's next? Your work life after COVID-19," URL: https://www.condecosoftware.com/blog/work-life-after-covid/, Jul. 27, 2021, 5 Pages.
Condeco, "Workplace cleanliness: The facts for a post-isolation working environment," URL: https://www.condecosoftware.com/blog/workplace-cleanliness-facts/, Apr. 23, 2020, 6 Pages.
Officespace Software, "OfficeSpace Software: The Smarter Facility Management Software," URL: www.officespacesoftware.com/, Retrieved from Internet Sep. 9, 2020, 5 Pages.

* cited by examiner

FIG. 17

SOCIAL DISTANCING - INDIVIDUALS

| Badge | On Site Time | Social Distancing Violation Time | Social Distancing Violation to Onsite Time Ratio | Unique Badges with Social Distancing Violations | Unique Areas with Social Distancing Violations |
|---|---|---|---|---|---|
| SW Engineer_031 | 79:55 | 267:30 | 3.3 | 57 | 13 |
| SW Engineer_015 | 79:27 | 240:08 | 3 | 52 | 6 |
| HR_003 | 71:36 | 147:01 | 2.1 | 54 | 7 |
| SW Engineer_029 | 69:40 | 216:36 | 3.1 | 62 | 13 |
| SW Engineer_027 | 68:52 | 219:46 | 3.2 | 59 | 7 |
| SW Engineer_001 | 65:28 | 319:59 | 4.9 | 76 | 45 |
| HW Engineer_004 | 65:07 | 85:16 | 1.3 | 43 | 14 |
| HW Engineer_024 | 64:58 | 102:49 | 1.6 | 65 | 12 |
| SW Engineer_030 | 63:40 | 170:17 | 2.7 | 62 | 18 |
| HW Engineer_022 | 63:35 | 104:30 | 1.6 | 48 | 12 |
| HW Engineer_032 | 62:47 | 132:09 | 2.1 | 46 | 11 |
| HW Engineer_027 | 61:16 | 114:39 | 1.9 | 52 | 9 |
| HW Engineer_017 | 61:14 | 105:39 | 1.7 | 50 | 10 |
| HW Engineer_025 | 60:25 | 100:51 | 1.7 | 56 | 12 |
| SW Engineer_006 | 57:26 | 220:49 | 3.8 | 72 | 13 |
| SW Engineer_009 | 56:20 | 189:45 | 3.4 | 57 | 8 |
| HW Engineer_019 | 55:59 | 82:11 | 1.5 | 52 | 12 |
| HW Engineer_030 | 55:58 | 51:52 | 0.9 | 21 | 12 |
| Facilities_035 | 55:17 | 326:19 | 5.9 | 66 | 2 |
| SW Engineer_004 | 54:57 | 178:41 | 3.3 | 60 | 14 |
| HR_010 | 54:42 | 265:25 | 4.9 | 62 | 12 |
| SW Engineer_010 | 54:14 | 230:44 | 4.3 | 56 | 12 |
| SW Engineer_039 | 53:29 | 200:53 | 3.8 | 52 | 13 |
| SW Engineer_022 | 52:29 | 284:11 | 5.4 | 44 | 3 |
| Facilities_047 | 51:38 | 333:46 | 6.5 | 62 | 2 |
| HW Engineer_023 | 51:13 | 40:04 | 0.8 | 23 | 11 |

From 2020-02-24 09:00

To 2020-03-06 17:00

Minimum Overlap Time 15 mins (Infected Person)

EXPORT DATA

| | Location Service | Bluetooth Phone App | Under Desk Sensors | Overhead People Counters | Access Control Systems | CCTV Systems |
|---|---|---|---|---|---|---|
| Contact Tracing | ● | ◐ | ○ | ○ | ○ | ◐ |
| Social Distance Monitoring | ● | ◐ | ◐ | ◐ | ◐ | ◐ |
| Building Overview Trend Reports | ● | ○ | ○ | ○ | ◐ | ○ |
| Lone Worker Monitoring | ● | ○ | ○ | ○ | ○ | ◐ |
| Lone Worker Duress Support | ● | ◐ | ○ | ○ | ◐ | ◐ |
| Outdoor Use | ○ | ● | ◐ | ◐ | ○ | ◐ |
| Ease & Speed of Development | ● | ◐ | ◐ | ○ | ○ | ◐ |
| Wireless Infrastructure | ● | ● | ● | ○ | ○ | ○ |
| Rich Additional Building Use Cases | ● | ◐ | ◐ | ○ | ◐ | ◐ |

FIG. 23

SYSTEMS AND METHODS FOR CONTAGIOUS DISEASE RISK MANAGEMENT

CROSS-REFERENCE TO RELATED PATENT APPLICATIONS

This application claims the benefit of and priority to U.S. Provisional Patent Application No. 63/004,269 filed Apr. 2, 2020 and Indian Provisional Patent Application No. 202011032928 filed Jul. 31, 2020, the entireties of which are incorporated by reference herein.

BACKGROUND

This application relates to systems and methods for building management. More particularly, this application relates to systems and methods for operating buildings with respect to a contagious diseases. An infectious disease such as a virus, a bacteria, etc. can be spread through person to person interaction, in some cases. An infectious disease can spread indoors between occupants of a building, in some situations. This can result in occupants needing to stay out of a building in order to reduce the spread of the infectious disease. Therefore, systems and methods for a building that enable occupants to remain within the building even though an infectious disease is present in a population is desired.

SUMMARY

One implementation of the present disclosure is a building system of a building, the building system including one or more memory devices configured to store instructions thereon that, when executed by one or more processors, cause the one or more processors to receive occupancy data of occupants from an occupant tracking system, the occupancy data indicating locations of the occupants within a building space of the building, determine, based on the occupancy data, whether one or more occupants of the occupants have violated a social distancing policy that reduces a spread of an infectious disease within the building based on the locations of at least two of the occupants, the social distancing policy based on one or more characteristics of the building space, and perform one or more operations to improve compliance with the social distancing policy within the building in response to a determination that the one or more occupants have violated the social distancing policy.

In some embodiments, the instructions cause the one or more processors to determine that a first occupant of the two or more occupants is at a first location within a particular distance from a second location of a second occupant of the two or more occupants for at least a particular length of time In some embodiments, the one or more operations include generating a notification that includes an indication of the social distancing policy being violated and sending the notification to user devices associated with the one or more occupants.

In some embodiments, the one or more occupants include a first occupant and a second occupant. In some embodiments, the instructions cause the one or more processors to record an encounter between the first occupant and the second occupant with encounters between occupants of the occupants, receive an indication of one or more infected occupants of the occupants that are infected with the infectious disease, and analyze the encounters to identify one or more potentially infected occupants that have come into contact with the one or more infected occupants.

In some embodiments, the instructions cause the one or more processors to generate a space score for one space of spaces of the building based on one or more parameters, the one or more parameters indicating a number of social distancing violations that have occurred within the one space and cause a user device to display the space score for the one space.

In some embodiments, the instructions perform the one or more operations to improve compliance with the social distancing policy by adding a social distancing alert to a list of active social distancing alerts in the building and causing a building monitoring interface to display the list of active social distancing alerts.

In some embodiments, the one or more occupants include a first occupant and a second occupant. In some embodiments, the instructions cause the one or more processors to record a social distancing violation between the first occupant and the second occupant with social distancing violations between the occupants, generate one or more trends that trend the social distancing violations over time, and cause a user interface to include the one or more trends.

In some embodiments, the instructions cause the one or more processors to determine a number of occupants in each space of spaces of the building based on the occupancy data, determine whether the number of occupants in each space of the spaces is greater than or less than one or more levels, wherein the one or more levels indicate underutilization of a space, normal utilization of a space, or over utilization of a space based on a size of each space of the spaces, and generate a building layout interface that indicates the spaces and whether each space is underutilized, over utilized, or is normally utilization.

In some embodiments, the one or more occupants include a first occupant and a second occupant. In some embodiments, the instructions cause the one or more processors to record a social distancing violation between the first occupant and the second occupant with social distancing violations between the occupants, generate a first graphic element indicating proportions of time that an occupant of the occupants has spent in locations of the building, generate a second graphic element indicating proportions of social distancing violations between the occupant and each the occupants, generate one or more third graphic elements that each indicate a proportion of social distancing violations between the occupant and each of the occupants at one location of the locations of the building, and generate a user interface including the first graphic element, the second graphic element, and the one or more third graphic elements.

In some embodiments, the one or more occupants include a first occupant and a second occupant. In some embodiments, the instructions cause the one or more processors to record a social distancing violation between the first occupant and the second occupant with social distancing violations between the occupants, generate a table based on the social distancing violations and the occupancy data, the table including rows and columns, wherein the rows each indicate an occupant of the occupants and the columns include a first column indicating a total time that each of the occupants have spent within the building, a second column indicating a total amount of time that each of the occupants have spent engaging in the social distancing violations within the building, a third column indicating a ratio between the total time that each of the occupants have spent within the building and the total amount of time that each of the occupants have spent engaging in the social distancing violations within the building, a fourth column including an indication of a number of users that each user has performed a social distancing violation with, and a fifth column indicating a number of spaces that each user has performed a social distancing violation within.

In some embodiments, the instructions cause the one or more processors to receive an indication of infection risk levels associated with areas of the building, receive a starting location of a user within the building and a destination location within the building from a user device, receive a risk tolerance level from the user device, generate, based on the infection risk levels associated with the areas of the building, a route through the building from the starting location to the destination location that avoids one or more high risk areas of the building or passes through the one or more high risk areas of the building based on the risk tolerance level, and cause a user interface to display the route through the building.

In some embodiments, the instructions cause the one or more processors to determine occupancy levels in each space of spaces of the building over a historical time period based on the occupancy data and generate a heat map that that indicates historical utilization of each space of the spaces over the historical time period.

In some embodiments, the instructions cause the one or more processors to schedule building sanitization for the spaces of the building based on the heat map.

In some embodiments, the instructions cause the one or more processors to generate a user score for one occupant of the occupants based on one or more parameters, the one or more parameters indicating a number of social distancing violations associated with the one occupant and cause a user device to display the user score for the one occupant.

In some embodiments, the one or more parameters include at least one of a roster adherence parameter indicating whether the one occupant has followed a roster schedule, social distancing violations parameter indicating the number of social distancing violations associated with the one occupant, a training awareness parameter indicating social distancing training that the one occupant has completed, health parameters indicating health characteristics of the one occupant, a supplies requisition parameter indicating health supplies that the one occupant has acquired, a lone worker duress parameter indicating whether the one occupant has triggered a lone worker response request or an infection level parameter indicating infection levels in a geographic area associated with a residence of the one occupant.

In some embodiments, the building system further includes the occupant tracking system, wherein the occupant tracking system includes transceivers each located within a space of the building, wherein the transceivers are configured to communicate with badges to detect what space of the building the badges are located within and the badges, wherein each badge of the badges is carried by one occupant of the occupants and includes an identifier linked to the one occupant.

In some embodiments, a first badge of the badges is configured to wirelessly send a first identifier of the first badge to a second badge of the badges in response to the first badge being within a particular distance from the second badge, wirelessly receive a second identifier of the second badge from the second badge in response to the first badge being within the particular distance from the second badge, store a contact event in a memory device of the first badge, the contact event including the first identifier and the second identifier, and wirelessly communicate the contact event to a transceiver of the transceivers in response to the first badge being within another particular distance from the transceiver.

In some embodiments, the transceivers include a transceiver that is mounted on a power outlet and is plugged into the power outlet, wherein the transceivers communicate with the badges via a first wireless communication protocol and communicate with the one or more processors via a second wireless communication protocol. In some embodiments, the badges include a battery and a wireless radio, wherein the battery is configured to power the wireless radio.

Another implementation of the present disclosure is a method including receiving, by a processing circuit, occupancy data of occupants from an occupant tracking system, the occupancy data indicating locations of the occupants within a building space of a building and determining, by the processing circuit, based on the occupancy data, whether one or more occupants of the occupants have violated a social distancing policy that reduces a spread of an infectious disease within the building based on the locations of at least two of the occupants, the social distancing policy based on one or more characteristics of the building space. The method further includes performing, by the processing circuit, one or more operations to improve compliance with the social distancing policy within the building in response to a determination that the one or more occupants have violated the social distancing policy.

The method further includes generating, by the processing circuit, a space score for one space of spaces of the building based on one or more parameters, the one or more parameters indicating a number of social distancing violations that have occurred within the one space and causing, by the processing circuit, a user device to display the space score for the one space.

In some embodiments, the method includes performing, by the processing circuit, the one or more operations to improve compliance with the social distancing policy including adding a social distancing alert to a list of active social distancing alerts in the building and causing a building monitoring interface to display the list of active social distancing alerts.

In some embodiments, the one or more occupants include a first occupant and a second occupant. In some embodiments, the method further includes recording a social distancing violation between the first occupant and the second occupant with social distancing violations between the occupants, generating one or more trends that trend the social distancing violations over time, and causing a user interface to include the one or more trends.

In some embodiments, the method includes determining, by the processing circuit, a number of occupants in each space of spaces of the building based on the occupancy data, determining, by the processing circuit, whether the number of occupants in each space of the spaces is greater than or less than one or more levels, wherein the one or more levels indicate underutilization of a space, normal utilization of a space, or over utilization of a space based on a size of each space of the spaces, and generating, by the processing circuit, a building layout interface that indicates the spaces and whether each space is underutilized, over utilized, or is normally utilization.

In some embodiments, the one or more occupants include a first occupant and a second occupant. In some embodiments, the method further includes recording, by the processing circuit, a social distancing violation between the first occupant and the second occupant with distancing violations between the occupants, generating, by the processing circuit, a first graphic element indicating proportions of time that an occupant of the occupants has spent in locations of the building, generating, by the processing circuit, a second graphic element indicating proportions of social distancing violations between the occupant and each the occupants, generating, by the processing circuit, one or more third graphic elements that each indicate a proportion of social distancing violations between the occupant and each of the occupants at one location of the locations of the building, and generating, by the processing circuit, a user interface including the first graphic element, the second graphic element, and the one or more third graphic elements.

Another implementation of the present disclosure is one or more memory devices configured to store instructions thereon that, when executed by one or more processors, cause the one or more processors to receive occupancy data of occupants from an occupant tracking system, the occupancy data indicating locations of the occupants within a building space of a building and determine, based on the occupancy data, whether one or more occupants of the occupants have violated a social distancing policy that reduces a spread of an infectious disease within the building based on the locations of at least two of the occupants, the social distancing policy based on one or more characteristics of the building space. The instructions cause the one or more processors to perform one or more operations to improve compliance with the social distancing policy within the building in response to a determination that the one or more occupants have violated the social distancing policy.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

FIG. 17 is a schematic diagram of a user interface including social distancing alerts, according to an exemplary embodiment.

FIG. 22 is a schematic diagram of a user interface including a table indicating social distancing data for occupants of a building, according to an exemplary embodiment.

FIG. 23 is a table comparing features of various occupant tracing systems, according to an exemplary embodiment.

11 providing a user with their social distancing score, according to an exemplary embodiment.

Figure 29:

FIG. 29 is a schematic diagram of a user interface illustrating key performance indicators for a building HVAC system, according to an exemplary embodiment.

Figure 30:
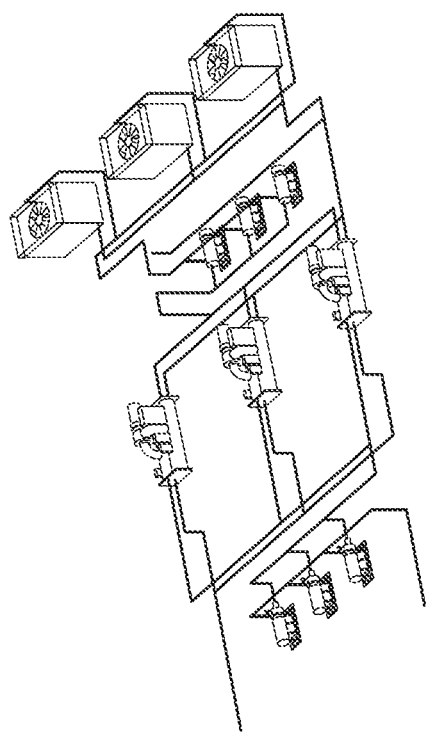

FIG. 30 is a schematic diagram of a user interface indicating the performance of a chiller, according to an exemplary embodiment.

Figure 31:
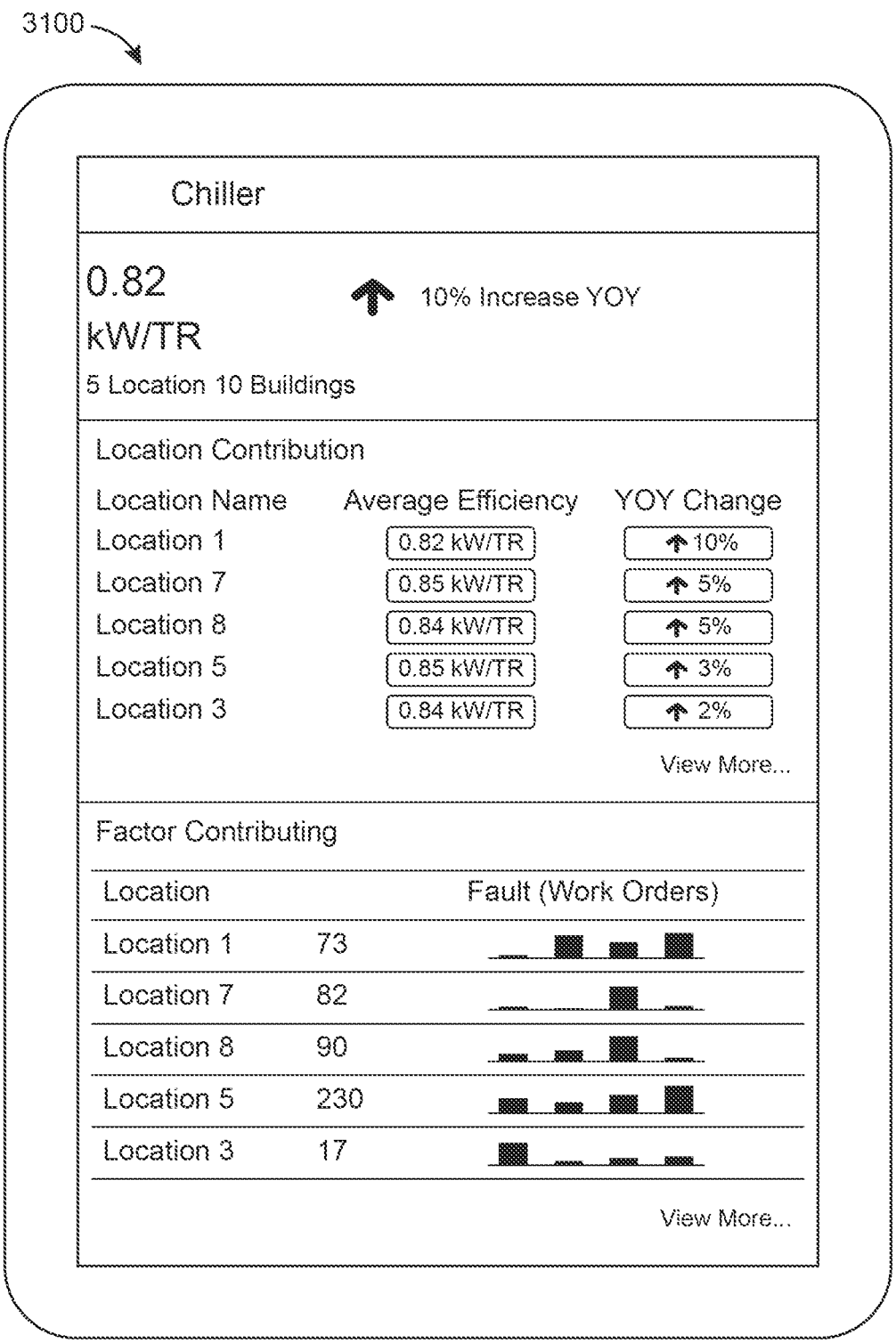

FIG. 31 is a schematic diagram of a user interface indicating the performance of a chiller and faults associated with the chiller, according to an exemplary embodiment.

DETAILED DESCRIPTION

Referring generally to the FIGURES, systems and methods are shown and described for monitoring social distancing and performing contact tracing in a building, according to an exemplary embodiment. Furthermore, the systems and methods described herein can enhance employee care, provide employee duress services, facilitate building navigation, and various other services. A building system can collect tracking data (e.g., real-time and/or historical data collected from various data sources such as a badge tracing system, an asset tracking system, etc.) to determine insights about the movements and behaviour of occupants, utilization of equipment and spaces, and various other insights. The building system can provide user interfaces including analytics for social distancing and/or contact tracing for the building determined based on the tracking data. For example, the user interface could include reports and/or real-time alerts highlighting areas of a building where occupancy levels are too high to allow for social distancing or events where occupants have come into contact.

In some cases, a building may be closed due or operate at a limited capacity to the presence of an infectious disease (e.g., a virus, bacterial infection, etc.). The social distancing and contact tracing services of the building system described herein can help the building reopen quickly and safely by taking into account the health and behavior of occupants of the building. By performing real-time social distancing monitoring, contact tracing, scenario planning, and/or lone worker detection and support, a building can reopen and/or operate while taking into account the health and safety of occupants, even in the midst of a scenario where a disease is spreading rapidly, e.g., during a pandemic, epidemic, etc.

Based on the social distancing and contact tracing services described herein, the building system can protect the health and safety of occupants of a building and reassure occupants of the safety of the building. Furthermore, during operation of the building, the social distancing and/or contact tracing services described herein can minimize disruption and employee stress resulting from the infectious disease (e.g., when an employee becomes sick and/or tests positive). In some embodiments, the building system can integrate the social distancing and/or contact tracing services with other services of a building, e.g., HVAC control and monitoring.

Furthermore, the building system can implement security based occupant tracking and zoning rules where alerts are generated when an occupant enters a restricted area. In some embodiments, the building system can facilitate building evacuation, occupancy checking, and occupant mustering. The building system can implement space utilization tracking and generate metrics indicating occupant usage of spaces within a building. The building system can implement health and safety features including duress support for a lone worker, panic buttons for fire and security building evacuations, etc. In some embodiments, the building system can implement analytics for workflow and/or collaboration. In some embodiments, the building system can implement asset tracking and/or utilization for empirical measures of equipment utilization.

The building system, through the social distancing and contact tracing services can help a building prepare for an infectious disease, to prevent the spread of an infectious disease, and respond appropriately when occupants contract an infectious disease. The building system can provide user interfaces that indicate metrics associated with social distancing and/or contact tracing services. The user interfaces can be provided via a mobile application, an web page, a software program, etc. The user interfaces can be integrated with other interfaces of building applications, for example, HVAC control and monitoring interfaces.

Figure 1:
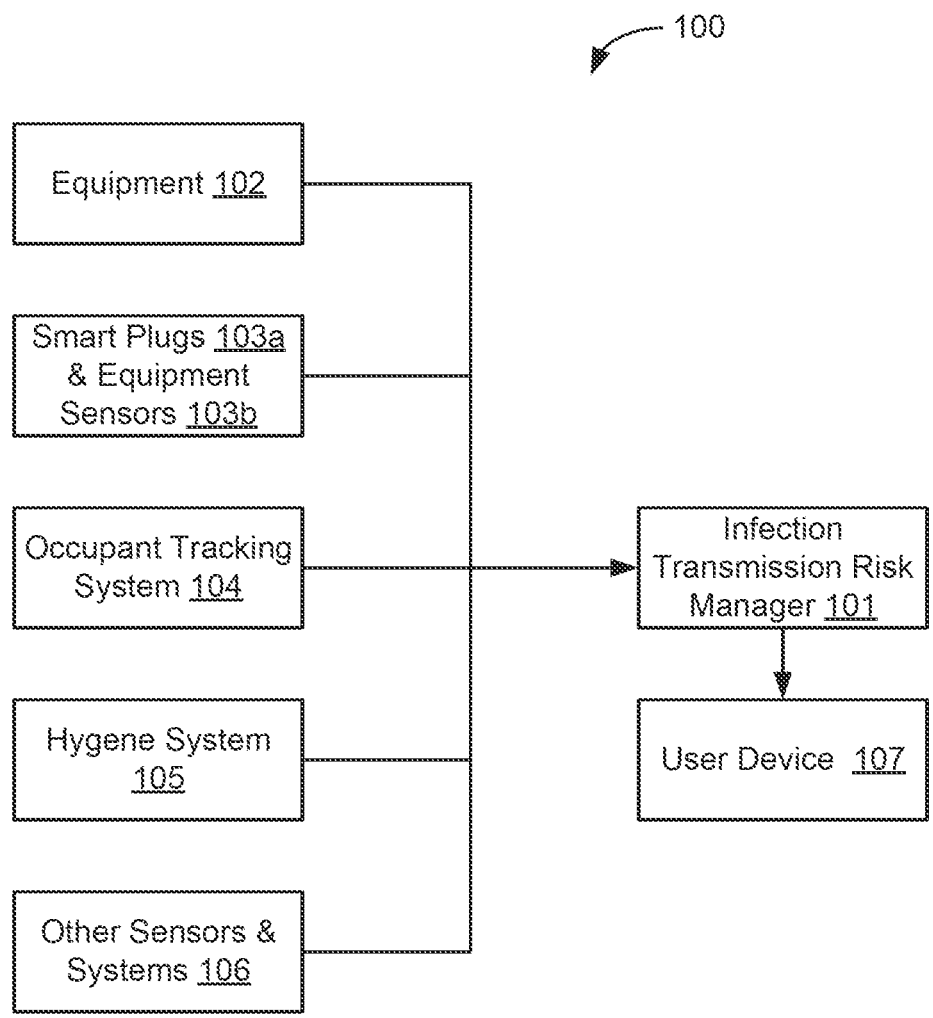
FIG. 1 is a block diagram of a system for managing infection risk within a monitored area, according to an exemplary embodiment.

Referring now to FIG. 1, a block diagram of a system 100 for infection transmission risk management of a building or other monitored area is shown, according to an exemplary embodiment. A monitored area may include an office, hospital, research laboratory, industrial, or commercial space, or any other shared space in which a monitoring of infection transmission risk is required. The monitored area may include various equipment that may be used by or interacted with by building occupants. To provide a method of managing infection transmission risk of persons to other persons through direct person-to-person interaction, indirect transmission through sharing of spaces, and potential contamination of common surfaces, system 100 monitors the location and use of equipment, and the location of individuals and their interactions with different people, spaces, and equipment, to support social distancing recommendations and infection risk management practices in response to a current disease epidemic, to assess and record transmission risk events, and to track and record interactions and locations for the purposes of contact tracing. As described in detail herein, system 100 is configured to receive various types of data from various types of data sources, process the data to identify possible contagion transfer risk for occupants, spaces, and equipment, generate social distancing risk events, contact tracing data and histories, risk analysis, and disinfection or cleansing data, and generate alerts, notifications, reports, and various graphical user interfaces displaying and reporting this information. System 100 thereby provides technical improvements to infection transmission risk management and assessment, by providing responses to transmission risk events, assisting an operation in more effectively managing the transmission risks associated with an infectious disease.

While the present disclosure generally discusses methods and systems for mitigating the risk of spread of an infectious disease, it should be understood that the features disclosed herein could be utilized for a wide variety of other implementations as well. For example, in some embodiments, the present features could be used to prevent against spread of a dangerous substance, such as one that is spread via movement of occupants. In other embodiments, the features may be used to track and improve compliance with any sort of policy, such as a maximum occupancy policy for a space for purposes such as fire risk mitigation. All such modifications are contemplated within the scope of the present disclosure.

As shown in FIG. 1, the system 100 includes an infection transmission risk manager 101, equipment 102 communicable with the infection transmission risk manager 101, smart plugs (e.g., devices plugged into power outlets) and equipment sensors 103A and 103B communicable with the infection transmission risk manager 101, occupant tracking system 104 communicable with the infection transmission risk manager 101, hygiene system 105 communicable with the infection transmission risk manager 101, and other sensors and systems 106 communicable with the infection transmission risk manager 101. The system 100 is also shown to include a user device 107 communicable with the infection transmission risk manager 101.

Equipment 102 may include various devices that are used by occupants of the monitored area in the course of their work or occupation. For example, in a laboratory, equipment 102 may include centrifuges, microscopes, x-ray diffraction units, mass spectrometers, chemical processing equipment, computing resources (supercomputers, servers, etc.), incubators, and imaging systems, among many other possibilities depending on the research goals and particular scientific focus (e.g., pharmaceutical, biotechnology, food science, physics, etc.) of the laboratory. In a hospital space, equipment 102 may include ventilators, life monitoring devices, and other devices and equipment for the treatment of patients and conduct of hospital activities. In an office space, equipment 102 may include photocopiers, vending machines, conference telephones, monitors, displays, HVAC equipment (e.g., thermostats, VAV boxes, valves, dampers, AHUs, chillers, etc.), and/or any other type of equipment In some embodiments, the equipment 102 is configured to collect data relating to operation of the equipment 102. For example, a device of equipment 102 may be configured to store a log of when the device is turned on/off, how long the device is used for, what functions the device is commanded to perform, etc. In such a case, the equipment 102 obtains operating data that describes when the equipment 102 is in-use (operating, active, executing a task, etc.) or out-of-use (off, idle, etc.). The equipment 102 may be communicable with the infection transmission risk manager 101 (e.g., via information technology network (e.g., Ethernet, Wi-Fi, etc.) or a building network (e.g., BACNet, MSTP, etc.) to provide the operating data to the infection transmission risk manager 101.

The equipment 102 may consume one or more utility resources (e.g., electricity, natural gas, water, etc.) or specialty resources (distilled water, specialty chemicals, radioactive materials, liquid nitrogen, atmospheric gases, life support gases, office equipment consumables, such as printer ink and toner, etc.). In some embodiments, the equipment 102 is configured to measure the resource consumption of the equipment 102. The amount or rate of resource consumption may correspond to a status of the equipment 102. For example, a device of equipment 102 may consume a first amount of electricity when in an idle or off state, a second amount of electricity during start-up of the device or during configuration of a task for the device, and a third amount of electricity while performing a primary function of the device (e.g., executing a task, etc.). The different amounts may be known, experimentally-determinable, or determinable by employing machine learning methods, such that they can be used to determine the status of the equipment 102. Various statuses are possible depending on the functionality of a given device. Although the examples herein are described primarily in terms of electrical power consumption, it should be understood that embodiments using measurements of any other type of resource consumed by equipment are also within the scope of the present disclosure.

Equipment 102 may draw electricity from a building electrical system via smart plugs 103A. In the example shown, the smart plugs 103A are configured to be placed between a standard electrical outlet (e.g., wall outlet) and a power cord for a device of equipment 102. The smart plugs 103A can thereby be used with the system 100 without requiring any modification or specialization of the building electrical system. In other embodiments, the functions attributed herein to the smart plugs 103A may be performed by an element of the building electrical system (e.g., smart wall outlets, etc.).

Each smart plug 103A is configured to measure the amount or rate of electrical power passing therethrough to obtain a time series of electrical power measurements ("power consumption data") and to transmit the power consumption data to the infection transmission risk manager 101. The power consumption data may include both an amount or rate of electrical power consumption and a time stamp associated with that amount or rate. The smart plugs 103A may be communicable with the infection transmission risk manager 101 via a wireless network, for example a WiFi network or cellular network.

Equipment 102 may also be fit with equipment sensors 103B configured to detect an interaction with or use of equipment 102. For example, a door of a refrigeration unit may be equipped with a sensor that detects when it has been opened or closed. Equipment sensors 103B may be communicable with the infection transmission risk manager 101 via a wireless network, for example a WiFi network or cellular network.

The occupant tracking system 104 is configured to track occupants (people) in the monitored area. Various types of occupant tracking systems are included in various embodiments. For example, in some embodiments the occupant tracking system 104 is implemented as part of an access and security system, in which a user can enter or exit a space by presenting a badge to an electronic card reader (e.g., RFID, magnetic stripe, etc.). The occupant tracking system 104 may monitor occupant locations based on entry into various secure spaces.

In other embodiments, the occupant tracking system 104 includes multiple beacons, with each beacon associated with an occupant, and a set of transceivers configured to determine the locations of the beacons. The transceivers can be Bluetooth Low Energy (BLE) transceivers, 5G transceivers, Wi-Fi transceivers, etc. The beacons may be formed as Bluetooth Low Energy (BLE) badges, Ultra-wideband (UWB) badges, or badges using a similar radio communications technology, which may be worn or carried by personnel in the monitored area. The transceivers may be arranged around the monitored area. Each transceiver is configured to detect the presence of the beacons and determine a distance from a beacon to the transceiver. Based on the distance of a beacon to three or more transceivers (trilateration and/or triangulation), the location of the beacon can be determined with a high degree of accuracy. Such a system allows for occupant tracking across spaces regardless of whether the spaces are separated by walls or doors and to precisely locate occupants within a space.

In other embodiments, the occupant tracking system 104 includes devices monitoring person-to-person proximity events, e.g., smartphones running an app that determines proximity through strength of Bluetooth signals, WiFi signals, sonic pings, or other method.

Hygiene system 105 may include dispenser devices configured to provide washing or disinfectant agents for the purposes of hand washing support and such dispenser devices may be equipped with sensors indicating levels of washing or disinfectant agent present in a device. Hygiene system may further include hygiene monitoring devices and systems configured to monitor compliance with recommended hygiene operations, such as whether a hand washing operation was carried out or whether a person complied with a correct hand washing technique and duration. Hygiene system 105 and the devices thereof may be communicable with the infection transmission risk manager 101 via a wireless network, for example a WiFi network or cellular network.

The system 100 is also shown as including other sensors and systems 106. The other sensors and system 106 may provide various data relating to occupancy of the space or usage of equipment 102 in various ways. For example, a calendaring or scheduling system may be included that provides information about meeting times, holidays, event schedules, which may be relevant to analyzing space utilization. As another example, other sensors that measure usage or inventory may be included, for example a smart toilet sensor that measures a number of flushes and provides such information to the infection transmission risk manager 101. As yet another example, other sensors that measure interaction of a person with a device of equipment 102 may be included, for example, pressure or motion sensors detecting removal of a piece of equipment 102 from a location, etc. The present disclosure contemplates inclusion of any such available data in various embodiments.

The infection transmission risk manager 101 is configured to receive equipment operating data from the equipment 102 and/or the smart plugs 103A and equipment sensors 103B, occupancy data from the occupant tracking system 104, hygiene consumables and compliance data from the hygiene system 105, and, in some embodiments, other usage-related data from the other sensors and systems 106. The infection transmission risk manager 101 may associated the data points with one or more of multiple people, equipment, or spaces of the monitored area. The infection transmission risk manager 101 is also configured to process the data to determine an equipment usage and transmission risk data, a space usage and transmission risk data, an occupant presence and/or location data, an occupant infection transmission risk data in respect of person-to-person direct contact, indirect transmission risk due to shared use of equipment or spaces within a monitored area, and an occupant social distancing policy breach. The infection transmission risk manager 101 is also configured to generate a graphical user interface illustrating transmission risk alerts, social distancing policy breaches, risk ratings for people, spaces, or equipment, and to cause the user device 107 (e.g., smartphone, laptop, desktop computer, etc.) to display the graphical user interface. These and other features are described in detail below.

Figure 2:
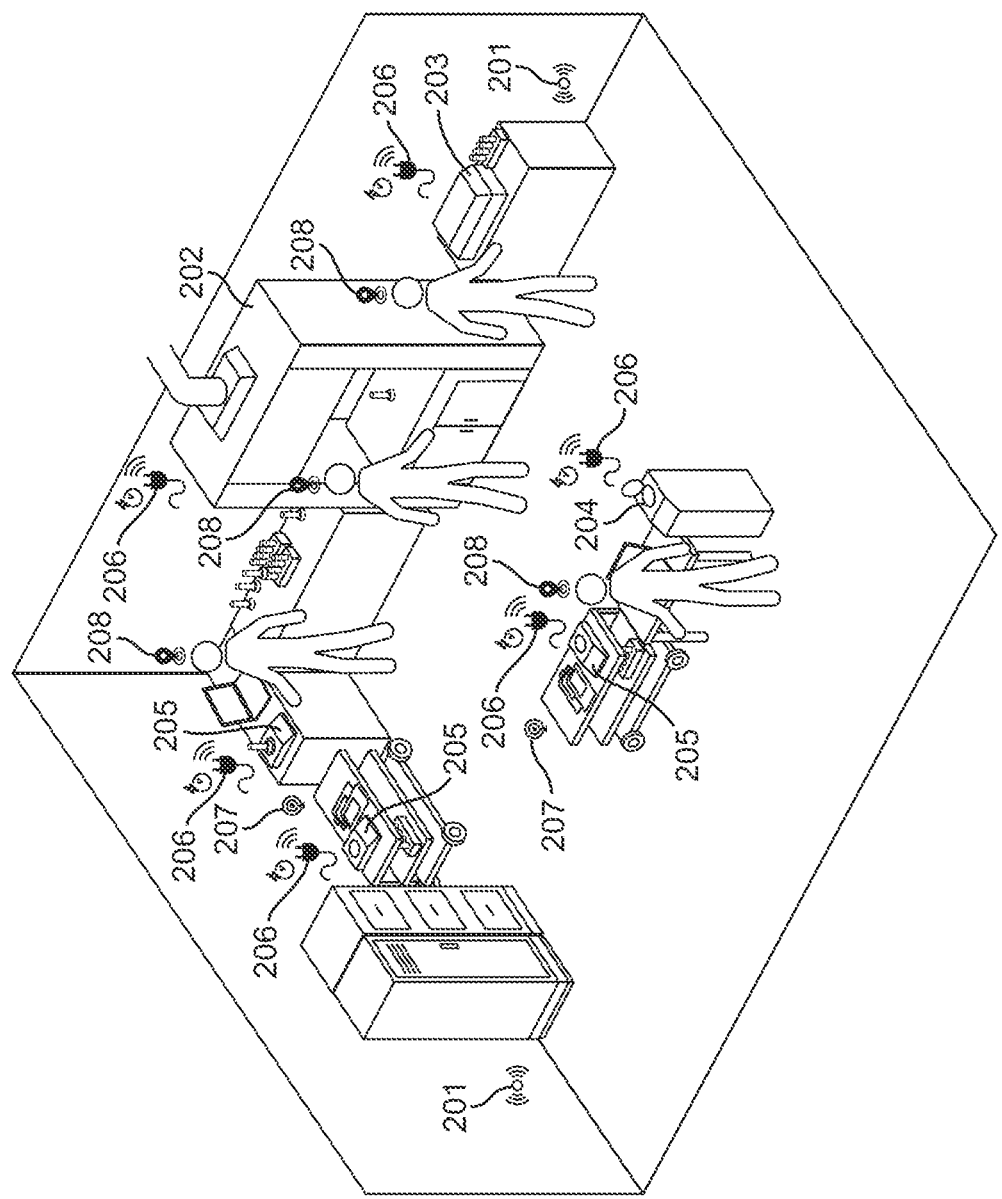
FIG. 2 is a perspective view of a monitored space of a monitored area served by the system of FIG. 1, according to an exemplary embodiment.

Referring now to FIG. 2, a perspective view of an example space within a monitored area served by system 100 is shown, according to an exemplary embodiment. In this example, the space is used as a laboratory, however systems and methods described in the present disclosure may also apply to other settings, such as hospital or medical facilities, including field hospitals, retail, industrial or manufacturing facilities, data centers, or commercial office spaces. In this example, the space is geofenced using sensors 201 (e.g., Bluetooth Low Energy (BLE) or Ultra-wideband (UWB) transceivers) included with occupant tracking system 104. The sensors 201 are arranged to provide occupant detection around a perimeter of the space. FIG. 2 also shows various equipment 102, including a fume hood 202, water bath 203, centrifuge 204, and scales 205. These devices of equipment 102 are connected to smart plugs 103A. In the embodiment shown, mobile equipment (e.g., scales 205 in FIG. 2) includes a location tag 207 (e.g., a BLE or UWB beacon) which can be tracked by the sensors 201 of the occupant tracking system, for example to determine which space the mobile equipment is in at a given time. The occupants are shown to be carrying locations tags 208 (e.g., BLE or UWB badges) which can be determined via trilateration, triangulation, etc. using data from the sensors 201 of the occupant tracking system 104. The array of sensors, trackers, plugs, equipment, etc. provides an example of the hardware which may be included in a monitored area, such as laboratory, to facilitate the utilization monitoring described herein.

Figure 3:
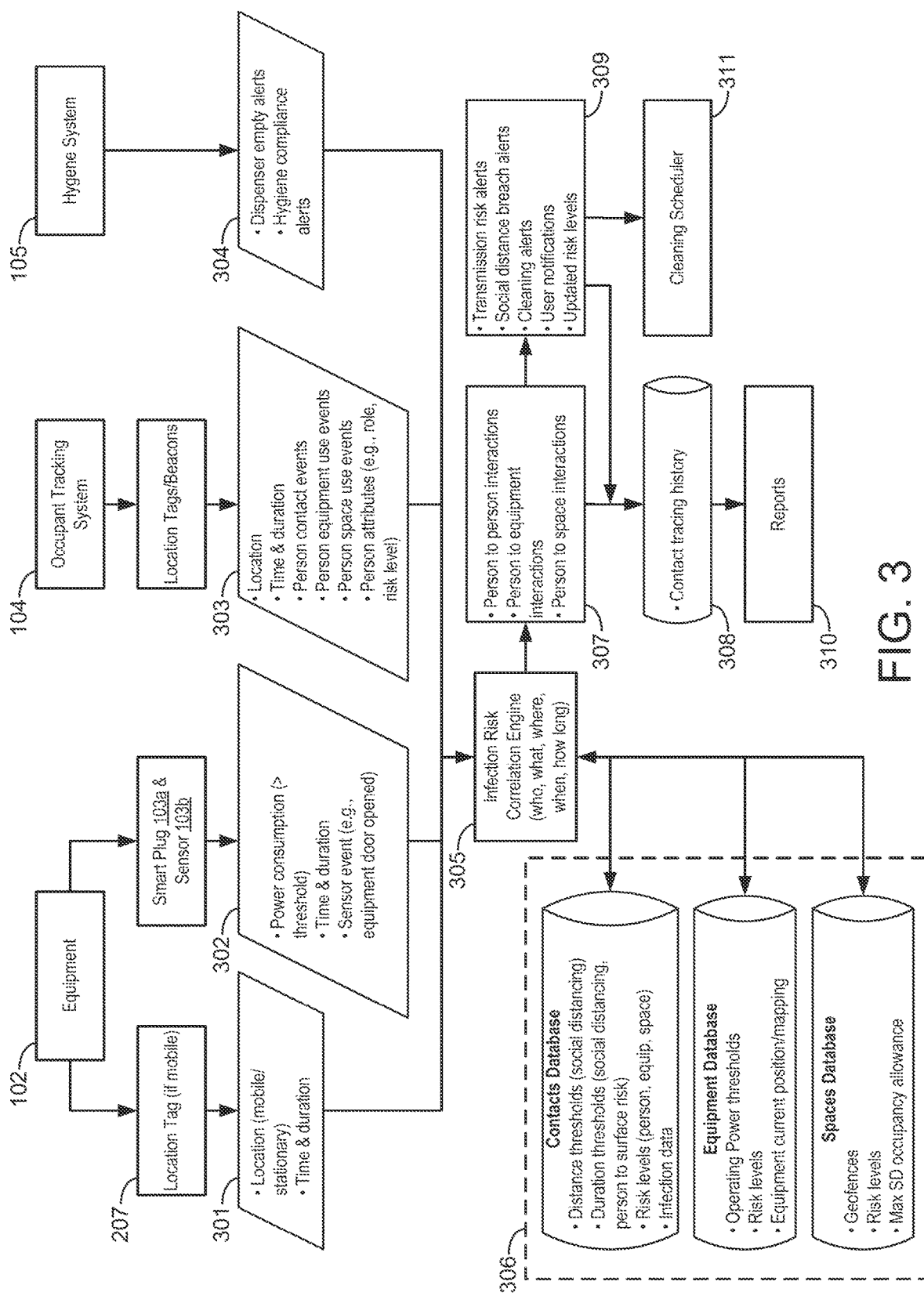
FIG. 3 is a schematic diagram of one example of the system of FIG. 1, according to an exemplary embodiment.

Referring now to FIG. 3, a schematic illustrating the elements of the system 100 and the data transfers and associations there is shown, according to an exemplary embodiment. As illustrated by FIG. 3, equipment 102 is connected to a smart plug and, where applicable, sensors indicating interactions with the equipment (e.g., door sensor on an equipment device) 103A and 103B, and, in the embodiment shown, to a location tag (e.g., location tag 207 of FIG. 2). The location tag is used, as shown in block 301, to provide data relating to the location of the equipment 102 and a time and duration relating to such equipment 102. That is, the data at block 301 may include locations of the equipment associated with time stamps, such that the amount of time the equipment 102 spends in any particular space can be ascertained. The smart plug 103A is shown to provide power consumption data and time and duration relating to such power consumption (e.g., a time series of power consumption values) at block 302. In some embodiments, the smart plug 103A only reports the power consumption when the power consumption is above a threshold value. The smart plug 103A may be configured to provide an identification code or other information that associates a particular smart plug 103A (and the data provided thereby) with a particular unit of equipment 102. The equipment sensors 103B may be configured to report an interaction of a person with the equipment, for example, a door sensor on a refrigeration unit. Sensors 103B may report its location data and time and duration of a sensor state. Power consumption data and sensor data may be used by the system 100 to determine that equipment is or is not in use.

FIG. 3 also shows that occupant tracking system 104 provides locations of occupants, the time and duration associated with such locations, attributes of the occupants (e.g., role, job title, risk level etc.), person contact events with persons, equipment, and spaces at block 303. The occupant tracking system 104 thereby provides the information needed to assess the number of people who used a space over a time period, and the types of persons that utilized the space. For example, researchers, janitors, interns, senior management, people with high, medium, or low risk levels, and different groups within a hospital or laboratory scenario, such as medical staff working with contagious patients and those working with non-contagious patients, or laboratory staff working near contagions, etc.

FIG. 3 also shows that a hygiene system 105 provides data about dispenser device empty alerts and hygiene compliance alerts at block 304.

As illustrated in FIG. 3, the data from block 301, block 302, block 303, and block 304 are provided to infection risk correlation engine 305. The infection risk correlation engine 305 may be executed by the infection transmission risk manager 101 of FIG. 1. As shown in FIG. 3, the infection risk correlation engine 305 may also receive various pre-stored parameters from various databases 306 of the infection transmission risk manager 101 of FIG. 1. The databases 306 are shown as specifying data about contacts, equipment, and spaces. For example, spaces database may contain one or more geofenced spaces (e.g., defined based on a boundary of such a space), space risk level ratings, maximum number of occupants under normal conditions, and maximum number of occupants under contagion conditions (derived from maximum social distancing allowances). Contacts database may contain social distancing time and duration thresholds, contact risk levels associated with person-to-person contacts, or person-to-surface or person space use contacts, and data about infection, such as incubation periods, infectivity periods, transmission dynamics, risk factor data, or immunity data. Equipment database may contain information about equipment such as operating power thresholds (below which an equipment may be determined to be not in use, such as when in an idle or sleep mode), equipment infection risk levels (e.g., a piece of equipment may, by its nature and use, be more at risk of contamination or, conversely, may have a low risk of contamination), and equipment current position or mapped location within the monitored area. The parameters in the databases 306 can be configured/edited by a user to facilitate operation of the infection risk correlation engine 305 and, additionally, may be updated by the outputs of the infection risk correlation engine 305.

The infection risk correlation engine 305 may use the input data described above to determine various events, alerts, or insights, such as person-to-person interactions giving rise to transmission risk alerts or that are used for contact tracing histories. In addition, infection risk correlation engine may use input data to determine events, alerts, or insights in respect of contamination of equipment or spaces, based on detected uses or interactions of tracked individuals. Such information may similarly be used for contract tracing. Infection risk correlation engine 305 may generate alerts, such as social distancing breach alerts, infection transmission alerts, cleaning alerts, user notifications, and updated risk levels for people, equipment, and spaces. In addition, infection risk correlation engine 305 may receive data inputs from hygiene system 105 in respect of cleaning data from a hygiene system including cleansing fluid dispensers and hand washing monitors. Such data may include alerts that a dispenser is empty or alerts of a hygiene compliance issue. Infection correlation engine may use these data inputs to update risk levels for persons, equipment, or spaces and may generate targeted cleaning alerts to a cleaning scheduler or other system. Infection risk correlation engine may cause a contact tracing history database to be updated and reports of contact tracing generated. Infection risk correlation engine may, additionally, cause one or more notifications to occupants concerning risky contacts or social distancing breaches. Illustrations of the outputs of infection risk correlation engine 305 described above are indicated by block 307, block 308, block 309, block 310, and block 311.

Detecting Person-to-Person Contacts

One implementation of the present disclosure is a method of detecting interactions between people that create a risk of person-to-person infection.

Figure 4:
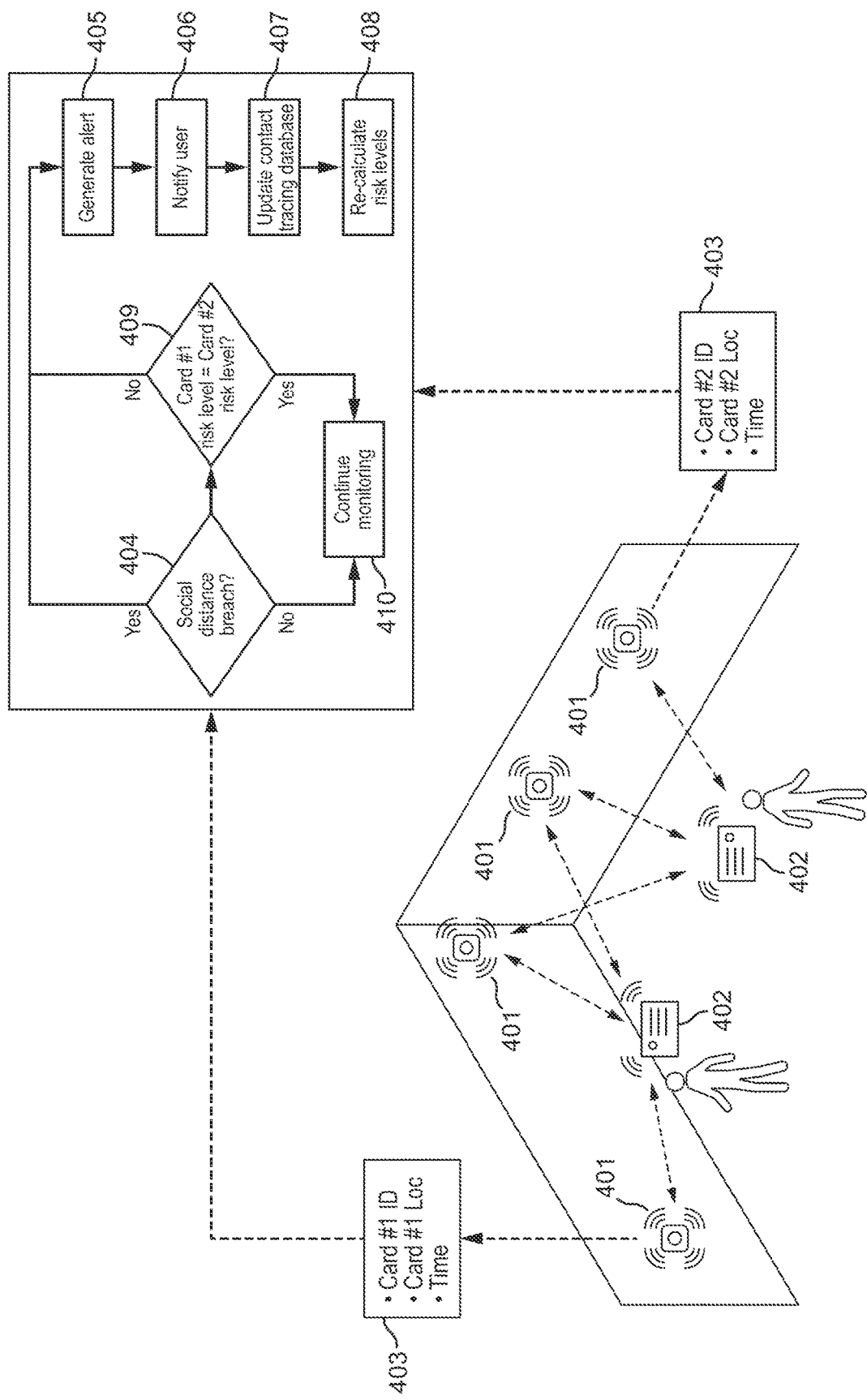
FIG. 4 is a diagram showing an implementing system for detecting person-to-person contacts, according to some embodiments.

Referring now to FIG. 4, a stationary transceivers 401 installed within a monitored area detect the location of beacons 402 worn by persons occupying the monitored area. In some embodiments, the beacons include Bluetooth Low Energy (BLE) badges, Ultra-wideband (UWB) badges, or badges using a radio communications technology with an accuracy suitable for indoor location tracking. In some embodiments, the stationary transceivers include transceivers using a communications technology corresponding to that of the beacons. Tracking positions of the beacons may include, for each beacon, detecting, by each of three or more transceivers, a distance between the transceiver and the beacon and performing a trilateration calculation, a triangulation calculation, etc. based on the distances and the positions of the transceivers to determine a position of the beacon. When beacon 402 is within range of transceiver 401, it transmits information 403 including its beacon identifier, the identifier of any beacon that has come within its contact range (as defined by system 100), and time data. Information 403 may be analyzed to determine whether a social distance breach has occurred 404. In the event of a social distance breach, the system generates an alert 405, notifies the user in step 406, updates a contact tracing database 407, and may re-calculate a risk level for the respective beacons 401, relating to the risk level assigned to particular occupants or class of occupants. If a comparison of the risk levels of two beacons leads to a determination that they are of different risk levels 409, alert 405, notification 406, database update 407, and risk level re-calculation 408 may occur. Where no social distance breach has occurred and there is no difference in risk levels, the system continues monitoring 410.

Figure 5:
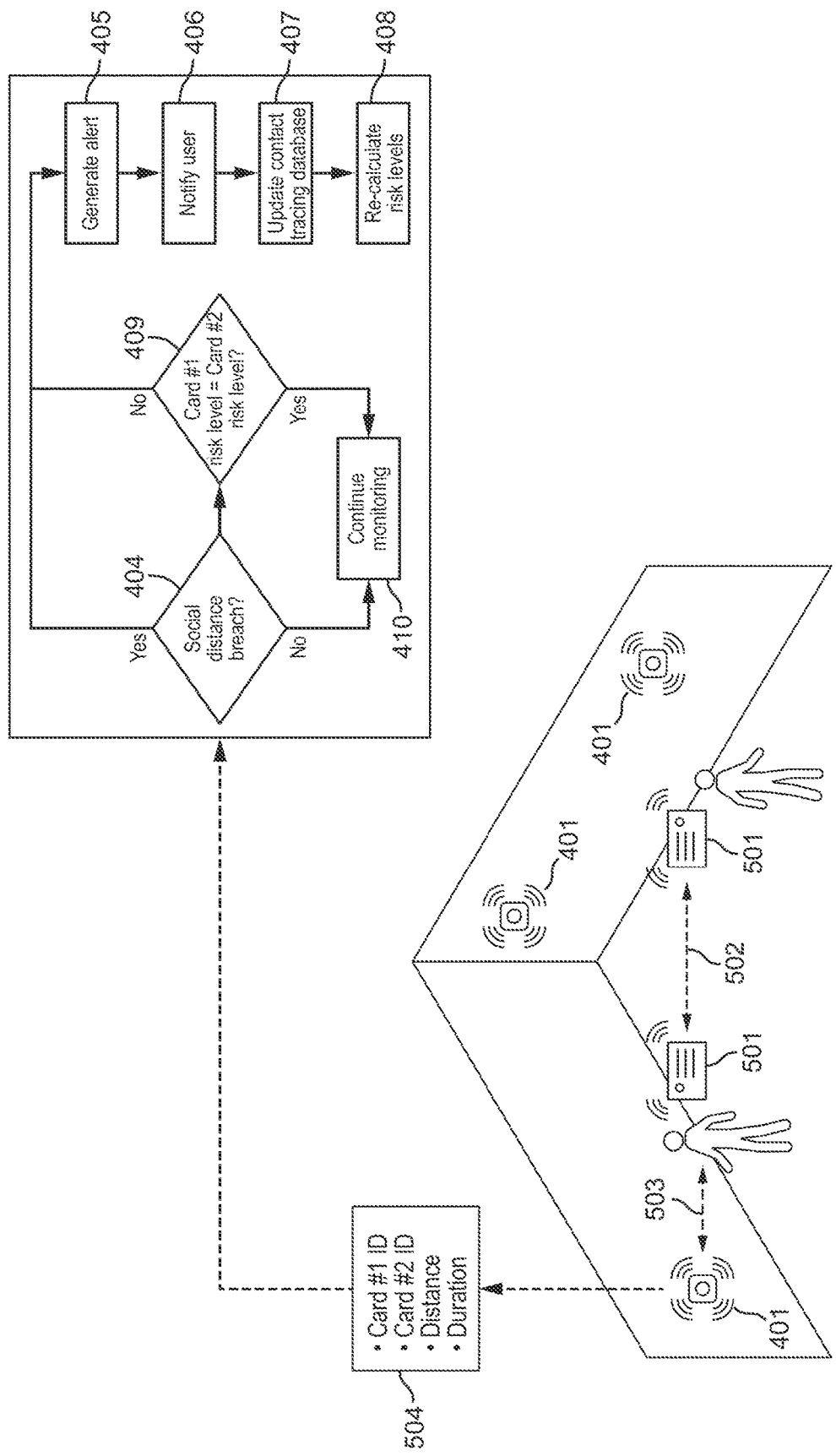
FIG. 5 is a diagram showing another implementing system for detecting person-to-person contacts, according to some embodiments.

Referring now to FIG. 5, an alternative embodiment of the method of FIG. 4, based on communications between badge transceivers 501 carried or worn by persons occupying the monitored area. In this embodiment, badge transceivers 501 are Bluetooth Low Energy (BLE) transceivers, Ultra-wideband (UWB) transceivers, or other badge transceivers using a radio communications technology with an accuracy suitable for indoor location tracking. Badge transceivers additionally include processing circuitry, memory, storage, and computer-readable instructions that can be executed by the processing circuitry. In some embodiments, badge transceivers are not badges, but devices, such as mobile or wearable devices. The stationary transceivers 401 installed within a monitored area detect the location of the badge transceivers 501 worn by persons occupying the monitored area. Tracking positions of the badge transceivers may include, for each badge transceiver, detecting, by each of three or more stationary transceivers, a distance between the stationary transceiver and the badge transceiver and performing a trilateration and/or triangulation calculation based on the distances and the positions of the stationary transceivers to determine a position of the badge transceiver.

In some embodiments, each badge transceiver transmits its identification data and location and each location is timestamped and saved by the badge transceiver 502. In other embodiments, the badge transceiver only records its location and location timestamp upon detecting another badge transceiver. Badge transceiver receives transmissions from other badge transceivers within range. Upon detecting another badge transceiver, badge transceiver receives the other badge transceiver's location with timestamp. The transceivers collect the badge transceiver identification data, badge transceiver location, and time of location and transmit this information to a remote infection risk management system.

In other embodiments, badge transceiver only calculates the distances between itself and other detected badge transceivers and the timestamps of each distance measurement and then transmits this information to the nearest stationary transceiver for onward communication to and processing by the infection risk management system. In some embodiments, badge transceiver detects a distance between itself and another badge transceiver that meets a rule distance criterion and badge transceiver records the time the criterion was met. Badge transceiver continues to calculate its distance from the other badge transceiver and, upon detecting that the distance criterion is no longer met, records the time that the criterion is no longer met. Badge transceiver may either calculate that the time duration meets the time criterion or may simply send the duration of the record of the distance criterion being met to the infection risk management system. In some embodiments, each badge transceiver sends this information to the nearest stationary transceiver as soon as it is within range 503. In some embodiments, badge transceivers may send this information to other badge transceivers within range. Information 504 sent to the infection risk management system may be analyzed in a similar manner to that described above in relation to FIG. 4.

In other embodiments, badge transceivers may be equipped with Near-Field Magnetic Induction (NFMI) communication technology configured to generate short-range magnetic fields and detect the presence of other such NFMI-enabled badge transceivers within the range of such magnetic fields. In such an embodiment, the short range of NFMI (approximately 2 meters) allows the system to be configured such that a straightforward detection of another card could raise an alert in the system of a contact between persons that breaches a social distancing policy, or that may create a change in the risk levels of the occupants to which the badge transceivers are associated. A communication with the infection transmission risk manager, and a similar analysis of the nature of contact and the impact on risk levels, may occur upon such a detection, in a manner similar to that described above and in relation to FIG. 4.

Figure 6:
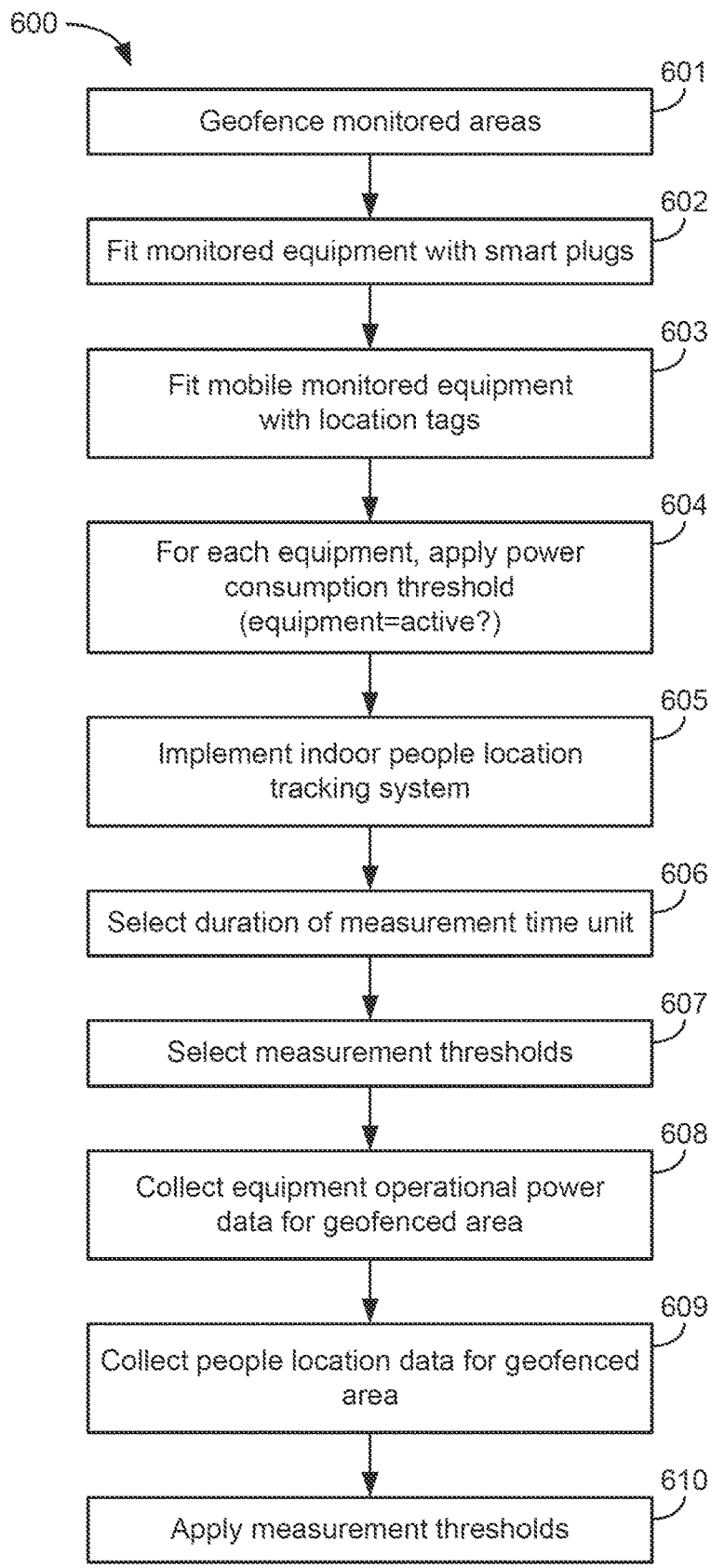
FIG. 6 is a flowchart of a method of configuring the system and recording various data, according to some embodiments.

Referring now to FIG. 6, a flowchart describing a process of configuring a system and recording data is shown, according to an exemplary embodiment. At step 601, monitored areas (spaces) are geofenced. For example, the boundaries of the spaces may be virtually defined within system 100 to denote the geographic limits of each space. In some cases, each space is differentiated by a wall or other physical structure. In other cases, two or more spaces may be open or continuous but defined as separate spaces using a geofencing approach at step 601.

At step 602, equipment 102 is fit with smart plugs 103A. For example, each device of equipment 102 may be associated with a particular smart plug 103A attached to a power cord of the device. Step 602 may include configuring the infection transmission risk manager 101 to map each smart plug 103A (and the data provided thereby) to a particular device of equipment and/or to a type of equipment.

At step 603, mobile/movable devices of equipment 102 (i.e., devices that are configured to be moved to various spaces of the laboratory over time) are fit with location tags (e.g., trackable beacons). Step 603 may include configuring the infection transmission risk manager 101 to associate each location tag with the corresponding equipment 102, i.e., such that the infection transmission risk manager 101 can determine which equipment 102 is present in a space based on tracking data from a particular location tag.

At step 604, a power consumption threshold is defined for each device of equipment 102. For example, the infection transmission risk manager 101 may store a set of power consumption thresholds (e.g., values of amounts or rates of power consumption) for each type of equipment 102 or for each particular device of equipment 102. Step 604 may include mapping each device of equipment (and, in concert with step 602, each smart plug) with a power consumption threshold. The power consumption thresholds can be determined experimentally and/or input by a user, or may be determined using machine learning methods.

At step 605, the occupant tracking system 104 is installed and configured. For example, the occupant tracking system 104 may be configured to coordinate with the geofenced borders defined at step 601, i.e., such that the occupant tracking system 104 is configured to provide data relating to which geofenced space an occupant is located in. In some embodiments, step 605 includes configuring the occupant tracking system 104 and/or the infection transmission risk manager 101 to associate each of multiple occupant beacons with a particular user and/or a type of user (e.g., based on role, job title, etc.).

At step 606, the duration of measurement time units is selected. For example, as described above, the equipment and occupancy utilization can be calculated based on a discretized set of sub-periods (measurement time unit), the length of which can be selected at step 606. Step 606 thereby allows tailoring of the temporal resolution of the utilization logging described herein.

At step 607, measurement thresholds and parameters are set. The measurement thresholds and parameters may include minimum dwell times for an occupant to be counted as occupying a space. The measure thresholds and parameters may also include assumed (automatically added) equipment set-up, start-up, shut-down, or cleaning times. In some embodiments, the measurement thresholds and parameters include expected or maximum occupancy values, weighting factors, or other terms that customize the utilization calculations based on the type of space being evaluated.

At step 608, power consumption data for equipment in a space (e.g., within a geofenced boundary) is collected. For example, the power consumption data may be measured by the smart plugs 103A and transmitted to the infection transmission risk manager 101 via a wireless network. The power consumption data may be stored by the infection transmission risk manager 101 for later use in identifying possible incidents of infection transmission.

At step 609, occupancy data is collected for the geofenced space. For example, the occupant tracking system 104 may provide data relating to the positions of tracked personnel in the space (e.g., the determined locations of tracked beacons in the space). The occupancy data may include timing information describing when an occupant entered or left a space. The occupancy data may be stored by the infection transmission risk manager 101 for later use in identifying possible incidents of infection transmission.

At step 610, measurement thresholds are applied. For example, at step 610 the infection transmission risk manager 101 may remove occupancy data that indicates an occupant present in a space for less than the minimum dwell threshold. As another example, at step 610 the infection transmission risk manager 101 may determine the statuses of the equipment 102 over time by comparing the power consumption data to the power consumption threshold(s) for the equipment 10. Applying the measurement thresholds 610 may thereby result in a set of occupancy data that defines a number of occupants at a space for each of multiple sub-periods and a number of active devices of equipment for each of the multiple sub-periods.

Social Distancing Occupancy Alerts

One implementation of the present disclosure is a process for detecting an unsafe number of people in an area, in breach of minimum social distancing advice, according to some embodiments. If too many people enter the room it should trigger an alert and an short service message (SMS) or other notification should be sent to all people that entered. The alert may appear as a notification on a UI dashboard, as a push notification to a mobile device, as a visual or auditory alert within the room, or some other method.

The rule for the required distance between people may be hard-coded, entered by the user as a numerical value, derived from a user's selection of a known contagion, automatically updated through calls to a remote service, or set through some other method. In some embodiments, the system applies multiple different rules in parallel, representing different parallel contagions, different models of the same contagion, or for some other purpose.

In some embodiments, the social distancing monitoring system is configured with a rule specifying the maximum number of occupants within a defined space, such as a room. The maximum number of occupants may be set manually for each space or may be determined through calculation. For example, the area of the room may be manually provided, or calculated from the geofence definition, and then divided by the area of required space around an individual occupant. In some embodiments, the system utilizes an algorithm to pack circles, representing the required social distancing area around an individual, into the geometry of the room, and the maximum occupancy is the maximum number of non-overlapping circles that fit into the space. The tracking of occupancy may be performed by defining geofenced regions, and then tracking individuals entering and leaving those regions.

In some embodiments, the social distancing monitoring system is configured with a rule specifying criteria for a maximum distance between two beacons and a maximum time period during for the distance between two beacons being shorter than the maximum distance. Where the system detects that the time and distance criteria of the rule are met in respect of two beacons, the system generates an alert to the user (e.g., by sending a notification to a cellphone associated with that user's beacon). A social distance rule breach alert is raised and sent to a monitoring client and a contact tracing database is updated.

Badge transceiver may contain instructions including a social distancing rule specifying distance and/or time criteria that, if met, cause badge transceiver to generate a social distancing breach alert. In some embodiments, badge transceivers may transmit rule breach information for other badge transceivers to the nearest stationary transceiver within range. In some embodiments, the determination that a social distancing policy has been breached is made by the badge transceiver. In other embodiments, this determination is made by the system, using distance calculation data and time data provided by a badge transceiver. In some embodiments, a determination that a social distancing policy has been breached causes the system to generate an alert to the user (e.g., by sending a notification to a cellphone associated with that user's badge transceiver). A social distance rule breach alert is raised and sent to a monitoring client and a contact tracing database is updated.

In some embodiments, proximity detection alerting and contact tracing database updating may relate to a designation of an individual card holder as being a 'High Risk' individual, based on confirmation that the person has a positive diagnosis of an infectious disease.

In some embodiments, an occupancy for a monitored space may be determined using methods that do not require a person to have a badge or beacon, for example through the active or passive interaction of people with people-counting sensors (e.g., camera sensors, infra-red sensors, etc.) and other devices of an access control system, such as request-to-entry (REX) devices and other access control infrastructure indicating entry into or exit from a space. The people counting data from such systems may be analyzed by the infection transmission risk manager to determine whether a maximum safe occupancy of a monitored space has been exceeded or is close to being exceeded and generate an alert to the system, occupant notification, and event logging for reporting and further analysis.

Occupants, Spaces, and Equipment with Varying Degrees of Risk

Figure 7:
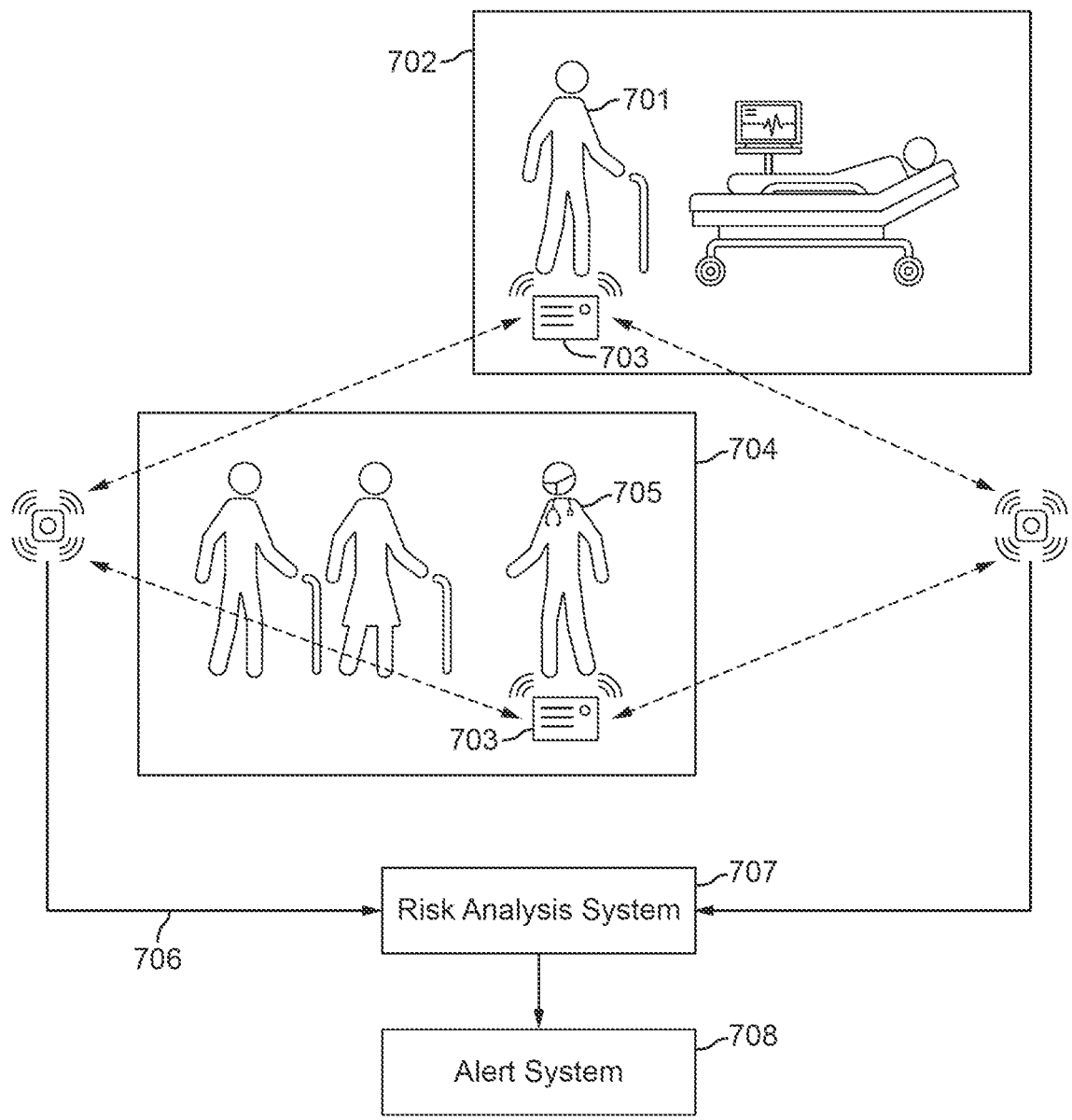
FIG. 7 is a diagram showing a process for detecting high risk individuals accessing monitored areas, according to some embodiments.

Referring now to FIG. 7, a method of detecting high risk employees or other personnel accessing safe areas or otherwise changing a risk rating of an area or the people using the area, is shown, according to an exemplary embodiment. ID cards 703 associated with individual users 701 and 705 may be given a risk rating, based on a role of a user (e.g., a person whose role brings them into contact with many new individuals) or an attribute of a user (e.g., user has been confirmed as testing positive for an infectious disease). Alternatively, a user may be identified in the system as an 'At Risk' user (e.g., a user with a particular risk factor for a current epidemic, such as their age or having a relevant pre-existing medical condition). A risk analysis system 707 that may form part of infection transmission risk manager 101 receives location tracking data 706 of persons with, e.g., a 'High Risk' rating and an alert 708 may be raised if the high risk user enters into an area geofence designated an 'At Risk' area 704 or an area otherwise required to be maintained at a low level of risk for contamination. In an alternative embodiment, the system may additionally designate an "At Risk" user group and those users monitored to ensure they do not enter into a 'High Risk' area 702 for contamination.

The system may additionally identify a risk rating for persons at low risk of contamination and notify users of their low risk. A person may be identified as low risk due to the person's role or an attribute of the person, such as immunity from past infection. In particular, for contagions to which adult populations are known to have a high percentage of immunity, such as Chicken Pox, identifying low risk individuals may enable organizations to continue to operate with minimal disruption.

The risk analysis system may use data about the proximity of individual users with different risk ratings to create new risk ratings for users. For example, a high risk individual may come into contact with a low risk individual, leading to a re-classification of the low risk individual as one of a medium risk group. Additionally, individual user notifications could be sent to users to notify of a risky contact. A contact tracing database may be updated with these interactions, and an alert may be sent to a monitoring client application.

The system may additionally record the identities of individuals with a high transmission risk rating, the identities of individuals they were in close contact with (as defined by the system), and the duration and location of the interaction. The monitoring system may generate a prioritized list of persons that were most likely to have been exposed to an infectious disease from direct interaction with a person with a confirmed diagnosis. In addition, the monitoring system may create a report specifying the identities of individuals that did not have direct interaction with the infected person, but who used an area used by the infected person within a defined time period. Similarly, the monitoring system may generate another prioritized list of persons that were most likely to have been exposed to an infectious disease from contact with contaminated surfaces or airborne contamination from a known infected person, based on a determination that they shared the same space (identified by a person's presence within a geofence) within a definable time window (based on infection data, such as infection transmission dynamics and survival duration on surfaces or in the air). The monitoring system may, additionally identify locations where a person with a positive diagnosis spent significant periods of time and the system may update its risk ratings for different areas and, where relevant, any equipment therein, based on this information.

The system may additionally re-calculate risk levels, depending on different factors. For example, a risk level for a person may increase after a detected contact with a higher risk person, equipment, or space. Conversely, a risk factor for a person, equipment, or space may decrease following a recorded completion of a cleaning operation. In some instances, the change in risk factor may depend on a time window before or after a risk-altering event. For example, after high risk contact occurs for a person, the system may record that person performing a hygiene operation within a configurable time window. The risk factor for that person may initially have increased, but is then decreased due to the completion of the sanitation operation within the required time.

Asset Tracking

Figure 8:
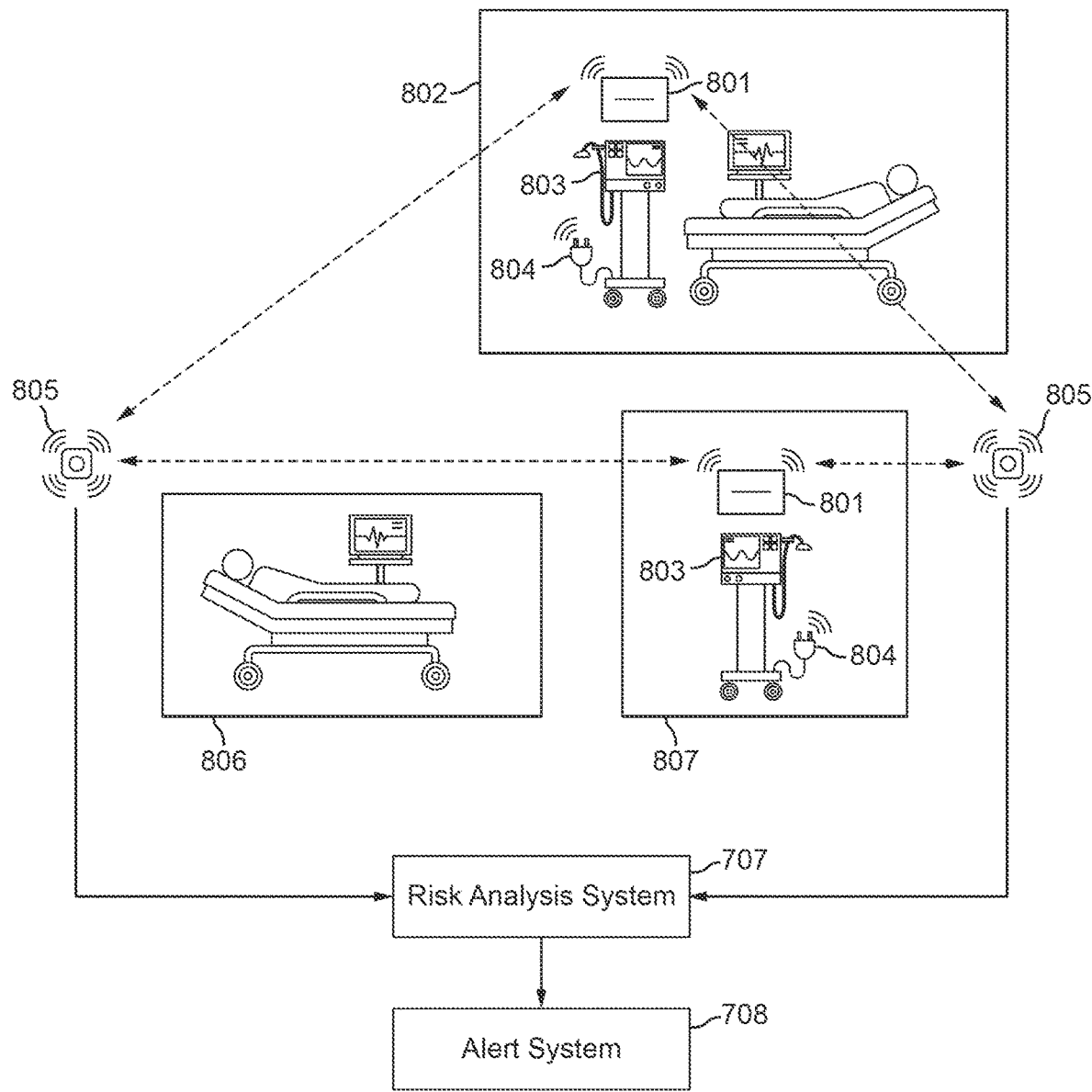
FIG. 8 is a diagram showing a process for monitoring critical mobile assets, according to some embodiments.

Referring now to FIG. 8, a system for monitoring a critical mobile asset (e.g., a ventilator in a hospital) and a means of identifying the asset's availability and a risk assessment of that mobile asset, based on usage and location data for the asset is shown, according to an exemplary embodiment. Usage data may include sensor data indicating interaction of a person with the asset or may include a power consumption 804 data about the asset, indicating that the asset is or has been in use. Mobile asset 803 has a location tag 801 that communicates with stationary transceivers 805 that record the location of the mobile asset 803. The location of the mobile asset 803 may fall within a geofence of an area that has been indicated in the system as being a high risk area for contamination 802. For example, a geofence may be defined within an ad hoc medical facility, such as a field hospital, for dealing with an epidemic and relating to a triage area or a high-traffic area where contamination risk is higher. Alternatively, a geofence may define an area for a critical asset within which the asset must remain 806, and the system may generate an alert 808 upon the asset being detected at a location outside the geofence 807 or, alternatively, the location of the mobile asset 803 not being detected within the required geofence. A change to such asset's risk level may be recorded in the system.

Contact Tracing

One implementation of the present disclosure is a method of retrospectively reviewing contact log information to identify potential transmission or contamination caused by an individual, where that individual has been identified as being infected by a contagion.

In some embodiments, the system can be supplied with the ID of a specific target individual, and a time window. The system then processes log data to identify the spaces, equipment, and other individuals that the target individual came into proximity with, during the set time window. In some embodiments the length of time that the target individual was in proximity to another individual, piece of equipment, or within a space is taken into consideration. Extended periods of proximity may be used to increase a determined risk that infectious transmission or contamination has taken place.

Information relating to the presence of an infected person within a space and the duration of presence may additionally be used by the monitoring system to initiate a targeted decontamination of the relevant areas and equipment, rather than decontaminating a wider area.

In some embodiments, low risk users may be eliminated from an infection risk analysis or a contact tracing history, for a more accurate picture of transmission and a more effective management of social distancing rules, with lower business impact. The system may additionally identify equipment used by an infected person, based on person's location data in respect of location data and/or sensor data of the equipment (e.g., correlating person location with mapped location of equipment, equipment beacon location data, power consumption data indicating equipment is in active use, sensor data indicating interaction of user with equipment, such as opening a refrigeration unit door). The system may use this data to create a prioritized list of equipment that is most likely to have been contaminated by an infected person.

Figure 9:
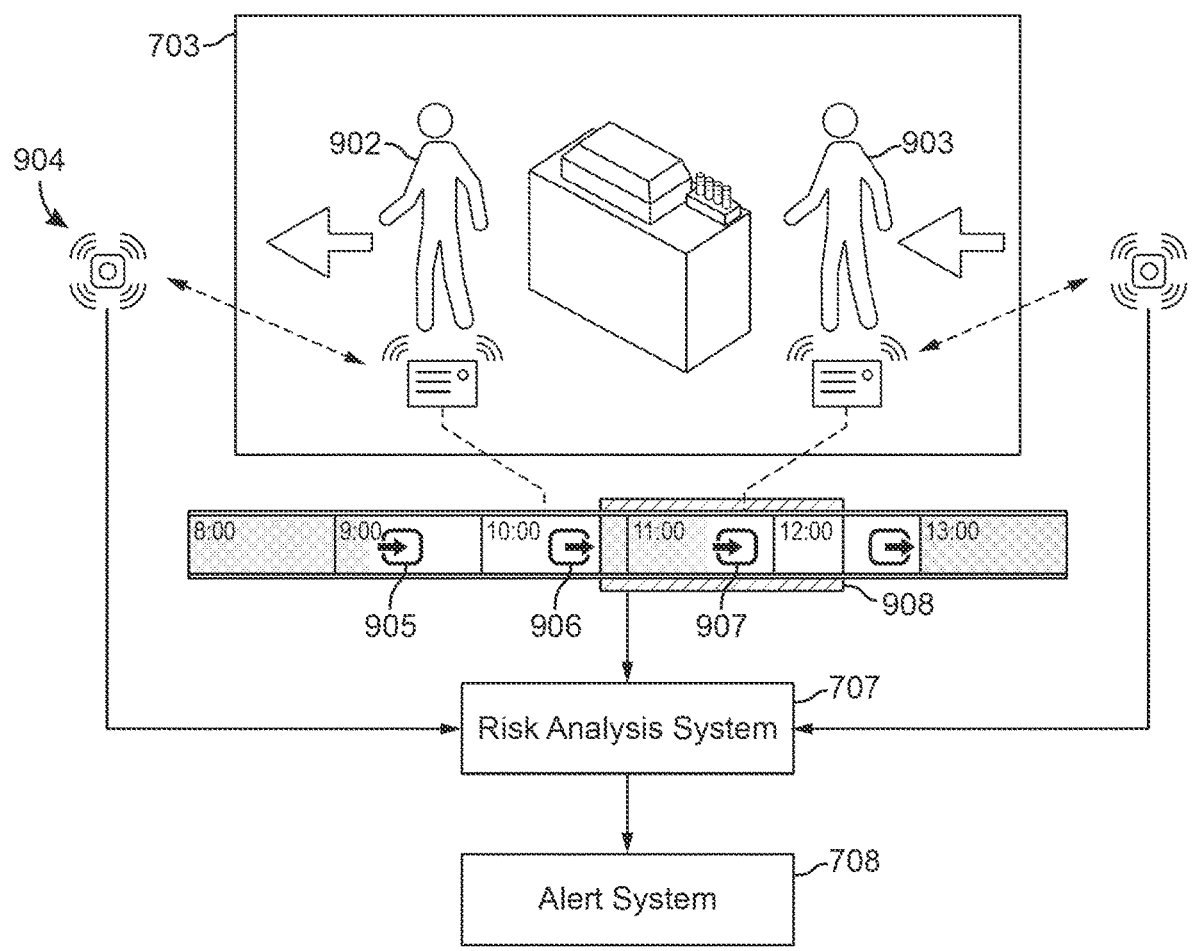
FIG. 9 is a diagram showing a process for detecting a risk of human to surface contamination, according to some embodiments.

Referring now to FIG. 9, a process for detecting a risk of human-to-surface contamination and onward human transmission, using people tracking data, room geofences, and equipment usage monitoring is shown, according to an exemplary embodiment. For example, a person 902 uses a small room for a minimum time period (e.g., more than 15 minutes/1 hour etc.). That person 902 is detected by sensors 904 of occupant tracking system 104 within room geofence 901, and the start time 905 and end time 906 of that presence is recorded. In the same example, a subsequent detection of other persons 903 is made in the same location and that presence is detected to occur 907 within an unsafe time window 908 for contamination risk. Such space and time overlap analyses may be made in respect of desks, laboratories, conference rooms, meeting rooms, or in any shared space whose location or geofence is defined in the system. User risk ratings may change, based on the analysis. Space and associated equipment risk ratings may change, based on the analysis.

Recording Cleaning Events

Figure 10:
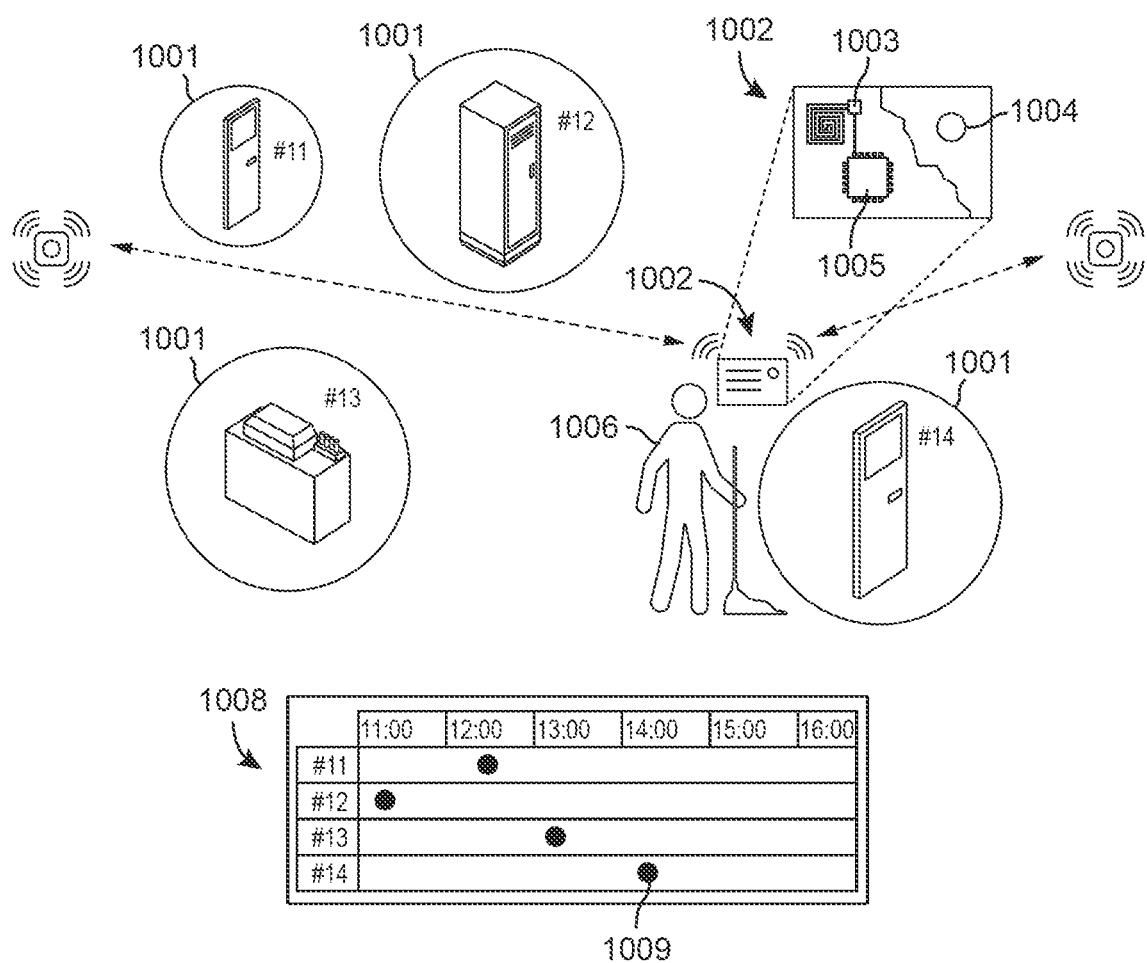
FIG. 10 is a diagram showing a method of recording cleansing operations on a target surface, according to some embodiments.

Referring now to FIG. 10, a method of recording completion of a cleansing operation on a target surface, e.g., a door handle, door plate, equipment, or other surface, in accordance with a cleaning schedule is shown, according to an exemplary embodiment. A special purpose transceiving card 1002 includes a button 1004, which enables a janitor or cleaner 1006 to confirm completion of a cleansing operation. In some embodiments, the button is connected to a microprocessor 1005 and wireless communication circuitry 1003. Pressing the button triggers the microprocessor to transmit the location of the card 1002 to the central system 1008. In such an embodiment, the locations of specific surfaces or general areas 1001 to be cleaned are mapped in system. When the system receives communication from the transceiving card 1002, the system determines the nearest mapped cleaning location 1007 to the current location of the transceiving card 1002, and then associates a cleaning event 1009 with that mapped cleaning location.

In some embodiments, the transceiving card 1002 includes buttons, each of which may have a specific purpose. For example, buttons may be provided to indicate that a nearby door needs cleaning, that the door has been cleaned, or that a hand sanitizer dispenser requires refilling. In some embodiments, to reduce the risk of transferring contagion between a cleaning operative's hand and the transceiving card 1002, the button may be replaced by optical or ultrasonic sensors to detect hand gestures, be automatically triggered by dwell time, or use some other method.

In some embodiments, the logged event of a cleaning operation reduces the risk rating of an area or piece of equipment. In some embodiments, the logged event of a cleaning operation is taken into consideration in the contact tracing process. If a cleaning operation is logged in an area that was previously used by an individual that is a contagion risk, then the risk is reduced for any individuals that use the area after the cleaning operation. However, the cleaning operative themselves may still be determined to be at high risk from the contagion.

Alternatively, the signal from the transceiving card 1002, triggered by the press of a button or other method, may indicate that an area requires cleaning. For example, an individual may recognize that they have not adequately contained a sneeze or a cough, and then use their transceiver badge to request that an area be cleaned. The system may also be used to report events such as spillages.

Hand Hygiene Monitoring and Sanitation Consumables Monitoring

In some embodiments, a hygiene and sanitation support system may ingest data from connected hand sanitizer dispensers. Said hand sanitizer dispensers may include a sensor to determine remaining levels of hand sanitizer, microprocessor, and wireless communication circuitry. If a hand sanitizer dispenser senses that it is empty, then it may communicate that status to a central system. A user interface may then show the location of hand sanitizer dispensers that require filling on a system map view and an SMS or other notification may be sent to an appropriate individual. Additionally, person tracking system may be used to determine the nearest janitor or cleaner in the vicinity of a dispenser requiring refilling and an alert may be sent to that person's cellphone.

In some embodiments, a user may be able to manually request that a hand sanitizer dispenser be refilled. In embodiments where users carry a transceiving card, and where that card can be activated to send a cleaning request, the triggering of such a cleaning request while in close proximity with a hand sanitizer dispenser may be interpreted as a request to refill said hand sanitizer dispenser.

In some embodiments, a social distancing analysis system may ingest data from connected hygiene monitoring equipment and update the risk rating of a user based on a determination for a user of a failure to comply with correct hygiene procedures. The hygiene equipment may be a hand sanitizer dispenser, where the procedure may simply be use of the equipment. The hygiene equipment may be a hand hygiene monitoring sensor, where the procedure may relate to appropriate duration and/or motions for hand washing. In some embodiments, the system may send an SMS notification when a card passes some area without triggering the required hygiene equipment.

User Interface Output

A user interface for the outputs of the disclosed systems and methods may include various embodiments, such as a map or floorplan of the monitored area overlaid with geofenced boundaries of individual spaces, the mapped locations of stationary equipment or current locations of mobile equipment, the locations of people or events, which may be indicated by icons, heat maps, etc. A user interface may display indications of contamination hotspots, risk ratings for people, equipment, or spaces, or infected person trails, with time and risk information. Alerts may displayed for equipment in a high risk area or cleaning alerts.

Simulating the Spread of Contagions

One implementation of the present disclosure is a method to simulate the spread of a contagion based on historical data, live data, or predicted data.

In some embodiments, simulating the spread of contagion using historical data shares some of the features described for running contact tracing reports. Parameters can be adjusted for each simulation, such as the percentage chance of transmission, how the chance of transmission increases as the length of exposure time increases, the incubation period, the period of communicability, and at what stage the individual may stop attending work due to the illness. One or more individuals may be selected as the source of the contagion. The potential spread of the contagion can then be simulated based on the historical data of person-to-person interactions, potential person-to-surface to person transmissions, cleaning events, and any other relevant recorded data. Additional events may be interjected during the simulation, such as selecting another individual to be a source of contagion, adding cleaning events, and simulating sending an employee home by ignoring their interactions after a set point in time.

In some embodiments, simulating the spread of contagion is run on predicted data. Machine learning models may be trained on historical data, and then used to simulate the behavior of occupants. This enables interventions that were not present in the historical data, such as restricting the spaces that certain occupants can visit and reducing maximum occupancy limits for rooms.

In some embodiments, simulating the spread of contagion is run in real-time. Parameters can be adjusted in advance of or during the simulation, as described for running simulations on historical data. The potential spread of the contagion is then simulated based on the live data of person-to-person interactions, potential person-to-surface to person transmissions, cleaning events, and any other relevant data. In a live simulation, the effect of interventions such as reducing maximum occupancy limits for rooms and providing guidance to occupants can be observed, rather than a simulated ideal. For example, occupants may not follow guidelines or there may be unexpected consequences, such as restrictions in one area leading to increased occupancy in other areas.

Reports may be run on the results of simulations or on historical data to identify individuals that had the most person-to-person contacts within a given time window, individuals that visited the largest number of separate locations, or to identify other information that is useful in anticipating the spread of a contagion.

Figure 11:
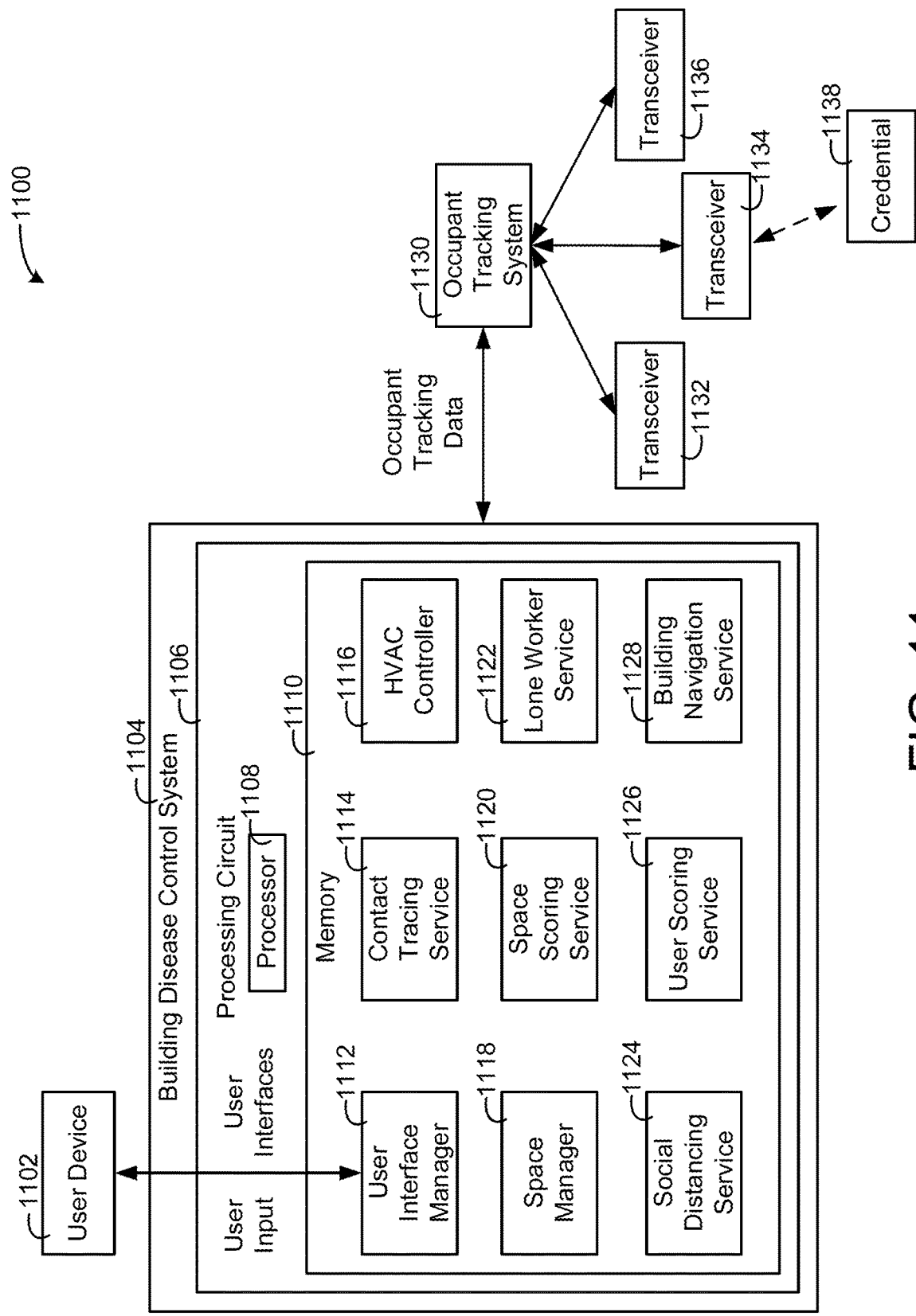
FIG. 11 is a block diagram of a building disease control system that facilitates social distancing and contact tracing for a building, according to some embodiments.

Referring now to FIG. 11, a system 1100 including a user device 1102, a building disease control system 1104, and an occupant tracking system 1130 is shown, according to some embodiments. The building disease control system 1104 can facilitate social distancing and contact tracing for a building based on occupant tracking data received from the occupant tracking system 1130 and cause the user device 1102 to display user interfaces based on the occupant tracking data.

The building disease control system 1104 includes a processing circuit 1106 that includes a processor 1108 and a memory 1110. The processor 1108 can be implemented as a general purpose processor, an application specific integrated circuit (ASIC), one or more field programmable gate arrays (FPGAs), a group of processing components, or other suitable electronic processing components.

The memory 1110 (e.g., memory, memory unit, storage device, etc.) can include one or more devices (e.g., RAM, ROM, Flash memory, hard disk storage, etc.) for storing data and/or computer code for completing or facilitating the various processes, layers and modules described in the present application. The memory 1110 can be or include volatile memory or non-volatile memory. The memory 1110 can include database components, object code components, script components, or any other type of information structure for supporting the various activities and information structures described in the present application. According to an exemplary embodiment, the memory 1110 is communicably connected to the processor 1108 via processing circuit 1106 and includes computer code for executing (e.g., by processing circuit 1106 and/or the processor 1108) one or more processes described herein.

In some embodiments, the building disease control system 1104 is a cloud based system (e.g., AZURE, AMAZON WEB SERVICES, etc.) that can be integrated with existing or newly installed building systems (e.g., the occupant tracking system 1130). In this regard, the building disease control system 1104 can operate agnostic to the physical infrastructure of a building. This allows the building disease control system 1104 to operate based on any occupant tracking sensors that are already in place in the building to provide insights that were not previously available. The building disease control system 1104 can be a plug and play wire-free installation, integrating diverse sensor information in a cloud based solution.

The occupant tracking system 1130 can collect data from transceivers 1132-1136. The transceivers 1132-1136 can be wireless beacons distributed through various areas of a building. When a credential 1138 of a building occupant is within range of one of the transceivers 1132-1136, the transceiver 1134, the occupant tracking system 1130 can identify the occupant through the credential 1138. The location and identity of the occupant, as determined through the particular beacon that sensed the credential 1138 and a unique identifier associated with the credential 1138, can be included in the occupant tracking data. The credential 1138 could be a badge of the occupant, a mobile device of the occupant, a smartphone, a smartwatch, etc. The occupant tracking system 1130 is described in greater detail with reference to FIGS. 13A-13B.

The memory 1110 includes a user interface manager 1112. The user interface manager 1112 can generate user interfaces that include social distance monitoring reports generated by social distancing service 1124, contact tracing reports generated by contact tracing service 1114, and an indication of targeted areas for decontamination identified by space manager 1118. The interfaces can include reports, graphs (e.g., pie charts), and/or data for social distancing and/or contact tracing. Furthermore, the interfaces can include a heat map visualization tool showing high occupant usage spots that indicate places at higher risk for infection transmission. Furthermore, the interfaces can indicate whether an occupant is planning on using a space, whether the space is cleaned or not, etc.

Furthermore, the user interface manager 1112 can generate occupant engagement interfaces. The occupant engagement interfaces can indicate spaces availability and readiness for reserving a work space, e.g. hot desking. In some embodiments, the system can schedule hot desking for users that properly space users to comply with social distancing policies. For example, the system can space occupants out at every other desk. The interfaces can allow occupants to reserve meeting rooms. In some embodiments, the interfaces provide wayfinding and navigation recommendations based on the operations of the building navigation service 1128.

In some embodiments, the user interface manager 1112 generates a personal dashboard that indicates social distancing scores for an occupant and/or social distancing notifications indicating whether the occupant has violated a social distancing policy. Furthermore, the interfaces can include occupant facing live space views, behavior feedback/scoring, badging, etc.

The memory includes contact tracing service 1114. The contact tracing service 1114 can generate contact tracing reports based on the occupant tracking data. The report can include indications of the time duration of encounters between occupants. For example, the report could indicate occupants that an infected person have encountered over a particular timeframe and the location of each encounter. Furthermore, the report can indicate individuals at highest risk of potentially contracting an infectious disease based on commonly visited spaces that have also been visited by an infected person.

The contact tracing service 1114 can determine occupants that interact with each other as well as locations (e.g., the spaces) that the occupants spend time within. Based on the occupant tracking data, the contact tracing service 1114 can register badge activity within spaces of various occupants, record contacts made between occupants (e.g., the time and duration of each contact), track the compliance of occupants in real-time, etc.

The contact tracing service 1114 can generate a report for scenario planning by including contact tracing of a group or all occupants of a building, e.g., all employees of a facility. The contact tracing service 1114 reports can assist crisis management teams in order to facilitate proactive monitoring and/or response to an event, e.g., the spread of a disease. For example, if an occupant tests positive for an infectious disease, the contact tracing service 1114 can indicate other occupants who have had prolonged contact with their infected occupant and those who would have occupied potentially contaminated areas. In a commercial setting, the contact tracing can reduce the anxiety of employees.

The contact tracing service 1114 can minimize the number of occupants that need to self-isolate and avoid the need to close a building and/or a floor of a building by tracking the occupants and their interactions within the building. The reports generated by the contact tracing service 1114 can indicate impacted spaces and/or occupants. In some embodiments, the contact tracing service 1114 can quantify a level of risk for each occupant and/or for various spaces based on exposure and/or duration of exposure that the occupant and/or space has had to an infected individual.

In some embodiments, the contact tracing service 1114 can manage risk through screening visitors of a building. For example, the contact tracing service 1114 can determine, based on occupant information, whether the visitor poses a threat risk to occupants of the building. The information may indicate the organization that the visitor is associated with, whether the occupant has tested positive or negative for a disease, whether the visitor has been in a high infection level geographic area, etc.

In some embodiments, in response to receiving a positive diagnosis that a building occupant has contracted an infectious disease, the contact tracing service 1114 can generate a notification for the occupant to immediately leave the building and provide another notification to a human resources (HR) system indicating that the occupant has been infected. The contact tracing service 1114 can initiate a contact trace for the infected occupant and determine what other occupants came into recent and close contact with the infected occupant. A list of high risk occupants, occupants that have come into contact with the infected occupant, can be provided by the contact tracing service 1114 to the HR system.

In some embodiments, the HR system may receive a notification from an occupant that the occupant has been infected with an infectious disease. The HR system can send an indication to the contact tracing service 1114 to identify the infected individual. The contact tracing service 1114 can, in response to the indication, execute a contact trace of the individual to understand the scope of risk posed by the individual, e.g., identify the number of occupants that the individual has come into contact with. The contact tracing service 1114 can generate a notification for each occupant that has come into contact with the infected individual notifying the individual that they have been exposed to an infected individual and provide response support.

In some embodiments, the contact tracing service 1114 can store a contact tracing history of contact tracing data, e.g., a historical indication of encounters between occupants. The contact tracing service 1114 can be configured to search the contact tracing history to see how much time occupants have been in contact infected occupants to derive a probability of each occupant being infected.

In some embodiments, the contact tracing service 1114 can perform a multi-level trace that can reveal if a person is asymptomatic that could be the cause of infection at a building. The contact tracing service 1114 can identify potential asymptomatic occupants and flag the occupants for testing. The contact tracing service 1114 can, for example, look at varying levels of interactions between occupants to trace an infectious disease between occupants. The contact tracing can look at a window of fifteen minutes to identify whether two occupants have come into contact for a sufficient amount of time that a disease may be have been transmitted. In some embodiments, the window is variable can be set or adjusted by a user to look at various different contact tracing outputs, e.g., different indications of potential occupants that should be tested.

The contact tracing service 1114 can automatically monitor social distancing performance across a building and generate a measure of risk of various spaces or occupants, an indicator of the likelihood of infectious disease transmission in the space and/or resulting from interactions with the occupants. The contact tracing service 1114 can provide contact tracing to surface all the occupants that had prolonged close contact with the infected person and well as run scenario analysis to highlight the occupants who have the greatest potential to infect others be it in their social distancing performance or variety of use of spaces within the building.

The HVAC controller 1116 can receive contact tracing based data and make environmental control decisions for an HVAC system based on the contact tracing data. For example, the HVAC controller 1116 can operate the building based on heat map data generated by the contact tracing service 1114. The HVAC controller 1116 can identify areas of a building with poor social distancing performance, e.g., high occupant density areas. The HVAC controller 1116 can increase air flow to high occupant density areas or surrounding areas of the building.

The HVAC controller 1116 can receive a contact trace from the contact tracing service 1114 that indicates that a particular number of occupants have contracted an infectious disease from one another. The contact trace can indicate the locations where the occupants have been located within the building. The HVAC controller 1116 can schedule cleaning and/or sanitization of the spaces where the infected occupants have been present. In some embodiments, the HVAC controller 1116 can operate disinfection light sources that generate light (e.g., ultraviolet, near ultraviolet, etc.) that kills a viruses and/or bacteria in the spaces. Furthermore, the HVAC controller 1116 can operate the HVAC system to pull in fresh outdoor air for the spaces and/or exhaust air from the spaces. The heat map generated by the contact tracing service 1114 can include risk levels for each space which can be reduced to lower levels once the HVAC controller 1116 finishes sanitizing the spaces. In some embodiments, the HVAC controller 1116 can receive indications of high potential areas of a building that an infectious disease may be transferred. The HVAC controller 1116 can take a proactive control operations to reduce the chance of disease transfer in the high risk areas.

The HVAC controller 1116 can operate spaces based on characteristics of the occupants of the spaces. For example, the contact tracing service 1114 can identify various characteristics of a tracked occupant within the space. The characteristics could be a sensitivity rating, a risk level of the occupant (e.g., a low risk of complications from an infectious disease, high risk of complications, etc.), etc. In response to receiving an indication of an occupant that has a high risk of infection, the HVAC controller 1116 can perform custom environmental control of the spaces that the occupant is present to reduce the likelihood that the occupant will contract the disease. For example, the HVAC controller 1116 could increase air turns for the space, increase a percentage of fresh outdoor air, utilize air pulled through a disinfection light kill tunnel of an air duct, etc.

In some embodiments, the HVAC controller 1116 can operate environmental spaces of a building based on occupant preferences. Some or all of the occupants could be associated with an ideal temperature set point. The HVAC controller 1116 can be configured to determine temperature or other environmental conditions based on the preferences of the occupants located in the spaces. The HVAC controller 1116 can learn predicted locations for occupants within the spaces by analyzing movement patterns of occupants received from an occupant tracking system. The HVAC controller 1116 can operate spaces preemptively to condition the space to a level preferred by the occupant. The HVAC controller 1116 can further preemptively control the environmental conditions of the space to reduce the spread of disease in areas that a high risk occupant is predicted to be located within.

The memory 1110 includes a space manager 1118. The space manager 1118 can be configured to ensure highly utilized spaces are cleaned frequently by scheduling cleaning times for highly utilized spaces. The space manager 1118 can receive an indication of the spaces that have high occupant tracking or the locations that an infected individual has been present in from the contact tracing service 1114.

The space manager 1118 can be configured to identify target areas of a building for decontamination and/or times for the target areas to be decontaminated. The space manager 1118 can be configured to assign one or more cleaning personnel to perform the decontamination. In some embodiments, the decontamination can be performed by building systems, e.g., bringing in outdoor air, releasing decontamination gases, activating disinfection lighting in particular areas of the building, etc. The user interface manager 1112 can be configured to generate a user interface indicating that the target areas for decontamination, the times for decontamination, and/or the personnel assigned to perform the decontamination.

In some embodiments, the space manager 1118 can be configured to identify the locations, durations, and start times of spaces that an occupant has visited in response to the occupant testing positive for a disease. The space manager 1118 can be configured to identify the locations that the infected occupant has been present in. The space manager 1118 can be configured to schedule targeted cleaning for those spaces and generate an indication of cleaning once the spaces have been cleaned.

In some embodiments, the space manager 1118 can be configured to assign a level of cleaning to various areas of a building. For example, the levels of cleaning could be no cleaning, light cleaning, heavy cleaning, and/or deep cleaning. Based on how long occupants have spent time in each area and/or whether the occupants were infected can be used by the space manager 1118 to determine the cleaning level for the spaces. By applying the specific cleaning level, cleaning resources can be preserved for the building since spaces are only cleaned when needed.

In some embodiments, the space manager 1118 provides an indication of what spaces have or have not been cleaned to the user interface manager 1112. The space manager 1118 can generate a user interface that indicates what spaces have been cleaned, when the spaces have been cleaned, and/or what level of cleaning was performed on the spaces. This user interface can be viewed by occupants of the building in order to understand what spaces have been cleaned to reassure employees that the spaces of the building that they may use are not contaminated and have a low risk of exposing the occupants to an infectious disease. In some embodiments, the interface can include a sanitization status for each space, an occupancy density for each space, and/or a wellness score for each space and/or each asset within a space (e.g., table, desk, bubbler, vending machine, computer, etc.).

In some embodiments, the space manager 1118 can generate a work schedule for employees at a building that staggers start times to avoid congestion at a clock in location of the building. If a group of users all started their work at the same time, they would all need to utilize the clock-in location at once. However, staggering the clock-in times of employees avoids the congestion. In some embodiments, a clock-in user interface can be generated by the user interface manager 1112 and displayed by the user device 1102. A user can clock-in via the user interface instead of congregating at a physical clock-in system.

The memory 1110 includes a space scoring service 1120. The space scoring service 1120 can be configured to generate a safety level score for spaces of a building. The safety score can indicate the likelihood of the spread of an infectious disease to occupants within the space. The safety score can be determined by the space scoring service 1120 based on various factors that relate to the spread of the infectious disease within the space. The score can be generated for a campus, a building, and/or spaces within the building.

The memory 1110 includes a lone worker service 1122. The lone worker service 1122 can detect, based on contact tracing and occupancy tracking data received from the contact tracing service 1114, that an occupant of the building is alone in a building. For example, for a commercial building, one employee may be isolated from other employees. Because spaces of a building may be underutilized in view of social distancing practices, an employee of a building can become unattended and alone within the building while working. The lone worker service 1122 can be configured to identify, based on the occupant tracking data (e.g., received from the contact tracing service 1114 and/or the occupant tracking system 1130), that there are no other occupants within a particular area of the occupant for a particular amount of time.

In response to detecting a lone worker, the lone worker service 1122 can be configured to contact human resources, security, employee health services, a supervisor of the lone worker, etc. The lone worker service 1122 can generate a notification (e.g., an email, a text message, an application notification, etc.) and serve the notification to the user device 1102. These notifications can cause a user to provide duress support to the lone worker (e.g., asking other workers to work nearby the lone worker) to improve the wellbeing of the lone worker.

The memory 1110 includes a social distancing service 1124. The social distancing service 1124 can be configured to monitor and track the compliance of occupants with social distancing practices based on the occupant tracking data received from the occupant tracking system 1130. In some embodiments, the social distancing service 1124 can monitor the compliance in real. The social distancing service 1124 can be configured to determine, for a space of the building (e.g., workspaces such as desk spaces, meeting rooms, collaboration areas), whether the number of occupants within the space have exceeded a particular number. The particular number may be based on an area of the space.

In response to a determination that there has been a social distancing violation, the social distancing service 1124 can be configured to generate a notification of the violation and/or indicate corrective actions to correct the behavior that is violating the social distancing violations. The notification can be served to the user device 1102. In some embodiments, the notification is sent to user devices of one or more occupants that are violating the social distancing policy. In some embodiments, the notification is served to a facility manager, a human resources individual, building security, etc.

In some embodiments, in response to detecting a social distancing violation, the social distancing service 1124 can provide an indication to the contact tracing service 1114 to initiate a contact trace of occupants that have violated a social distancing policy. Furthermore, in some embodiments, the social distancing service 1124 can generate a list of occupants that have been affected by a violation of a social distancing practice.

In order to ensure that a building is safe, the social distancing service 1124 can perform automated social distancing monitoring to help employees achieve best practice in social distancing behaviour and help minimise the impact of any contact tracing reports. Although social distancing may be hard to physically enforce, the monitoring and notification generation performed by the social distancing service 1124 can help motivate improvements to social distancing behaviour and improve the compliance of social distancing in various areas of a building. Furthermore, the presence of the notifications and monitoring can help reassure employees that their work environment adheres to high social distancing practices.

In some embodiments, the social distancing service 1124 can improve communication between occupants with respect to social distancing practices since the social distancing service 1124 can provide a comprehensive report. In some embodiments, the report can be requested by one of the occupants via the user device 1102. Furthermore, because the tracking and analysis can be performed in real-time by the social distancing service 1124, the alerts provided to the occupants that are violating a social distancing practice can also be generated and received in real-time. The notifications could further notify occupants of high occupancy hot spots in real time. This can help improve social distancing in real-time within a building. The notifications can further identify spaces where social distancing is a problem in order to help occupants and/or building personnel improve the performance of the spaces.

In some embodiments, the social distancing service 1124 can generate a notification indicating that an occupant has violated a social distancing practice. The occupant can receive the notification via the user device 1102. The alert can provide the occupant with guidance to improve their behavior. In response to reading and acting on the guidance, the social distancing performance of the occupant and the space where the occupant is located can improve.

In some embodiments, the social distancing service 1124 can provide occupant specific social distancing scores. The scores can indicate the frequency at which the occupant violates social distancing practices. For example, users may be given scores based on the number of social distancing violates the users receive for a particular historical window.

The memory 1110 includes the user scoring service 1126. The user scoring service 1126 can be configure to generate a score for a user, an occupant of a building, based on various factors that relate to the spread of an infectious disease associated with the user and the health of the user. The factors can indicate social distancing practices performed by the user as identified by the social distancing service 1124, e.g., the number of times that the user has violated a social distancing practice. Furthermore, the factors can indicate whether or not the occupant has come into contact with infected individuals. Furthermore, the factors can indicate the health of the occupant, e.g., age, medical conditions, etc. Generating the user score for a user is described in greater detail with reference to FIG. 14.

The memory 1110 includes a building navigation service 1128. The building navigation service 1128 can be configured to perform navigation for an occupant or visitor of a building. For example, the building navigation service 1128 may store various maps with indications of locations of specific areas of the building. The building navigation service 1128 can receive a location of an occupant and a destination of the occupant and perform a wayfinding algorithm that identifies a path for the occupant from the location to the destination.

Figure 26:
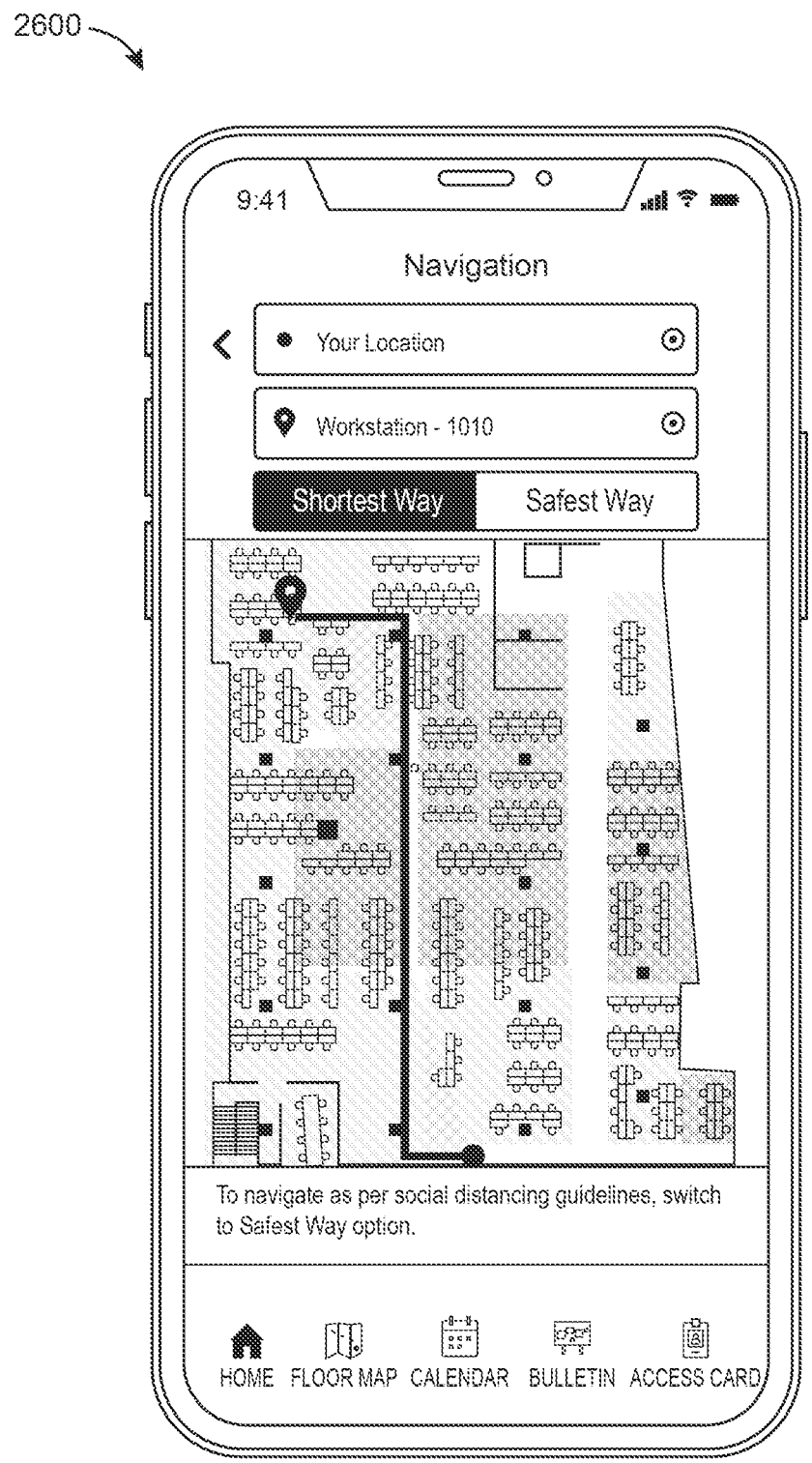
FIG. 26 is a schematic diagram of a navigation screen of the building disease control system of FIG. 11, according to an exemplary embodiment.

The building navigation service 1128 can further receive indications of high occupant use spaces and/or indications of spaces that an infected individual has recently been present. The building navigation service 1128 can generate a path from the location to the destination that avoids the dangerous areas of the building. In some embodiments, a user, via the user device 1102 specifies a level of risk that the user is willing to take. Accordingly, the building navigation service 1128 can generate a path from the location to the destination that avoids or passes through dangerous area so of the building based on the level of risk that the user is willing to take. An exemplary interface that the user interface manager 112 is configured to generate of the building navigation service 1128 is shown in FIG. 26.

Figure 12:
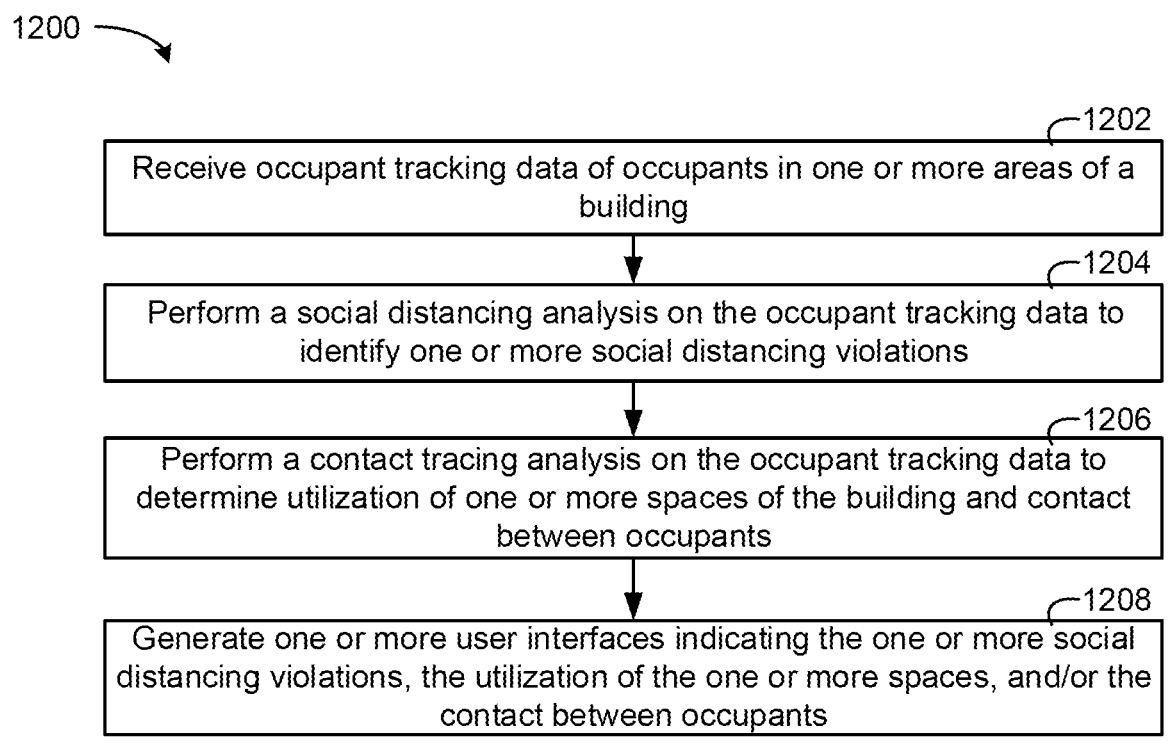
FIG. 12 is a flow diagram of a process of performing social distancing analysis and a contact tracing analysis based on occupant tracking data of a building, according to an exemplary embodiment.

Referring now to FIG. 12, a flow diagram of a process 1200 of performing social distancing analysis and a contact tracing analysis based on occupant tracking data of a building, according to an exemplary embodiment. The process 1200 can be performed by the building disease control system 1104 and/or the occupant tracking system 1130. In particular, the process 1200 can be performed by the contact tracing service 1114, the social distancing service 1124, and the user interface manager 1112. Any computing device or system as described herein can be configured to perform the process 1200.

In step 1202, the building disease control system 1104 can receive occupant tracking data from the occupant tracking system 1130. The occupant tracking system 1130 can record identifiers associated with users, e.g., the credential 1138 when the credential 1138 is close to one of multiple different beacons, e.g., the transceivers 1132-1136. The occupant tracking system 1130 can aggregate the credential information received at the transceivers 1132-1136, each which may be located with a particular space of the building, and report the data to the building disease control system 1104.

In step 1204, the social distancing service 1124 can perform a social distancing analysis on the occupant tracking data to identify one or more social distancing violations. The social distancing service 1124 can identify that multiple occupants have been within a particular proximity for a particular amount of time, indicating that the multiple occupants have caused a social distancing violation.

For example, each space of a building may be associated with various beacons, e.g., the transceivers 1132-1136. Each space may be a particular area. The social distancing service 1124 can store the indication of each area of each space. The social distancing service 1124 can determine an appropriate level of occupancy for each space and determine if the occupancy of the space exceeds the appropriate level. If the level is exceeded, the social distancing service 1124 can generate a social distancing violation and associate the violation with the occupants.

In step 1206, the contact tracing service 1114 can perform a contact tracing analysis on the occupant tracking data to determine utilization of one or more spaces of the building and contact between occupants. The contact tracing service 1114 can determine a utilization of spaces and track which spaces are highly utilized, i.e., have a particular number of occupants within the space at a particular point in time and/or determine an average number of occupants within the space over a time period. This can allow the contact tracing service 1114 to determine which spaces of a building are highly utilized for the purposed of navigation, cleaning, etc.

Furthermore, the contact tracing service 1114 can identify and track contact between occupants based on the occupant tracking data. For example, if two occupants are both located within a space for at least a particular amount of time, the contact tracing service 1114 can identify that the two occupants have come into contact. The contact tracing service 1114 can record the identities of the occupants, the time at which the occupants came into contact, the duration of the contact, and the location where the occupants came into contact.

The contact tracing service 1114 can identify the likelihood of occupants being infected with an infectious disease based on contact that the occupants have with each other and infected individuals. For example, if within a time period a first occupant has come into contact with a second occupant and the second occupant has come into contact with an infected individual, the system can determine likelihoods that the first and second occupants also have the infectious disease. Furthermore, the contact tracing service 1114 can identify an occupant that may be infected with a disease and is spreading a disease but does not exhibit any symptoms, i.e., the occupant does not know they are sick. For example, within a particular amount of time of coming into contact with a first occupant one or more second occupants become sick, the contact tracing service 1114 can flag the first occupant as needing testing.

In step 1208, the user interface manager 1112 can generate one or more user interfaces indicating the one or more social distancing violations, the utilization of the one or more spaces, and/or the contact between occupants. The one or more user interfaces can illustrate the data generated by the social distancing service 1124 and/or the contact tracing service 1114 with charts, graphs, tables, text, audio output, and/or any other data format. The user interface manager 1112 can provide the user interface to the user device 1102.

Figure 13A:
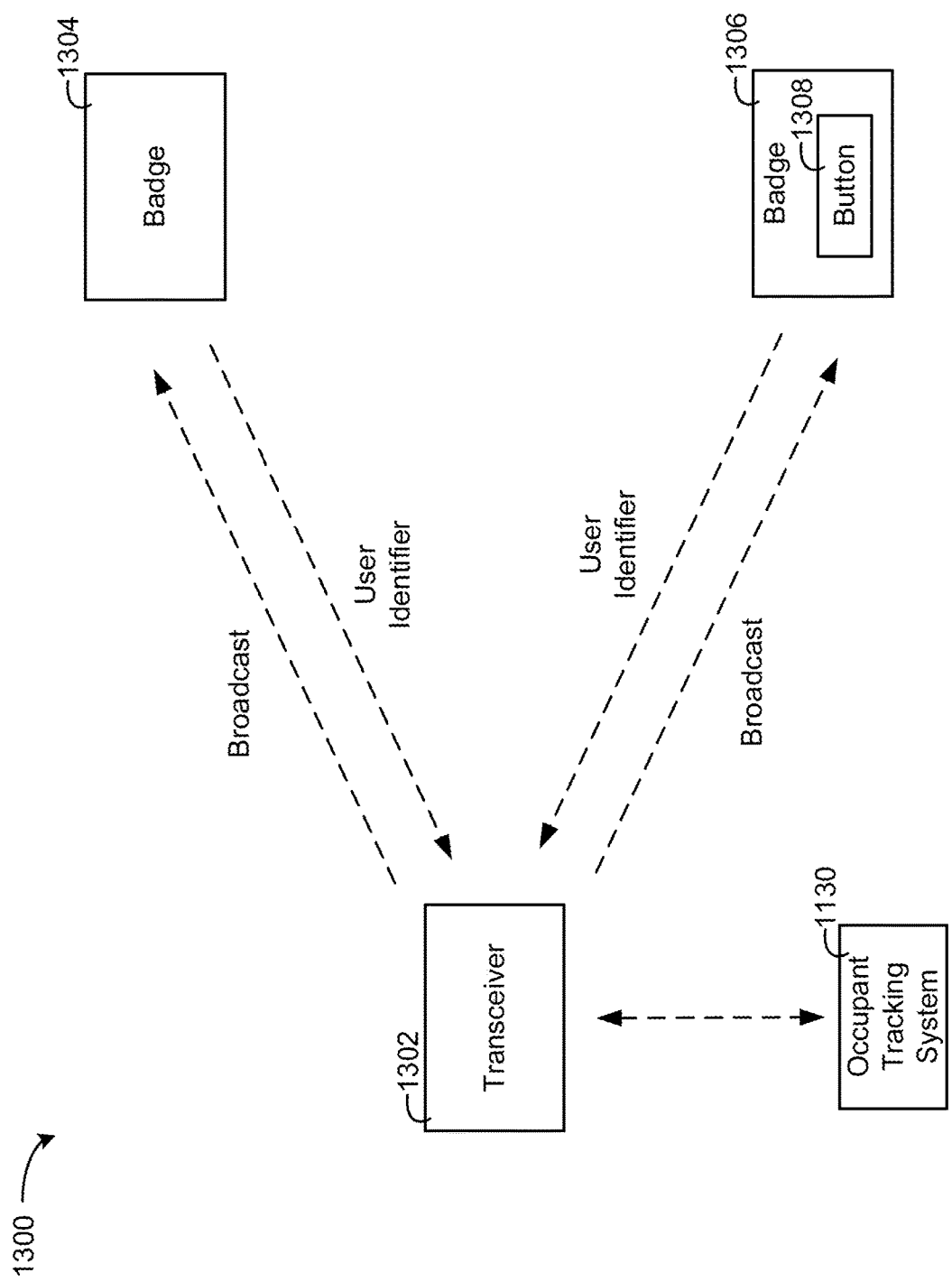
FIG. 13A is a schematic diagram of a transceiver communicating with badges of users to perform occupant tracking in a building, according to an exemplary embodiment.

Referring now to FIG. 13A, a system 1300 including of the transceiver 1302 communicating with badges 1304 and 1306 of occupants to perform occupant tracking in a building, according to an exemplary embodiment. The system 1300 includes the transceiver 1302 broadcasting a wireless signal to the badges 1304 and 1306 and receiving a user identifier from the badges 1304 and 1306. The badges 1304 and 1306 may include a power source, e.g., a battery, that enables the badges 1304 and 1306 to communicate with the transceiver 1302.

The transceiver 1302 and the badges 1304 and 1306 can communicate via low power wireless communication. For example, Bluetooth Low Energy (BLE) or another low energy communication protocol. Bluetooth enabled devices for accurate movement and location individuals in spaces. Although the system 1300 is described as with a transceiver that communicates with access cards of a building, the 1300 could similarly generate occupant tracking data with 5G based cell phone location, cell phone to cell phone communication, Time of Flight (ToF) via Wi-Fi based on cell phone Wi-Fi communication, trilateration and/or triangulation from multiple routers, etc.

The transceiver 1302 can be a wire-free plug that plugs into a power outlet (e.g., AC power outlet) of a building. The transceiver 1302 can be powered via the power outlet and communicate with the badges 1304 and 1306 (e.g., via BLE) and with the occupant tracking system 1130 (e.g., via a local Wi-Fi network). In some embodiments, the transceiver 1302 is a wire-free plug that can be quickly installed by a building technician. In some embodiments, the transceiver 1302 can be a device located within a space that includes one or more wires and/or is battery powered.

The badges can be anonymized through the identifier and therefore do not include any personal information (e.g., name, age, employment position, etc.) for each occupant. The building disease control system 1104 can be configured to perform a lookup with the identifier to identify the identify of each occupant based on the identifier associated with each occupant.

The badge 1308 can include duress support button 1308. The button 1308 can enable an occupant to indicate that they are in danger or need help. The badge 1306 can transmit a duress signal to the transceiver 1302 which can be passed on to the building disease control system 1104 to notify a response person of the location of the occupant of the badge 1306. The duress button 1308 can provide a panic alerting solution that prevents threats from escalating to dangerous events, and provides their location and timestamp.

The system 1300 can enable the contact tracing service 1114 and the social distancing service 1124 to perform a contact tracing service and perform a social distancing analysis. The building disease control system 1104 can store floor plans that include various areas within the building and the association of each transceiver with a particular area. The building disease control system 1104 can generate geofences associated with the various areas and track whether occupants are present within each geofence for contact tracing and social distancing purposes.

Figure 13B:
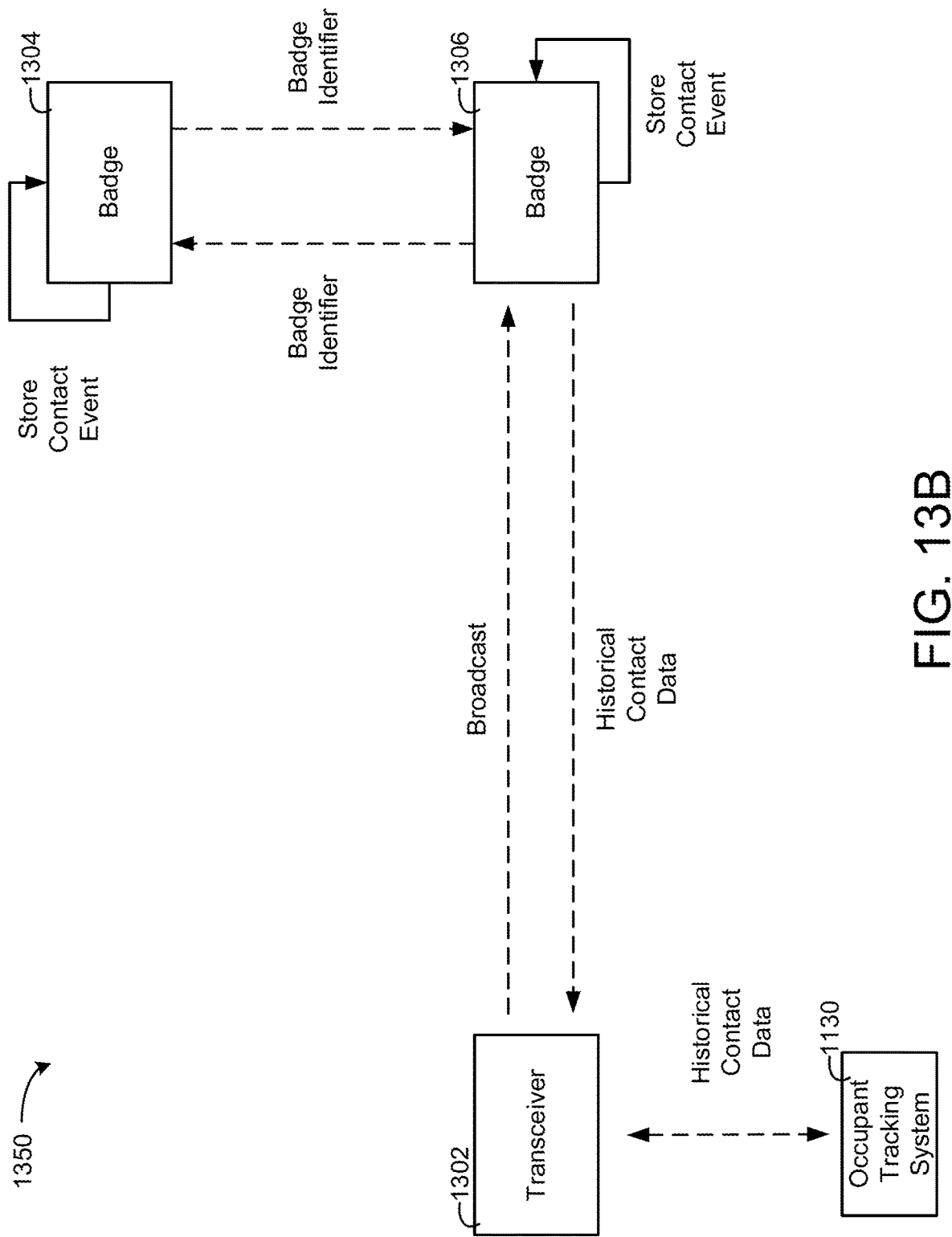
FIG. 13B is a schematic diagram of a transceiver communicating with badges of users that communicate with each other to perform occupant tracking in a building, according to an exemplary embodiment.

Referring now to FIG. 13B, a schematic diagram of a system 1350 including the transceiver 1302 communicating with the badges 1304 and 1306 of users that communicate with each other to perform occupant tracking in a building, according to an exemplary embodiment. In the system 1350, the badges 1304 and 1306 communicate to each other wirelessly ad-hoc (e.g., via Bluetooth, RFID, and/or any other radio communication protocol via one or more radios, transceivers, and/or processing circuits). Furthermore, the transceiver 1302 and/or the badges 1304 and 1306 can also communicate wirelessly ad-hoc. The transceiver 1302 can communicate with the occupant tracking system 1130 via a network, e.g., a Wi-Fi network, a cellular network, etc.

The badges 1304 and/or 1306 can broadcast a message including a badge identifier. The broadcast, when sensed by another badge, can be recorded as a contact event. For example, responsive to the badge 1306 sensing a wireless signal including a badge identifier of the badge 1304, the badge 1306 can store a contact event in a memory device of the badge 1306 (e.g., in RAM, ROM, a hard drive, or any other type of memory device described herein). The contact event can be recorded when the badges 1304 and 1306 are within a set distance (e.g., 6 feet, 3-4 feet if occupants are wearing masks and gloves, etc.), when a signal strength between two badges is greater than a particular amount, or a time of flight of a signal transmitted between two badges is less than a particular amount. Communication between the badges 1304 and/or 1306 that does not meet the set distance, signal strength, or time of flight can be ignored and no contact event recorded. The set distance can be configured by a user. The distance selected by the user can be used to calculate a time of flight time or signal strength level for determining whether a contact event has occurred. The contact event can be recorded based on signal strength, time of flight, near field magnetic indication (NFMI) techniques, etc. NFMI may have accurate distance measurements between NFMI devices on short distances, e.g., 1 foot to twelve feet.

In some embodiments, the contact event stored by the badges 1304 and/or 1306 can indicate contextual information describing the contact event. For example, the event can include the identifiers of both badges 1304 and 1306, a timestamp of when the event occurred, a length of time that the badges 1304 and/or 1306 were within a proximity from each other, etc. The contact event can, in some embodiments, store a name of a user carrying a badge, an approximate location of the badge, a building or space that the event occurred within, etc.

When the badge 1306 (or alternatively the badge 1304) comes into range of the transceiver 1302 (e.g., responsive to receiving a wireless broadcast message from the transceiver 1302), the badge 1306 can wirelessly communicate all historical contact data stored by the badge 1306. In this regard, the badges 1304 and 1306 can collect contact events when the badges 1304 and 1306 are outside of range of the transceiver 1302 and upload the collected contact events to the transceiver 1302 when the badges 1304 and/or 1306 come into wireless communication range of the transceiver 1302. The transceiver 1302 can transmit the received historical contact data to the occupant tracking system 1130 for storage and analysis by the occupant tracking system 1130.

Responsive to sending the historical contact data to the transceiver 1302, the badge 1306 can clear (e.g., erase) the historical contact data stored by the badge 1306 to make room for storage of future contact event data. In some embodiments, the badge 1306 can store a historical buffer of contact events. Responsive to detecting that the buffer is filled, the badge 1306 can overwrite the oldest events first and preserve the most recent events of the buffer.

Figure 14:
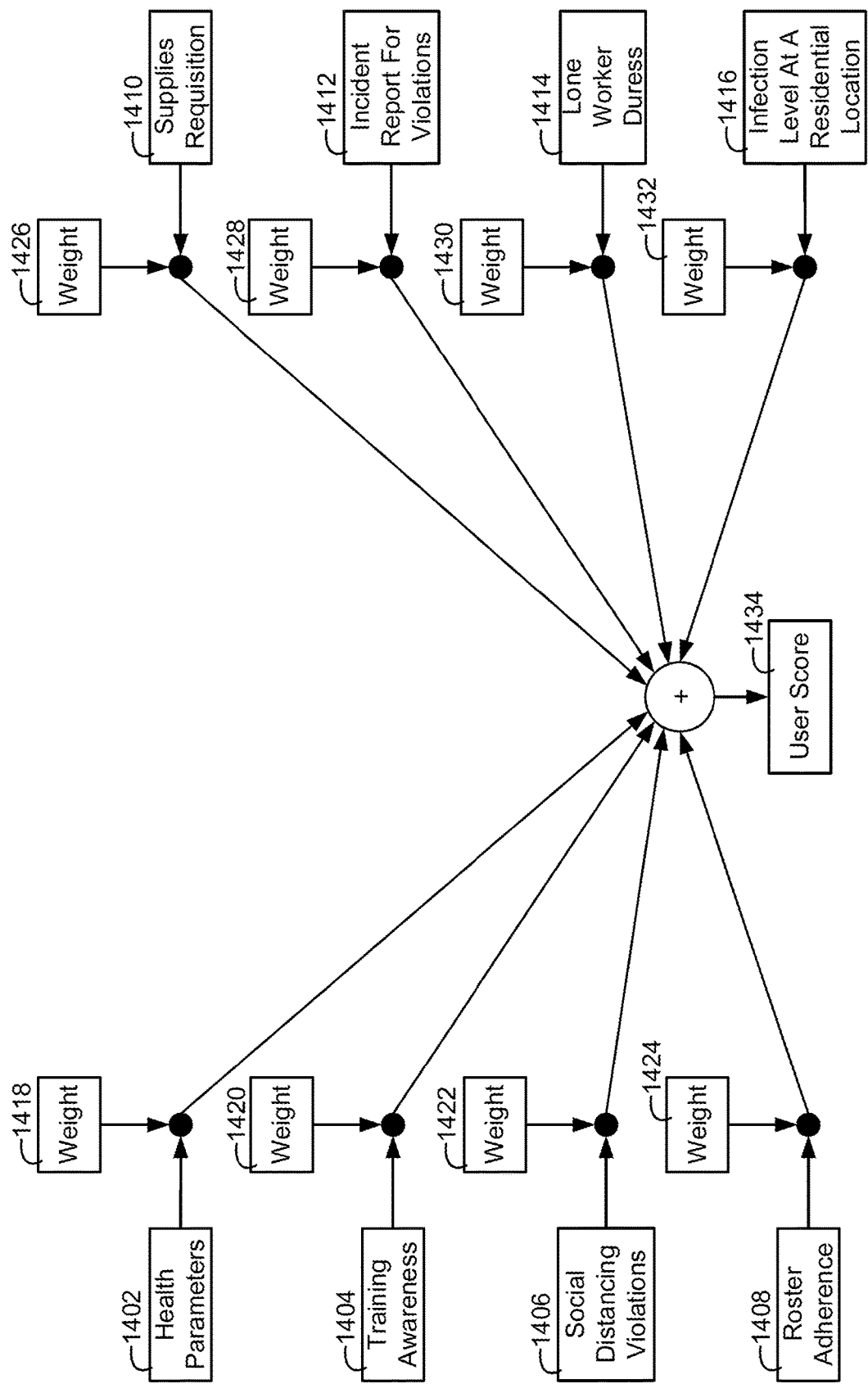
FIG. 14 is a block diagram of a scoring process for scoring a user based on factors that relate to the spread of an infectious disease and the health of the user, according to an exemplary embodiment.

Referring now to FIG. 14, a block diagram of a scoring process for scoring a user based on factors that relate to the spread of an infectious disease and the health of the user is shown, according to an exemplary embodiment. The user scoring service 1126 can be configured to perform the scoring process of FIG. 14 to score the occupant, e.g., generate the user score 1434. The user score 1434 can be generated based on the parameters 1402-1416 and the weights 1418-1432 associated with the various parameters 1402-1416 respectively.

The parameters 1402-1416 can be weighted by varying amounts. For example, the weights 1418 for the health parameters 1402 can be 20%. The weight 1420 for the training awareness parameter 1404 can be 10%. The weight 1422 for the social distancing violations parameter 1406 can be 20%. The weight 1424 for the roster adherence 1408 can be 10%. The weight 1426 for the supplies requisition 1410 can be 10%. The weight 1428 or the incident report for violations 1412 can be 10%. The weight 1430 for the lone worker duress 1414 can be 10%. The weight 1432 for the infection level at a residential location 1416 can be 10%.

The user score 1434 can indicate various protocols that should be set for the user being scored. The user scoring service 1126 can be configured to select the protocol and cause the user interface manager 112 to provide an indication of the protocol to the user device 1102. If the user score 1434 is between 85 and 100, the protocol may indicate that the user being scored is allowed to work from and office location. If the user score 1434 is between 65 and 85, the protocol may indicate that the user being scored is allowed to work from the office location on a limited number of days with some precautions in place (e.g., wearing a mask, taking social distancing trancing, etc.).

If the user score 1434 is between 45 and 65, the protocol may be that the user should work from home and can come into the office location when a physical presence of the user is essential (e.g., for an in person meeting, to work in a laboratory, when physical equipment is required by the user to perform the job of the user, etc.). If the user score 1434 is between 25 and 45, the protocol may be that the user being tested should not come into the office location and should work from home. If the user score 1434 is below 25, the protocol may be that the user should receive advice, counseling to take certain precautions, and/or should undergo special training.

The health parameters 1402 can be a definition of health parameters associated with the user. For example, the health parameters can indicate body temperature, cholesterol level, blood pressure, Body Mass Index (BMI), cardiovascular disease, diabetes, chronic respiratory disease, cancer, and/or any other health parameter. The health parameters 1402 can be received from Process Map, a Health Insurance Portability and Accountability Act (HIPPA) certified data source. The user scoring service 1126 can be configured to access and evaluate the health parameters 1402 based on criteria.

The criteria may be to bifurcate the weight 1418 across the various health parameters. For example, for a 20% weight, each health parameter that indicates a poor level may result in a particular decrease in points from the weight. For example, for a high temperature 10 points can be removed, for bad blood pressure two points can be removed, for poor cholesterol two points can be removed, for a poor BMI one point can be removed, for a cardiovascular disease one point can be removed, for a respiratory disease one point can be removed, for cancer one point can be removed.

The health parameters 1402 can include red flag indicators. For example, if the temperature of the user is more than 101 Fahrenheit for more than three days, a red flag indicator can be activated by the user scoring service 1126 and a notification (e.g., text message, email, etc.) can be distributed by the user interface manager 1112 to the security personnel and/or a facility team instructing the security personnel and/or the facility team to restrict building entry for the user. Furthermore, if the red flag indicator is tripped, the score for the health parameters 1402 can be set to zero.

The health parameters 1402 can be associated with a green flag. The green flag can indicate that if the user is healthy and none of the health parameters indicate poor health, a badge can be generated for the user. The badge may be a graphic with the text "Health Warrior." The badge can be distributed to the user device associated with the user being tested and/or otherwise linked to a user profile of the user.

The training awareness parameter 1404 can indicate whether a user has completed infectious disease awareness trainings assigned to the user. The training awareness parameter 1404 can be retrieved from a Learning Management System by the user scoring service 1126. Upon completion of the training assigned to the user, the user scoring service 1126 can apply all points associated with the training awareness parameter 1404 to the training awareness parameter 1404. The user scoring service 1126 can apply points to the user while the user is performing the training. The points applied may be based on a percentage of completion, e.g., Points earned=Total Points–(% remaining for the training completion/100)*Total Points.

The user scoring service 1126 can generate a red flag indicator if a user does not start training within a predefined amount of time after being assigned the training. For example, if a user does not start assigned training five consecutive days after joining an office, the red flag indicator can be activated for the training awareness parameter 1404. If the red flag indicator is active, the user can be added to a defaulters list and entry to the building restricted until the user completes training. The score for the training awareness parameter 1404 can also be set to zero if the red flag is active.

The social distancing violations parameter 1406 can indicate the social distancing violations made by the user being tested. The social distancing violations can be received from the social distancing service 1124. For each social distancing violation of the user being tested, the user scoring service 1126 can deduct a particular number of points from a total available number of points. For example, if the weight is 20, each violation can reduce the weight by five.

The user scoring service 1126 can determine a red flag based on the social distancing violations parameter 1406. In some embodiments, the user scoring service 1126 can activate the red flag if a particular number of social distancing violations have occurred, e.g., four social distancing violations. In response to the user scoring service 1126 activating a red flag for the user being tested, the user scoring service 1126 can be configured to generate a notification for an administrator and send the notification to a user device of the administrator. Furthermore, the user scoring service 1126 can add the user to a restricted access list for an access control system to restrict access by the user to the building. The score for the social distancing violations parameter 1406 can further be set to zero.

The user scoring service 1126 can activate a green flag indicator for the social distancing violations parameter 1406. If the user has not committed any social distancing violations, the user scoring service 1126 can activate the green flag for the user. The user scoring service 1126 can generate a "Defender" badge which may be a graphic with the text "Defender" and serve the badge to a user device of the user and/or associate the badge with an account of the user.

The user scoring service 1126 can be configured to evaluate adherence to a roster of an organization by one or more users. The user scoring service 1126 can receive the roster adherence 1408 from a roster system of a building that tracks users as they badge in or enter a building. The roster adherence 1408 can indicate whether a user has adhered to or violated a roster, e.g., entered the building at unscheduled times, missed entering the building at a scheduled time, etc. The weight 1424 for the roster adherence 1408 may be 10%. The user scoring service 1126 can be configured to deduct a predefined number of points from the weight 1424 for every roster violation. For example, the user scoring service 1126 can deduct five points from ten available points for every roster violation.

The user scoring service 1126 can activate a red flag indicator if a user violates a roster more than a particular number of times, e.g., two times. The user scoring service 1126 can add the user with a red flag to a defaulters list. An access control system can configured to restrict building access to users of the defaulters list. Furthermore, the score for the roster adherence 1408 can be set to zero when a red flag is activated for a user.

The user scoring service 1126 can be configured to generate a green flag indicator if a user has no roster adherence violations. The user scoring service 1126 can be configured to generate a badge for a user with an associated green flag indicator. The user scoring service 1126 can be configured to serve the badge to the user and/or associate the badge to a user account of the user. The badge may be a graphic with the text "Roster Soldier."

The user scoring service 1126 can be configured to evaluate supplies requisition 1410, e.g., evaluate whether a user can acquired protection supplies for stopping the spread of an infectious disease such as masks, sanitizers, paper towels, etc. The supplies requisition 1410 can be data pulled from a system and/or a database of an employer that indicates which users have ordered and/or picked up their supplies.

The weight 1426 can be a 10% weight for the supplies requisition 1410. The user scoring service 1126 can be configured to apply more available points to a user based on requests for supplies that the user has made. For example, for requesting a mask, the user may be awarded five points. For requesting sanitizer, a user may be awarded another five points. For requesting any other supplies, the user may be awarded another five points. Every time the user performs a hygienic practice by requesting supplies, the user scoring service 1126 can be configured to add points to a total score of a user.

The user scoring service 1126 can be configured to generate a green flag indicator for the user in response to a user getting all points available. The user can be added by the user scoring service 1126 to a green flag holders list and provided a badge. The user scoring service 1126 can be configured to serve the badge to a user device of the user and/or associate the badge with an user account of the user. The badge may be a graphic based badge with the text "Defender."

The user scoring service 1126 can be configured to generate the user score 1434 based on the incident report for violations 1412. The user scoring service 1126 can be configured to add points to a user score for each incident relating to health and/or safety that the user being scored logs in a system. For example, a user, via their user device, may report information such as social distancing violations, poor health practices, lack of sanitization, lack of a mask, etc. to a system and/or the user scoring service 1126. The system could be a ticket generation system that receives and logs tickets reported by a user that summarize incidents within a building. The user scoring service 1126 can retrieve the incident report for violations from the system. The incident report for violations can indicate a list of users who have raised incident tickets for violations against health and safety rules laid down by an organization.

The user scoring service 1126 can generate the score based on weight 1428 which may be a 10% weight. The weight may be the maximum amount of points available to a user. The user may be assigned a particular number of points, e.g., two points for every incident ticket that is logged in the system. The more tickets that the user records, the more points that the user scoring service 1126 may assign the user. If the ticket count exceeds a particular number, e.g., five, the user scoring service 1126 can assign a maximum number of points to the user, e.g., ten points.

The user scoring service 1126 can generate a green flag indicator for a user if the user logs more than a particular number of tickets within a particular amount of time, e.g., five tickets per day to indicate violations of health and safety rules by another user. The reward for the green flag indicator may be a "Buddy Cop" badge, a graphic badge with the text "Buddy Cop."

The user scoring service 1126 can be configured to generate the user score 1434 based on indications of lone worker duress 1414. The weight 1430 can be 10% and/or any other weight for weighting the indications of lone worker duress 1414. The lone worker duress 1414 can be an indication that the user being scored has required attention in the building in response to working alone and/or being isolated from other individuals. In response to a lone worker duress notification being recorded by the building disease control system 1104 for the user, the user scoring service 1126 can subtract a particular number of points from a maximum number of points, e.g., two points.

The user scoring service 1126 can be configured to generate the user score 1434 based on the infection level at a residential location of a user. The location where a user lives may be an important factor with respect to exposure to an infectious disease. The user scoring service 1126 can receive infection levels from a database, e.g., a state database, a Center For Disease Control (CDC) database, etc. Furthermore, the residential address of the user can be retrieved by the user scoring service 1126 from an employer database which stores the mailing addresses and/or residential addresses for all employees.

The user scoring service 1126 can be configured to compare the location of the user against the areas of varying infection levels. The geographic areas can be tagged according to various ranges of infection level. The areas can be a green zone, a yellow zone, an orange zone, a red zone, or a containment zone based on the infection level in a particular geographic area. The user scoring service 1126 can subtract a particular number of points, or no points, from a maximum available number of points, e.g., 10%, based on whether the residence of the user is located within a zone that falls into one of the aforementioned categories. For the green zone, zero points can be removed from the total. For the yellow zone, 2.5 points can be removed from the total. For the orange zone 5 points can be removed from the total. For the red zone, 7.5 points can be removed from the total. For the containment zone, 10 points can be removed from the total.

Figure 15:
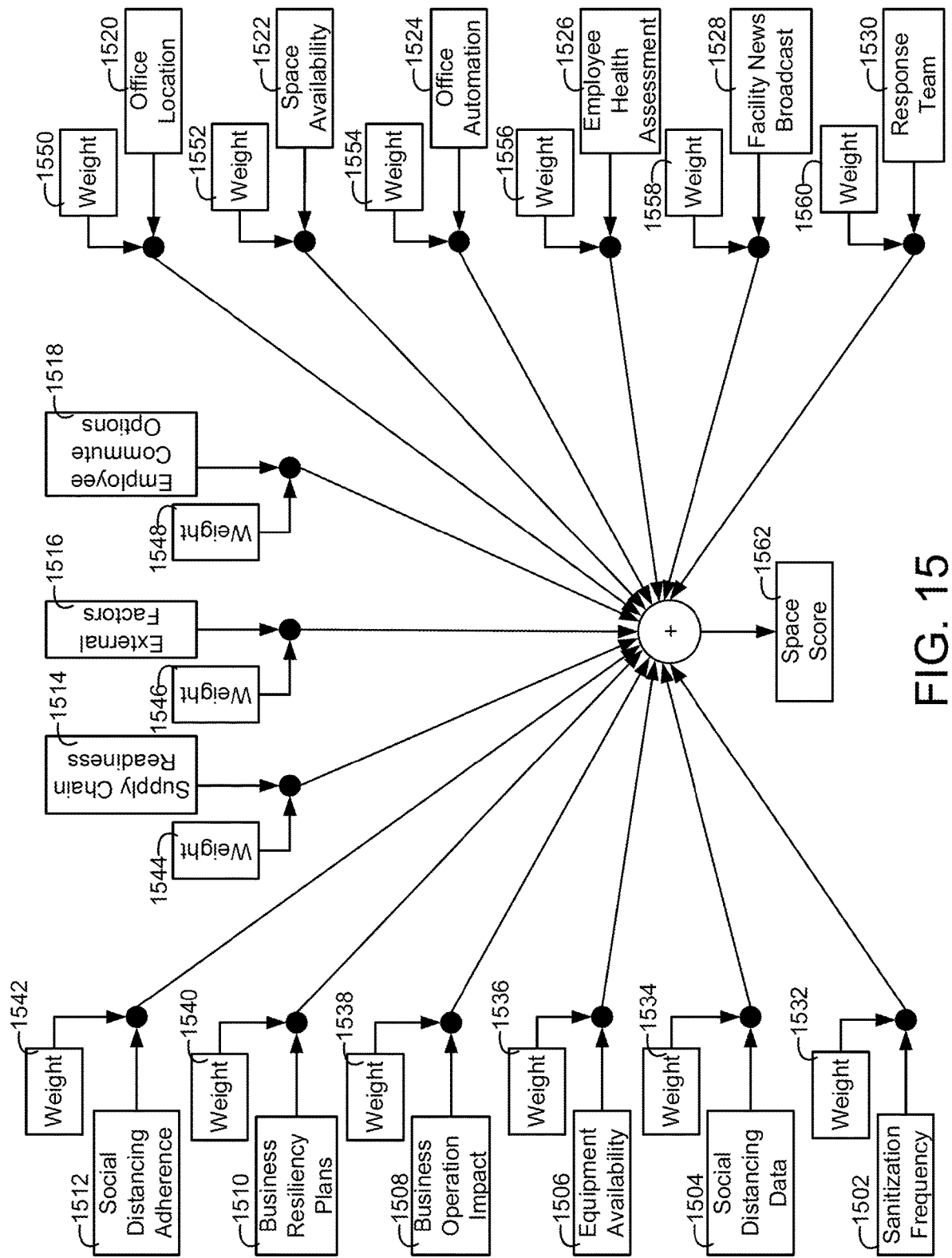
FIG. 15 is a block diagram of a scoring process for scoring a space of a building based on factors that relate to the spread of an infectious disease in the space, according to an exemplary embodiment.

Referring now to FIG. 15, a block diagram of a scoring process for scoring a space of a building based on factors that relate to the spread of an infectious disease in the space is shown, according to an exemplary embodiment. The space scoring service 1120 can be configured to perform the scoring process of FIG. 15 to score various zones of a building, e.g., generate the space score 1562. The user score 1434 can be generated based on the parameters 1402-1416 and the weights 1418-1432 associated with the various parameters 1402-1416 respectively.

The parameters 1502-1530 can be weighted by varying amounts. Each of the parameters 1502-1530 can be weighted by one of the weights 1532-1560. The sanitization frequency parameter 1502 can indicate how frequently a space of a building has been sanitized. The sanitization frequency parameter 1502 can indicate when the space was last sanitized and/or whether the space has or has not been sanitized within a particular historical time window.

The social distancing data 1504 can indicate live occupancy counts for a space of a building. The occupancy count can indicate whether social distancing is being practiced for the space, e.g., whether the number of occupants exceeds an occupant limit that is based on the size of the space. The space scoring service 1120 can increase the space score 1562 if social distancing is followed and decrease the space score if the social distancing is not followed.

The equipment availability 1506 can indicate whether equipment for reducing the spread of an infectious disease is present in an area of the building. The equipment can be a disinfectant light system that cleans the space. The equipment can be a ventilation system that increases ventilation for an area of a building. If the equipment is present, the space scoring service 1120 can increase the space score 1562. If the equipment is not present, the space scoring service 1120 can reduce the space score 1562.

The business operation impact 1508 can indicate how important a space is to a business. The space scoring service 1120 can increase or decrease the space score 1562 based on a level of importance of the space being scored. The business resiliency plans 1510 can indicate the resiliency plans that a business has in place for the particular space of the building. The social distancing policy governance and adherence can indicate whether social distancing policies are adhered to within the space, e.g., whether occupants maintain a specific distance apart, whether the occupants wear masks, whether the occupants utilize sanitizer, etc.

The space scoring service 1120 can analyze supply chain readiness 1514 and/or external factors 1516 in determining the space score 1562. The space scoring service 1120 can further analyze commute options for employees in traveling to a building when the building is the space being scored. The space scoring service 1120 can be configured to analyze the location of the building, e.g., determine whether the building is located in a high infection geographic area. Based on the infection level of the geographic area that the building is located in, the space scoring service 1120 can increase or decrease the space score 1562.

The space scoring service 1120 can determine the space score 1562 for a space based on space availability 1522, an indication of how often the space is available for occupants and how frequently the space is in use. When the space is not in use, it is easier to practice social distancing within the space than when the space is not in use. Therefore, a less frequently used space may have a higher space score 1562.

The space scoring service 1120 can be configured to determine the space score 1562 based on the office automation 1524. The office automation 1524 can indicate the systems that are available for a space and/or a building. The office automation 1524 can indicate whether frictionless entry is present, contactless payments for vendors is present, paperless options are available, social distancing and occupant tracking is available, etc. The space scoring service 1120 can increase the space score 1562 for every form of automation present.

The employee health assessment 1526 can indicate employee health for every occupant of a building and/or space. For example, the health of all employees of a particular building space could be used to determine the space score 1562 by the space scoring service 1120. In some embodiments, the space scoring service 1120 could determine the space score 1562 based on the health assessments for current occupants of a particular space. The space scoring service 1120 can be configured to determine the space score 1562 base on news broadcasts associated with a building. Furthermore, the space scoring service 1120 can be configured to determine the space score 1562 based on the response team 1530 which may indicate the availability of a response team at a building or for a particular area of the building.

Figure 16A:
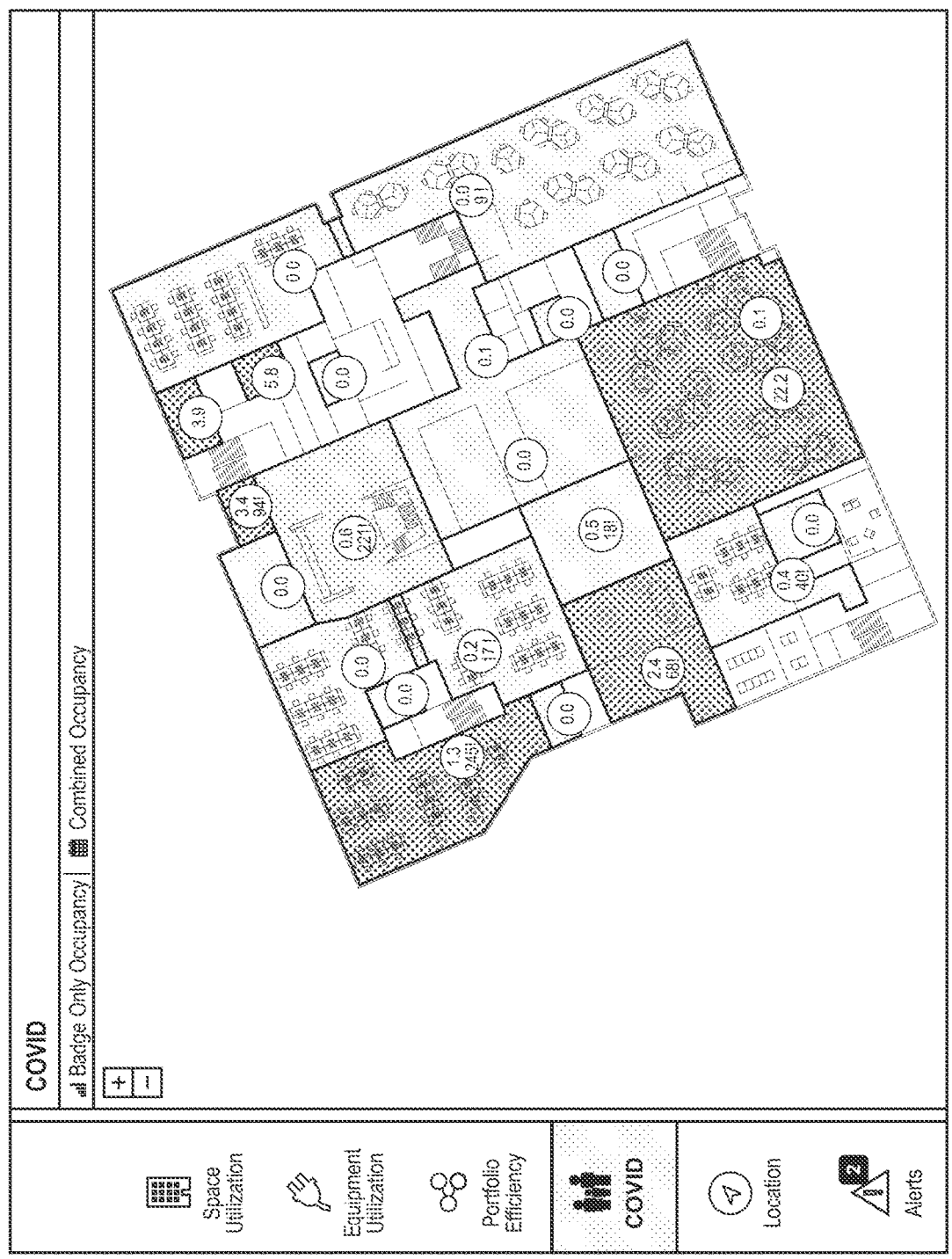
FIG. 16A is a schematic diagram of a social distancing user interface that indicates occupancy levels for various areas of a building, according to an exemplary embodiment.
Figure 16B:
FIG. 16B is a schematic diagram of another social distancing user interface that indicates occupancy levels for various areas of a building, according to an exemplary embodiment.

Referring now to FIGS. 16A-16B, social distancing user interfaces 1600 and 1602 that indicate occupancy levels for various areas of a building are shown, according to an exemplary embodiment. The interfaces 1600 and 1602 can include heat maps indicating utilization of spaces of a building floor with respect to social distancing compliance. The social distancing service 1124 can determine occupancy levels for spaces such as desk spaces, collaborations areas, meeting rooms etc. The areas can be customizable and defined via a user via the user device 1102. In some embodiments, the user interface manager 1112 can be configured to generate the user interface 1600-1602 and cause the user device 1102 to display the user interface 1600-1602.

The social distancing service 1124 can be configured to determine occupancy levels for each area of the building. Each area of the building is included within a floor plan of the interfaces 1600 and 1602. The social distancing service 1124 can determine, based on the occupancy of each space and the physical size of each space, whether an occupancy of a space is greater than an occupancy allowed by the space.

An occupancy level allowed for each space may be a level at which social distancing can be practiced, i.e., a level based on a size of a space (e.g., square feet) that occupants can maintain a particular distance between each other. The particular distance can be based on a type of disease and may be a recommended distance to stay away from occupants so that the disease is not spread. The allowed occupancy level can further be based on space characteristics such as number of air changes per day for the space by HVAC equipment, ventilation for the space, whether windows are opened and allowing fresh air into the space, the total volume of the space, etc. The spaces of the building can be color coded, e.g., green, blue, and red, to indicate the level of occupancy relative to the physical area of the space, e.g., blue if the space is a first particular number of occupants under the level, green if the space is a second particular number of occupants less than the level but greater than the first particular number, and red if the occupancy of the space is greater than the allowed level.

In some embodiments, the user interfaces 1600 and 1602 can indicate historical usage patterns of a building. For example, an average occupancy can be tracked for every space of the building. If the average occupancy is greater than a first particular amount, the space can be marked as red. If the average occupancy is less than the first particular amount but greater than a second particular amount, the space can be marked as green. If the average occupancy is less than the second particular amount, the space can be marked as blue. The green indicator may be the target indicator for every space, to raise utilization to an efficient level but not create social distancing violations.

In some embodiments, the red spaces indicate non-compliance with social distancing for a space, the green spaces indicate compliance with the social distancing practices within the space, and the blue spaces indicate the opportunity to add employees to the space while still maintaining social distancing practices. Based on the locations of the transceivers 1132-1136, the social distancing compliance of each space can be determined.

In some embodiments, a larger geofence can have a smaller child geofence. For example, the bottom red zone in FIG. 16A. In this regard, the larger zone may have additional beacons spread out throughout the zone to determine granular occupancy levels for the smaller child geofence. In response to a zone becoming red, the social distancing service 1124 can generate a notification for individuals of the zone notifying the individuals are violating a social distancing practice. The notification can be served to user devices of the occupants via a text message, an email, and/or a mobile application notification.

In some embodiments, a user can interact with one of the zones of the interfaces 1600-1602. The interface can update to show specific information for each zone. For example, average occupancy of the zone, average dwell time the zone, a list of the badge numbers and/or names of occupants in the zone that are causing a social distancing violation, etc. In some embodiments, the interface for the zone can include contact tracing data determined by the contact tracing service 1114. The contact tracing data can indicate two or more individuals that have made an encounter, e.g., two or more individuals who have been in close proximity (e.g., within two meters) for a particular amount of time (e.g., fifteen minutes).

Because the interfaces indicate location of an encounter based on the transceivers 1132 detecting two occupants in close proximity, there may be an advantage for contact tracing by adding an additional dimension to a contact tracing analysis, e.g., the location of encounters. This may have an advantage over phone to phone or badge to badge based contact tracing which may rely on ad-hoc communication between two devices where the devices may not determine or store their location information. By seeing how and when occupants are in a room, contact tracing can be performed. For example, even if occupants were not within close proximity but a first occupant was in a room quickly followed by another occupant being in the same room, an encounter can be recorded since each individual were in the same room within a short period of time.

Figure 17:
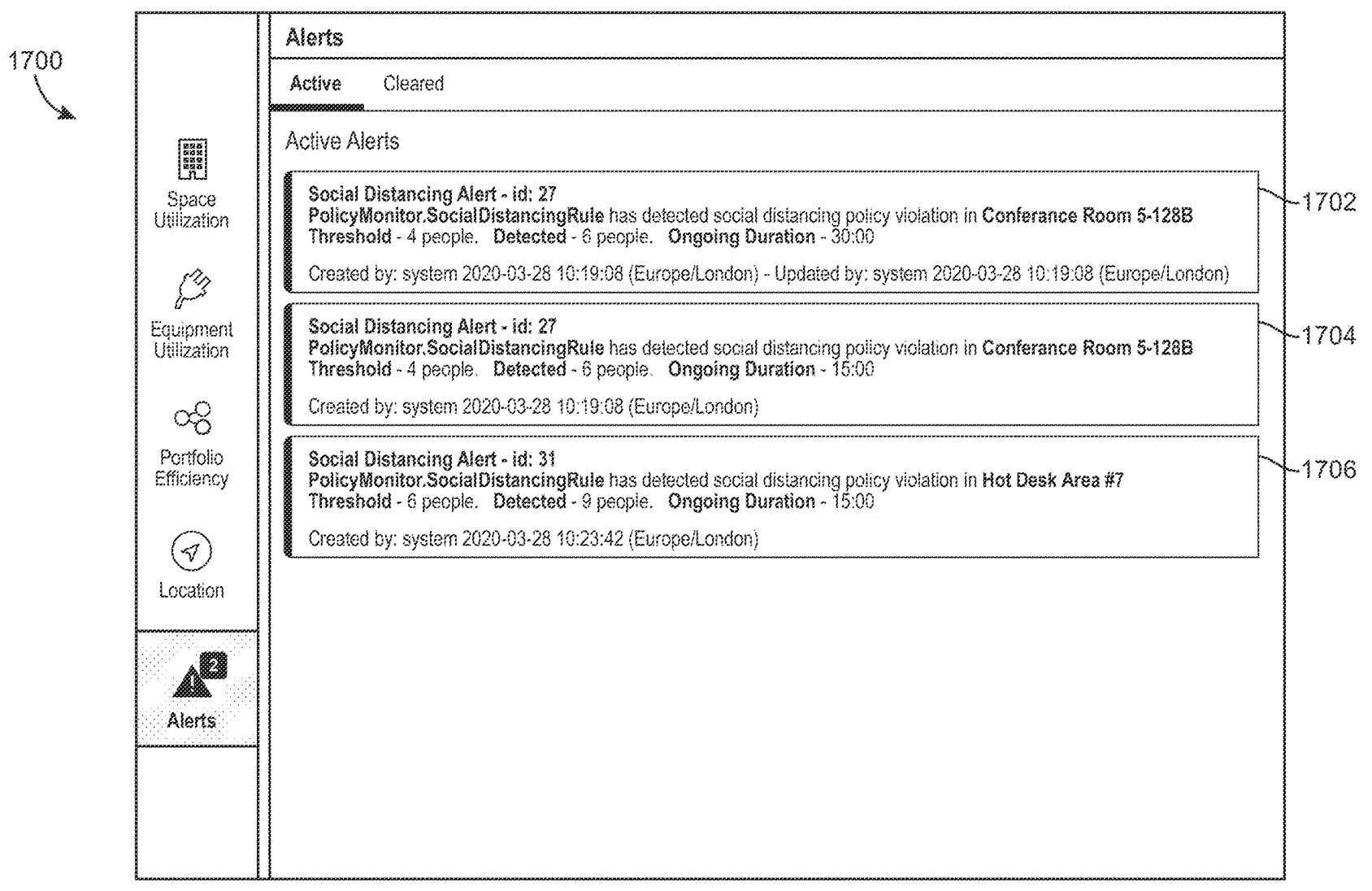

Referring now to FIG. 17, a user interface 1700 including social distancing alerts is shown, according to an exemplary embodiment. The interface 1700 indicates social distancing violations. This helps promote social distancing practices in a building by notifying individuals that may intervene with an ongoing social distancing violation. In some embodiments, the user interface manager 1112 can be configured to generate the user interface 1700 and cause the user device 1102 to display the user interface 1700.

In the user interface 1700, alert 1702 is a social distancing alert for a conference room. The severity level can be critical (e.g., a red alert) because the alert has exceeded a particular amount of time, e.g., the occupancy threshold has been exceeded for thirty minutes. In the user interface 1700, alert 1704 indicates that a social distancing violation has occurred for fifteen minutes. The alert 1704 is a major alert (e.g., an orange alert) for a conference room. The alert 1704 is not a critical alert because the social distancing violation has only lasted for fifteen minutes. Alert 1706 indicates a major alert for a hot desk area where occupants have gathered and exceeded an occupancy threshold for fifteen minutes.

Figure 18:
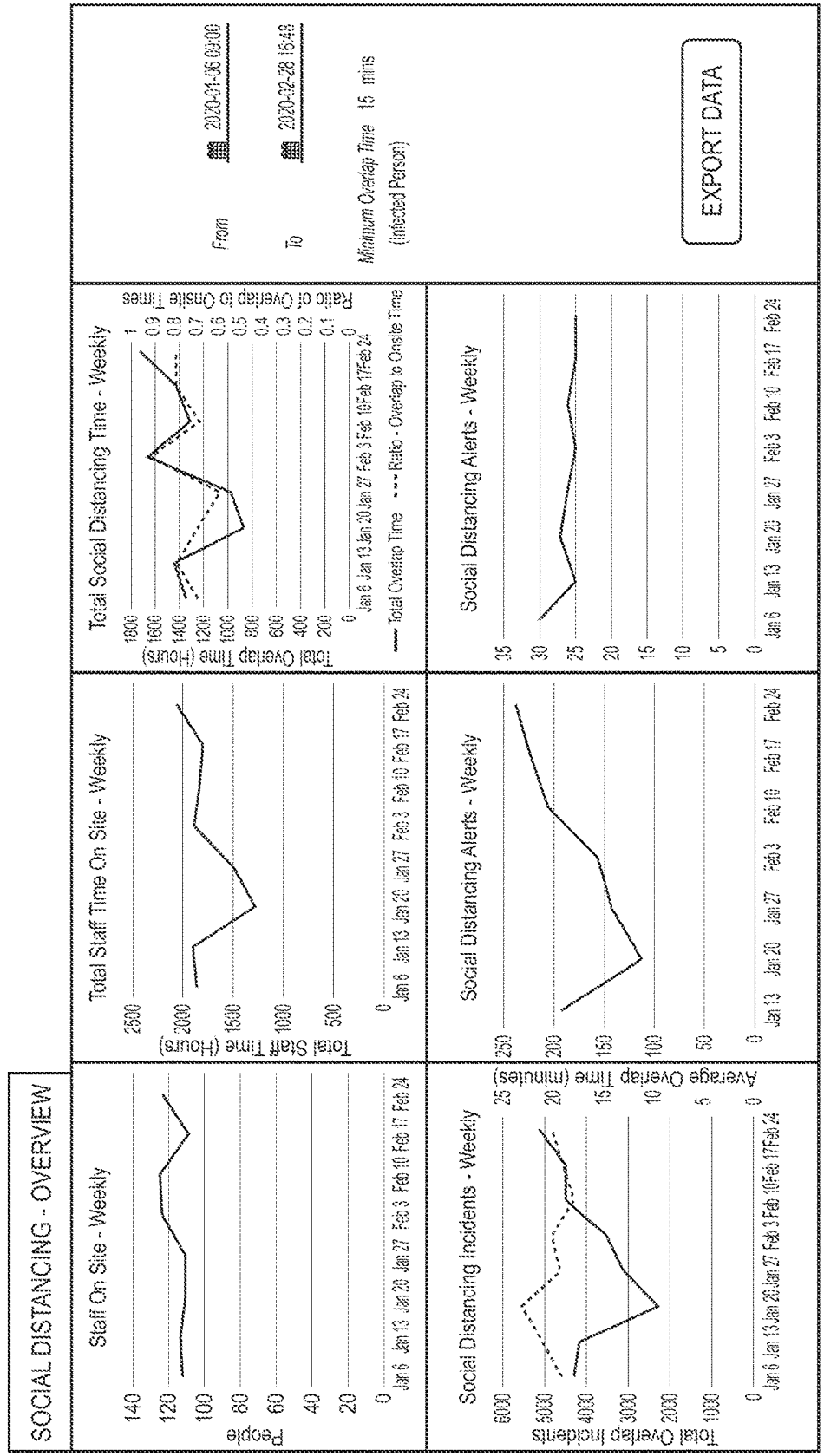
FIG. 18 is a schematic diagram of a user interface including trends of social distancing data, according to an exemplary embodiment.

Referring now to FIG. 18, a user interface 1800 including trends of social distancing data is shown, according to an exemplary embodiment. In some embodiments, the user interface manager 1112 can be configured to generate the user interface 1800 and cause the user device 1102 to display the user interface 1800. In some embodiments, the social distancing service 1124 can generate the data and/or data trends for display in the user interface 1800.

The social distancing interface 1800 can include dashboards that users of companies can review to understand how well social distancing is being practiced in a building of the company. The interface 1800 can indicate all social distancing violations that have occurred in the building. For example, any event where two or more occupants come within two meters for a particular length of time (e.g., fifteen minutes) can trigger a social distancing violation.

The social distancing violations that result in alert generation can be particularly dangerous social distancing violations, e.g., being within two meters for at least 15 minutes. In some embodiments, social distancing violation notifications may only be generated when an occupant makes a high number of violations. In some embodiments, the social distancing violation is generated when a particular number of individuals are violating the social distancing policies (e.g., a crowd of people). This allows the system to track all social distancing violations but does not overwhelm users with a high number of alerts. In some embodiments, the distance between occupants and the duration of time required for a social distancing violation and/or notification to be generated is provided by a user via the device 1102.

The social distancing interface 1800 can provide weekly (or daily, monthly, and/or yearly) trends of social distancing violations and other information to indicate how well social distancing practices are being handled at a building. The interface 1800 includes a trend of staff on site at the building for each week. Furthermore, the interface 1800 indicates total staff time at the building for each week. The total time can be based on access control system data that indicates when each occupant arrives at the building and departs from the building.

The interface 1800 indicates total social distancing time for each week. This can help indicate the amount of time where social distancing practices are not followed in the building. The interface 1800 can indicate social distancing incidents for a building recorded for each week. For example, total number of social distancing events and their average duration is included within the interface 1800. Furthermore, the number of social distancing alerts generated on a weekly basis can be included within the interface 1800 to the number of social distancing violations that have resulted in alert generation for each week. Furthermore, the interface 1800 can include an indication of a number of weekly problem areas of a building, e.g., different areas of the building where social distancing did not take place.

In some embodiments, a user, via the user device 1102, can indicate input data for generating the trends displayed in the interface 1800. The input day may be a time range for which a report can be run and a minimum contact time for determining social distancing violations can be indicated. Interacting with the export data button can cause the user interface manager 1112 to generate an export file including the information displayed within the interface 1800.

Figure 19:
FIG. 19 is a schematic diagram of a user interface including a heat map that indicates occupant traffic levels of a building, according to an exemplary embodiment.
Figure 20:
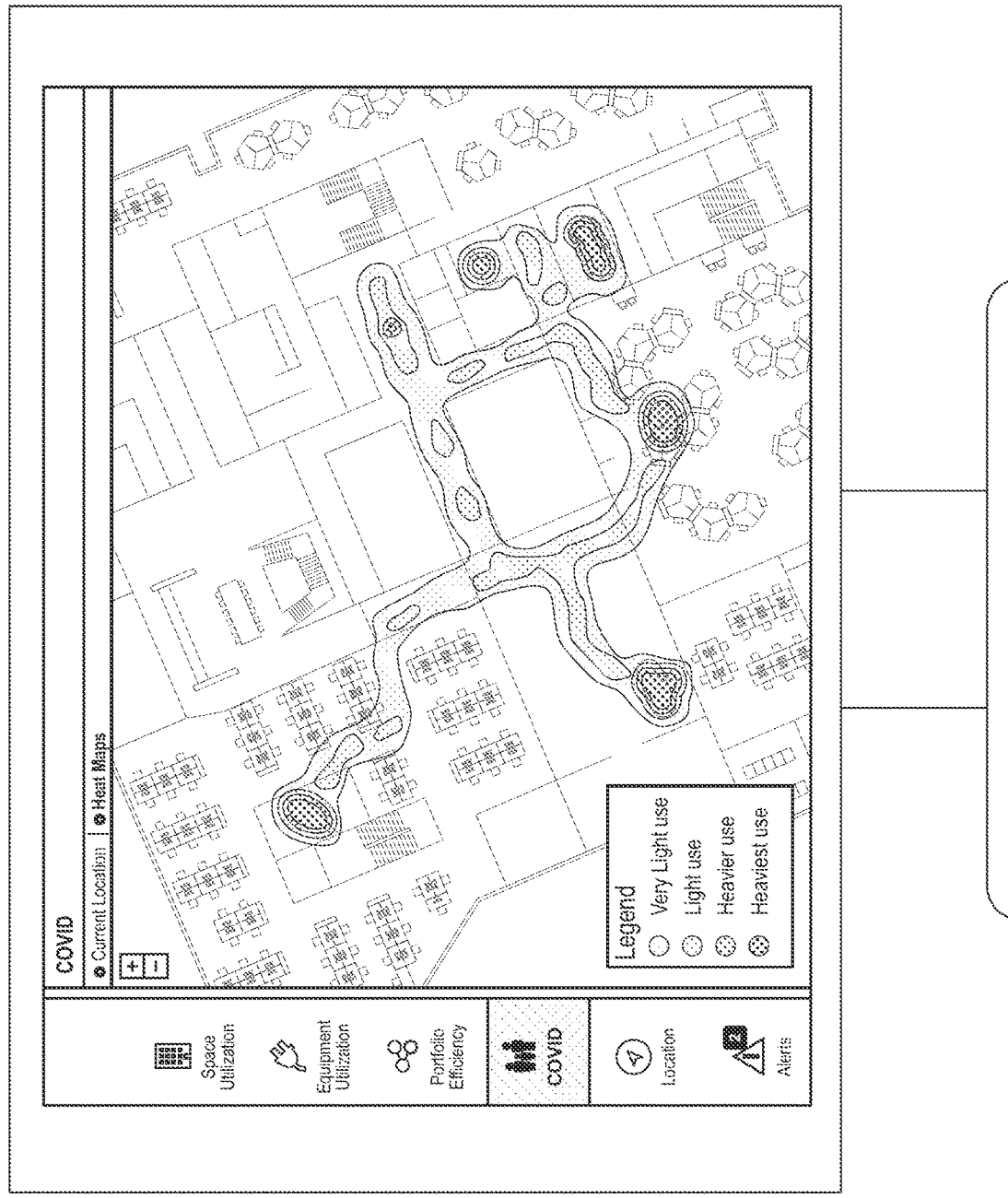
FIG. 20 is a schematic diagram of another user interface including a heat map that indicates occupant traffic levels of a building, according to an exemplary embodiment.

Referring now to FIGS. 19-20, user interfaces 1900-2000 including heat maps that indicate occupant traffic levels of a building is shown, according to an exemplary embodiment.

In some embodiments, the user interface manager 1112 can be configured to generate the user interfaces 1900-2000 and cause the user device 1102 to display the user interfaces 1900-2000. In some embodiments, the contact tracing service 1114 can generate the data and/or data trends for display in the user interfaces 1900-2000.

The user interfaces 1900-2000 can indicate usage hot spots that indicate historical uses of a space indicated by the red, yellow, green, and blue markings on the floor plans of the building. This can indicate high usage areas of the building, locations associated with a higher risk of infection transmission. In some embodiments, the heat map can be utilized by the space manager 1118 to generate a cleaning schedule for the building.

The space manager 1118 can be configured to identify high risk area and prioritize the high risk areas for deep cleaning. Furthermore, in some embodiments, the high risk areas can also take into account individuals that have tested positive for an infectious disease as identified by the contact tracing service 1114. In this regard, the space manager 1118 can schedule cleaning for areas where an infected individual has been present.

In some embodiments, the interface 1900 indicates the locations of all occupants of a building. However, locations of one or a small set of users are shown in interface 2000. In this regard, a user can track the locations of particular occupants. For example, if ten occupants test positive for an infectious disease, the user could request, via the user device 1102, to view a heat map generate for the ten occupants in order to plan response and/or cleaning. In some embodiments, the response and/or cleaning can be performed automatically by the building disease control system 1104.

Figure 21:
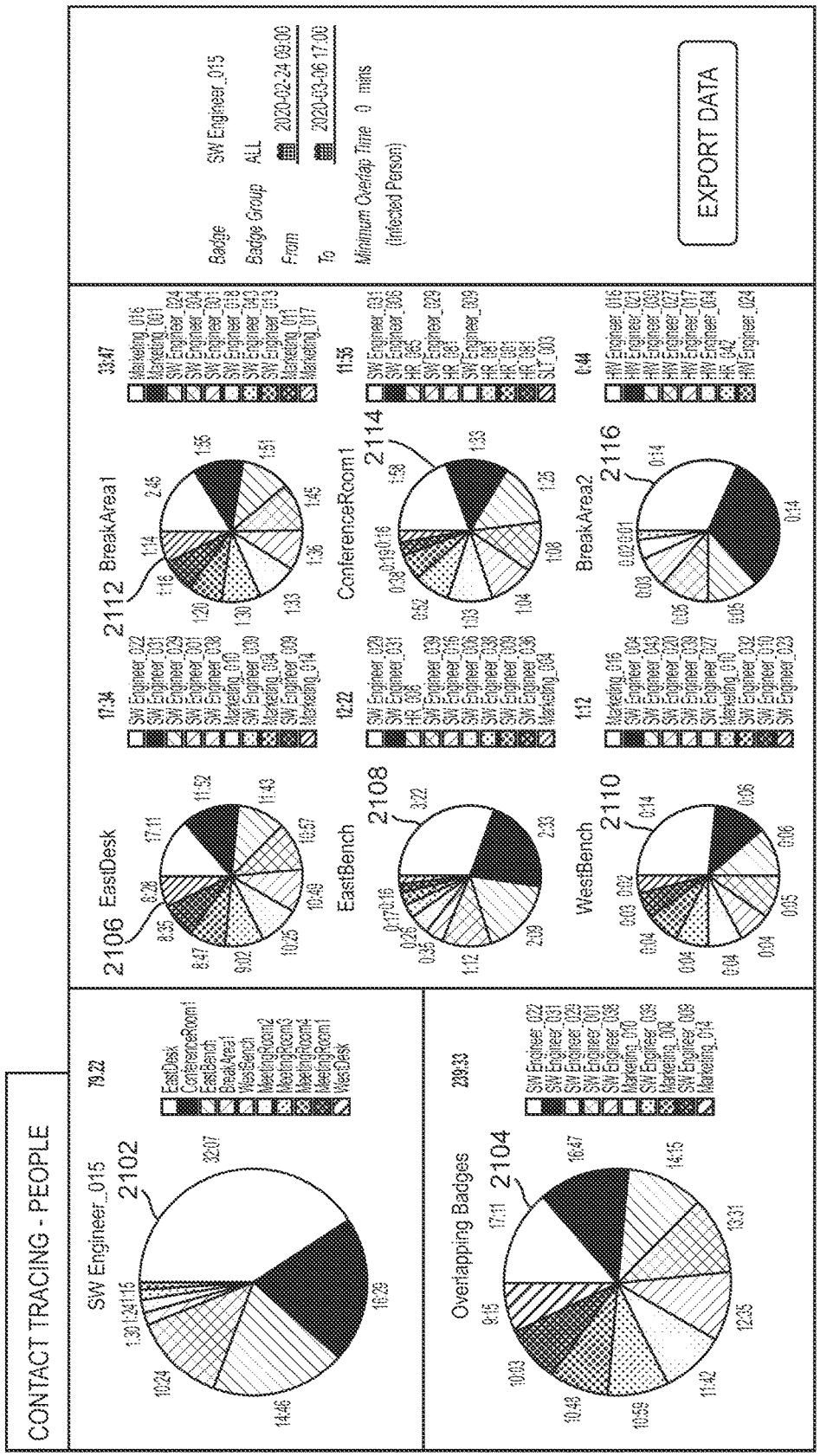
FIG. 21 is a schematic diagram of a user interface indicating contact tracing data for occupants of a building, according to an exemplary embodiment.

Referring now to FIG. 21, a user interface 2100 indicating contact tracing data for occupants of a building is shown, according to an exemplary embodiment. In some embodiments, the user interface manager 1112 can be configured to generate the user interface 2100 and cause the user device 1102 to display the user interface 2100. In some embodiments, the contact tracing service 1114 can generate the data and/or data trends for display in the user interface 2100.

The interface 2100 can indicate a breakdown of historical data for occupants and the locations that the occupants frequent. The historical data can be derived from data collected from the occupant tracking system 1130 via the transceivers 1132-1136 and the credential 1138. The interface 2100 can indicate desks assigned to each occupant. The interface 2100 indicates a snapshot of data requested by a user from February through March of a particular year. The length of time that the report is generated for can be specified by a user via the user device 1102.

The pie chart 2102 indicates the locations that a software engineer associated with badge number 15 has spent time. The pie chart indicates the top ten places that the software engineer has spent time and indicates the proportion of time spent at each location. The pie chart 2104 indicates the cumulative time spent overlapping with other employees of an organization.

In some embodiments, to generate the interface 2100, a user, via the user device 1102, enters a badge number, a badge name, etc. of a contact that the user wishes to trace. The user can further select one or more groups of occupants that the user wishes to generate the interface 2100 for. Furthermore, the user can specify the time period for which to run the contact trace. The user can indicate an amount of overlap time for generating an encounter between two individuals, e.g., the amount of time that the two occupants needs to be within a particular distancing to generate an encounter.

The pie chart 2102 indicates that a software engineer has spent 79:22 (e.g., hours and minutes) in cumulative time within a facility. The locations where the software engineer has spent the most time are included in descending order. The area that the software engineer has spent the most time is the East Desk. The software engineer has spent a total of 32:07 at the East Desk. The pie chart 2104 indicates the top ten other people that the software engineer has overlapped with. The cumulative time of overlap is 239:33. The pie chart 2104 indicates that another software engineer has been overlapped with the software engineer for 17:11. The top ten individuals that the software engineer has overlapped with are shown in descending order of total overlap time.

The interfaces further includes pie charts 2106-2116 which indicate total overlap time of the software engineer with other occupants at various desks, benches, break areas, and conference rooms of the building. The pie charts 2106-2116 can be ordered based on total aggregate time such that the pie chart with the highest total time is displayed first. There are six pie charts 2106-2116 where the software engineer has spent time. However, if the software engineer were to have spent time in more than six locations, a user could scroll in the interface 2100 to view additional pie charts for the user.

The pie chart 2112 indicates overlap time of the software engineer at a first break area with various marketing individuals and other software engineers. The software engineer overlapped with other individuals in the first break area for a total of 33:47 (minutes and seconds). Furthermore, the pie chart 2106 indicates that the software engineer has overlapped with other individual for a total of 177:34 at an East Desk. The pie chart 2116 indicates the total overlap time with occupants in a second break area. The software engineer has spent a total overlap time of 0:44 in the second break area.

The interface 2100 includes an export button. If the user interacts with the export button, a file including all of the charts and/or underlying data used to building the charts of the interface 2100 can be generated. In some embodiments, the file is a Comma Separated Values (CSV) file. The interface 2100 includes an element for entering an indication of a minimum overlap time (e.g., five minutes, ten minutes, and fifteen minutes) to indicate the minimum amount of time that two or more occupants are within a particular distance. This flexibility in defining parameters such as overlap time help a building manager or other user to set parameters that are best for their particular building. For example, if for a two hour period, five minute overlap does not provide any viewable data, the user can change the minimum overlap time to fifteen minutes.

Referring now to FIG. 22, a user interface 2200 including a table indicating social distancing data for occupants of a building, according to an exemplary embodiment. The interface 2200 provides social distancing information on an individual occupant level. The user interface 2200 displays the total number of unique areas an occupant has violated social distancing. The interface 2200 displays a high level view of social distancing within the organization.

The user interface 2200 provides a report for occupants that breaks down a high level view into the behaviour of each occupant. The user interface 2200 identifies roles where a level of social distancing violations are higher than normal. The user interface 2200 can be used to help users change their behaviour and work practices so that occupants with high social distancing violations will help reduce the effects on other employees, and the overall business, should one of these people test positive. The user interface 2200 can help provide indications of the actions of users who may have tested positive for an infectious disease. In some embodiments, if an occupant tests positive for an infectious disease, the user interface 2200 can be used to review the behavior of the positive occupant.

In the user interface 2200, the column of unique badges with social distancing violations includes blue cells and red cells. The column of unique badges with social distancing violations indicates the total number of unique occupants with which a particular occupant has violated a social distancing policy. The total number of violations is above a particular amount, the cell is included as a red cell. If the total number of violations is below the particular amount, the cell is included as a blue cell.

The unique areas with social distancing violations indicate unique areas of a building where a particular occupant has made a social distancing policy violation. The total number of violations is above a particular amount, the cell is included as a red cell. If the total number of violations is below the particular amount, the cell is included as a blue cell.

The user interface 2200 includes a social distancing violation time that indicates the total amount of time that a particular occupant has made a social distancing violation. For example, the total amount of time that an occupant has been within a particular distance from another occupant. Furthermore, the user interface 2200 includes an on-site time column which indicates the total amount of time that each occupant is at a particular site, e.g., within a building, on a campus, etc.

The user can enter a date range in the user interface 2200 via the user device 1102. In FIG. 22, the user interface 2200 indicates a date range of Feb. 24, 2020 through Mar. 6, 2020. Furthermore, the user can enter a minimum overlap time to indicate how long two or more occupants must be within a particular distance for a social distancing policy to be violated. In response to interacting with the export data button, a data file can be generated with the information of the user interface 2200.

Referring now to FIG. 23, a table 2300 comparing features of various occupant tracing systems is shown, according to an exemplary embodiment. The table 2300 provides a comparative solution analysis of various location based solutions. The building disease control system 1104 indicates the transceiver and badge solutions illustrated in FIGS. 13A-B.

Bluetooth enabled phone applications may have variability in Bluetooth software and hardware across mobile phones, even from the same vendor, is so significant that location accuracy can vary wildly. There may be too many false positives from these apps, where people ten meters apart are being measured incorrectly at one meter, will eventually result in them being discarded. Furthermore, it may be difficult to make users download the mobile application. Utilizing Bluetooth in the building disease control system 1104 described in FIGS. 13A-13B uses badges and transceivers with the same software and hardware compatibility, eliminating inaccuracies caused by radio frequency (RF) sensitivities. The density of transceivers deployed in the building, can deliver extremely accurate location information, as the badges location is being measured by many transceivers, not just a single transceiver, which would be the case with a mobile phone application.

In addition to monitoring social distancing, and delivering contact tracing capability, the building disease control system 1104 of FIG. 13A-13B can provide an executive view of how social distancing is being practiced, with social distancing dashboards. A selection of weekly graphs show clearly the level of employees' social distancing. The weekly trends quickly highlight any negative changes in social distancing which might merit corrective actions.

With the building disease control system 1104 of FIGS. 13A-13B, the only hardware that may need to be deployed to a building are the user badges and the transceivers (which can be inserted in electrical sockets or mounted on the ceilings). The building disease control system 1104 can run in the cloud. In this regard, the building disease control system 1104 and the building disease control system 1104 of FIGS. 13A-13B can be installed quickly in a building. Furthermore, the building disease control system 1104 can perform a space utilization analysis, workflow analysis, collaboration analysis, and/or visitor and insider security.

Solutions such as under desk sensors, overhead people counters, access control systems and CCTV systems all offer a small degree of monitoring social distancing, but all very limited, with little or no ability to do contact tracing. These solutions are only counting people and have no idea who the people actually are.

Figure 24:
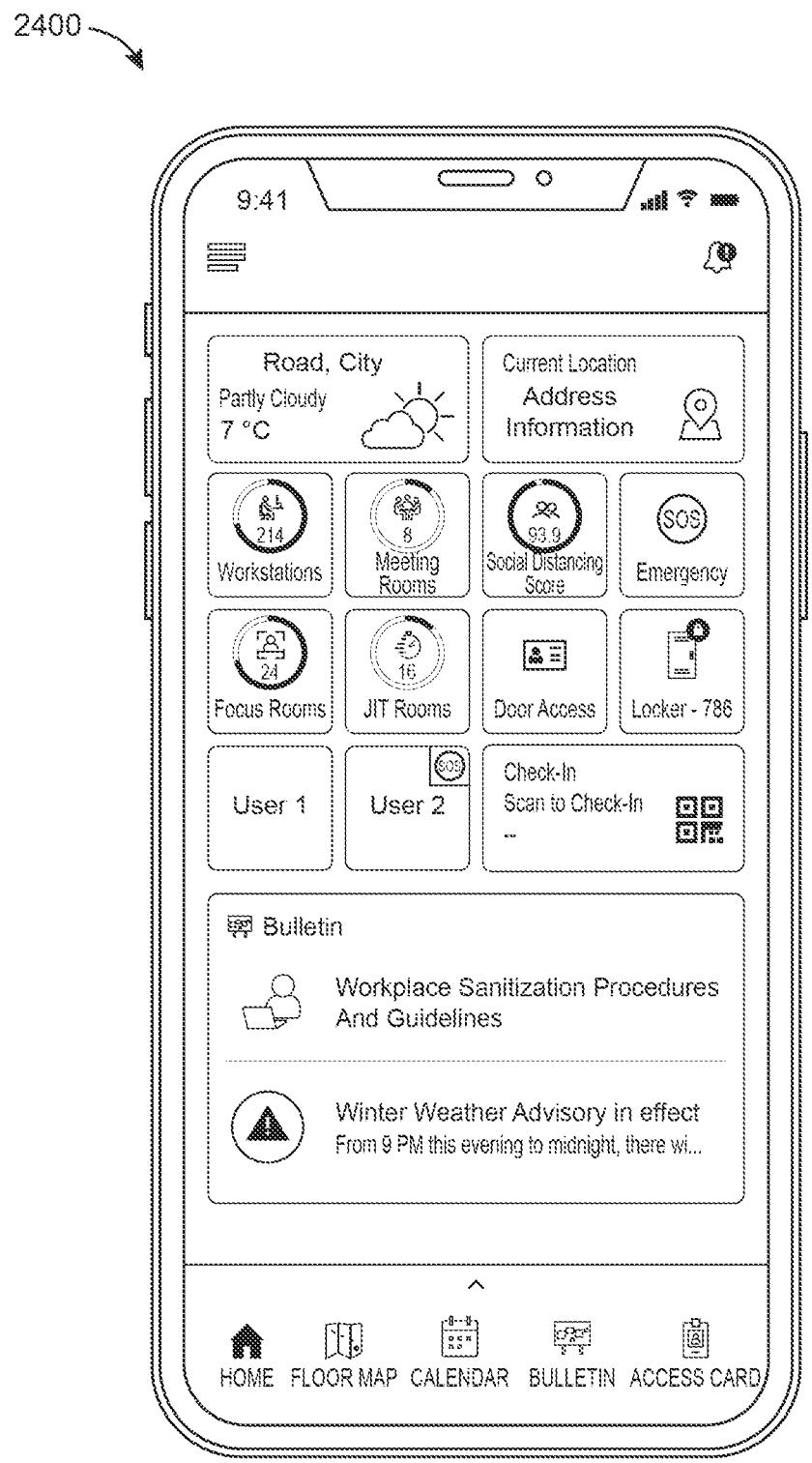
FIG. 24 is a schematic diagram of a home screen of the building disease control system of FIG. 11, according to an exemplary embodiment.

Referring now to FIG. 24, a home screen 2400 of the building disease control system 1104 of FIG. 11, according to an exemplary embodiment. The home screen 2400 can be generated by the user interface manager 1112 and displayed on the user device 1102. The home screen 2400 can be part of a mobile application that provides a seamless experience for building occupants and helps increase occupant productivity. The mobile application can enable frictionless access, help monitor social distancing compliance, help a user find spaces using live map view and navigation, book, check into and release hot desks, book and execute smart meetings, communicate and respond to emergencies, report building issues, manage visitors and parking, adjust comfort, etc.

The mobile application can provide enterprise management insights with respect to building utilization, occupancy, and building predictions. The application can implement services for BMS, access, calendar, collaboration, static location services, location services, space management, lighting, smart desk, occupancy, helpdesk, room panel, catering/butler, audio visual control, smart locker, facial recognition, chat bot, fire and safety, license plate recognition, and/or visitor management.

Figure 25:
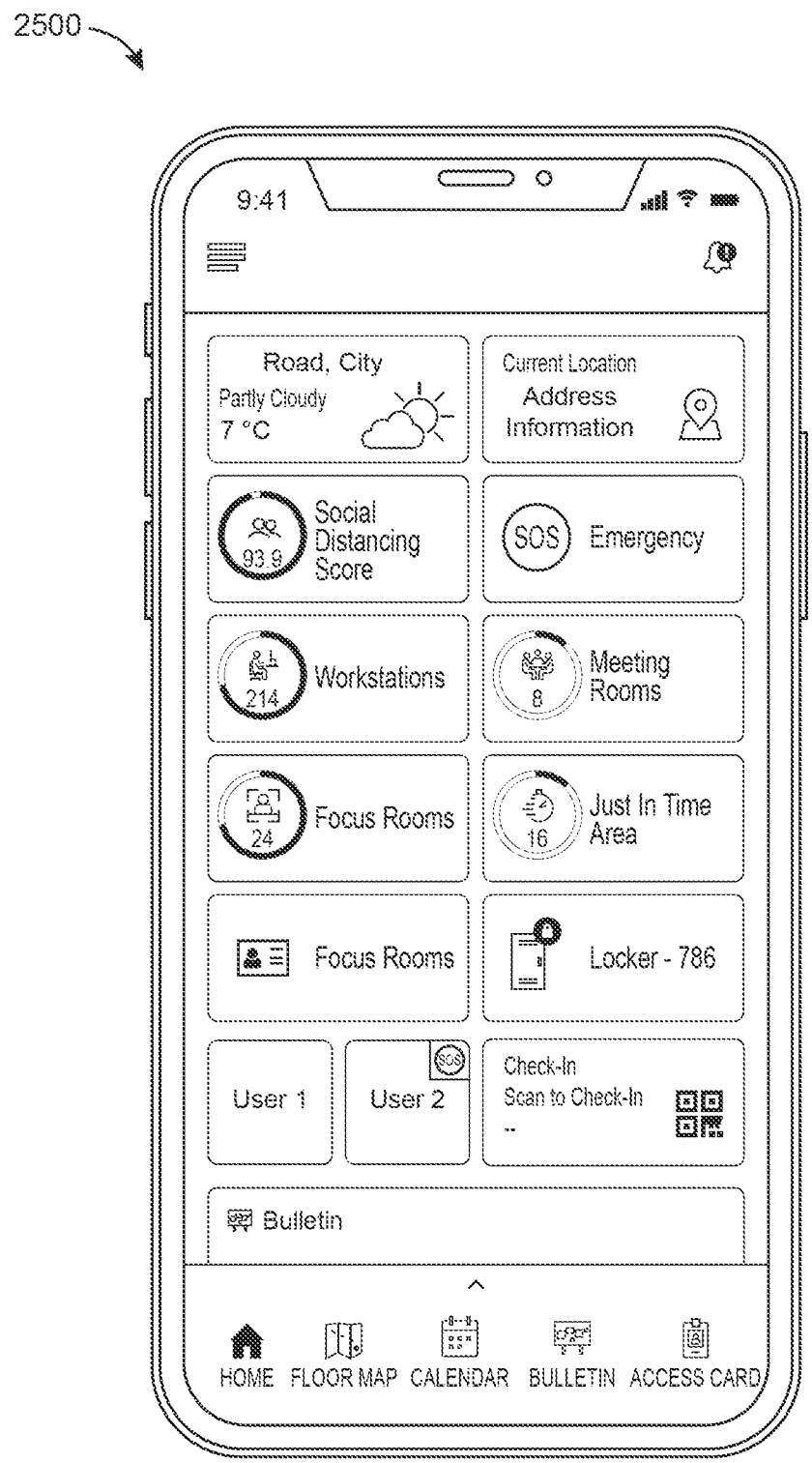
FIG. 25 is a schematic diagram of another home screen of the building disease control system of FIG. 11, according to an exemplary embodiment.

Referring now to FIG. 25, another home screen 2500 of the building disease control system 1104 of FIG. 11, according to an exemplary embodiment. The home screen 2500 is similar to the home screen 2400 of FIG. 24 but includes an alternate layout of tiles. A user can interact with the tiles to view additional information associated with each of the tiles. The home screen 2500 can be generated by the user interface manager 1112 and displayed on the user device 1102.

The home screen 2500 includes an indication of a current location. The indication of the current location informs the user regarding what city, building, and floor the occupant is located in. Furthermore, the home screen 2500 indicates the current weather conditions at the location of the user. The home screen 2500 includes a social distancing score for the user of the user device that the home screen 2500 is displayed on. The social distancing score can be the score generated by the user scoring service 1126 and/or as described with respect to FIG. 14. The home screen 2500 includes an indication of an emergency. Furthermore the home screen 2500 includes tiles for workstations, meeting rooms, focus areas, just in time areas, door access, an indication of a locker, a check in code, and indications of other occupants.

Referring now to FIG. 26, a navigation screen 2600 is shown, according to an exemplary embodiment. The information displayed within the navigation screen 2600 can be generated by the building navigation service 1128. The home screen 2600 can be generated by the user interface manager 1112 and displayed on the user device 1102. The navigation screen 2600 includes an indication of the starting location, the ending location, a level of risk that the user is willing to take, and a map. The map may graphically indicate the starting location, the ending location, and the route for the user to take from the starting location to the ending location. The map can indicate a floor plan of a building that is color coded based on the risk level of various areas of the building.

The building navigation service 1128 can receive an indication of a location of the user device 1102. The building navigation service 1128 can automatically populate the starting location of the navigation screen 2600 with the current location of the user device 1102. In some embodiments, a user may select a starting location via the navigation screen 2600. The user may define a destination location via the navigation screen 2600.

Based on the starting location and the destination location, the building navigation service 1128 can generate a route from the starting location to the destination location. In some embodiments, the route can be generated by the building navigation service 1128 to take more or less risks, e.g., pass through high risk areas of the building or avoid high risk areas of the building. The high risk areas of the building may be areas where there is currently high occupancy, there is historically high occupancy, and/or areas where an infected occupant has been present.

In some embodiments, a user may select via the navigation screen 2600 between generating a shortest route or a safest route. Based on whether the user selects between the shortest route and the safest route, the building navigation service 1128 can generate the appropriate route. If the user selects the shortest route, the building navigation service 1128 can generate a route from the starting location to the destination location that is shortest even if it passes through high risk areas of the building. If the user selects the safest route, the navigation screen 2600 can generate a route that only passes through low risk areas of the building (or passes through a minimum amount of high risk areas). In some embodiments, the user can select a risk level on a scale, e.g., via a slider, via a set of buttons, etc. that indicates a particular level of risk that the use is willing to take. The building navigation service 1128 can generate the route based on the level of risk that the user is willing to take.

In some embodiments, the building navigation service 1128 can store indications about the uses of various areas of a building that are used for a medical purpose. For example, certain areas of a building and/or certain buildings of a campus may be used to house infected individuals, e.g., particular floor of a dormitory building. The building navigation service 1128 could be configured to generate a route from a starting location to a destination location that avoids the areas of the building used for a medical purpose.

Figure 27:
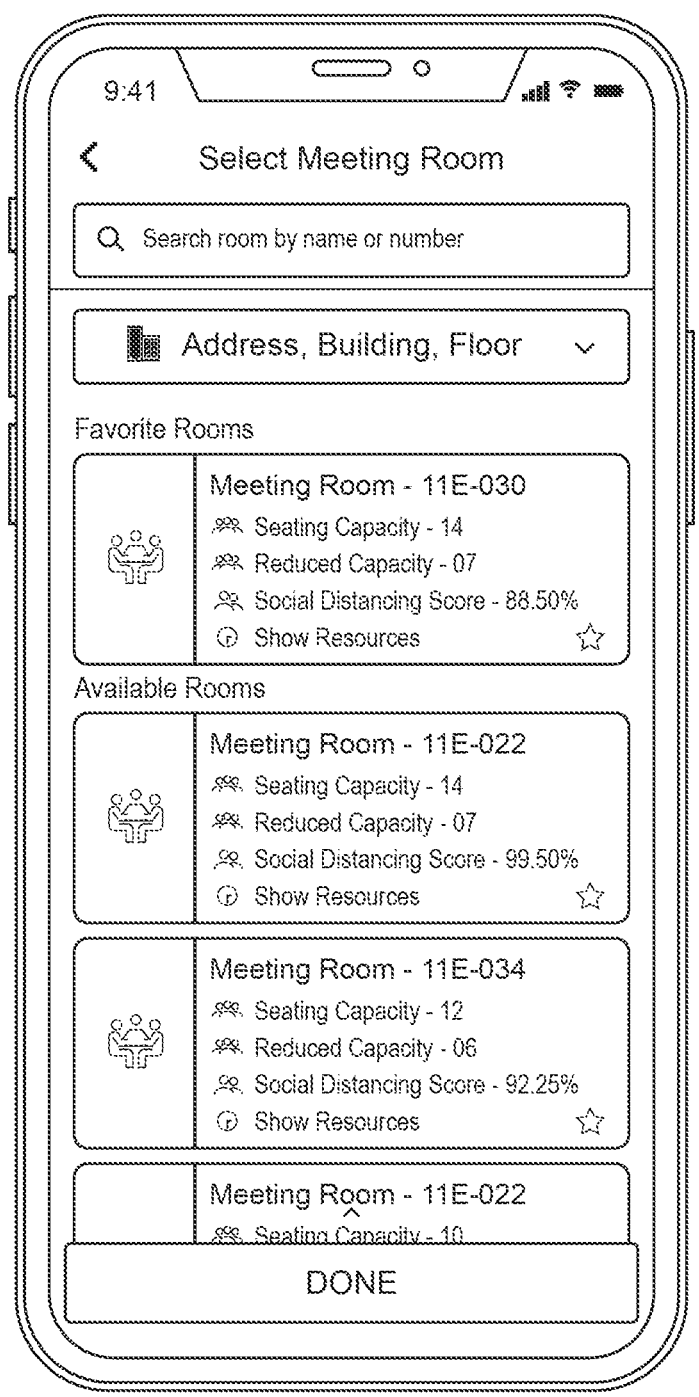
FIG. 27 is a schematic diagram of a scheduling interface of the building disease control system of FIG. 11, according to an exemplary embodiment.

Referring now to FIG. 27 is a scheduling interface 2700 is shown, according to an exemplary embodiment. The scheduling interface 2700 can be generated by the user interface manager 1112 and displayed on the user device 1102. The information generated for display within the scheduling interface 2700 can be configured by the space manager 1118. In the scheduling interface 2700, a user can search for meeting rooms to book a meeting in. The scheduling interface 2700 can sort various rooms based on name or number. The scheduling interface 2700 can provide user with their favorite rooms, rooms that user books often, and a list of all available rooms.

The scheduling interface 2700 can indicate a seating capacity for each meeting room and a reduced capacity for each meeting room. The seating capacity can indicate the maximum capacity for the room while the reduced capacity can indicate the occupancy level that maintains social distancing requirements. Furthermore, the meeting room can include a social distancing score. The social distancing score can indicate how successful previous occupants have been in social distancing, e.g., it can be based on the number of previous social distancing violations that have occurred within the zone. In some embodiments, the social distancing score is determined by the space scoring service 1120. The score can be generated for the space as described in FIG. 14.

Figure 28:
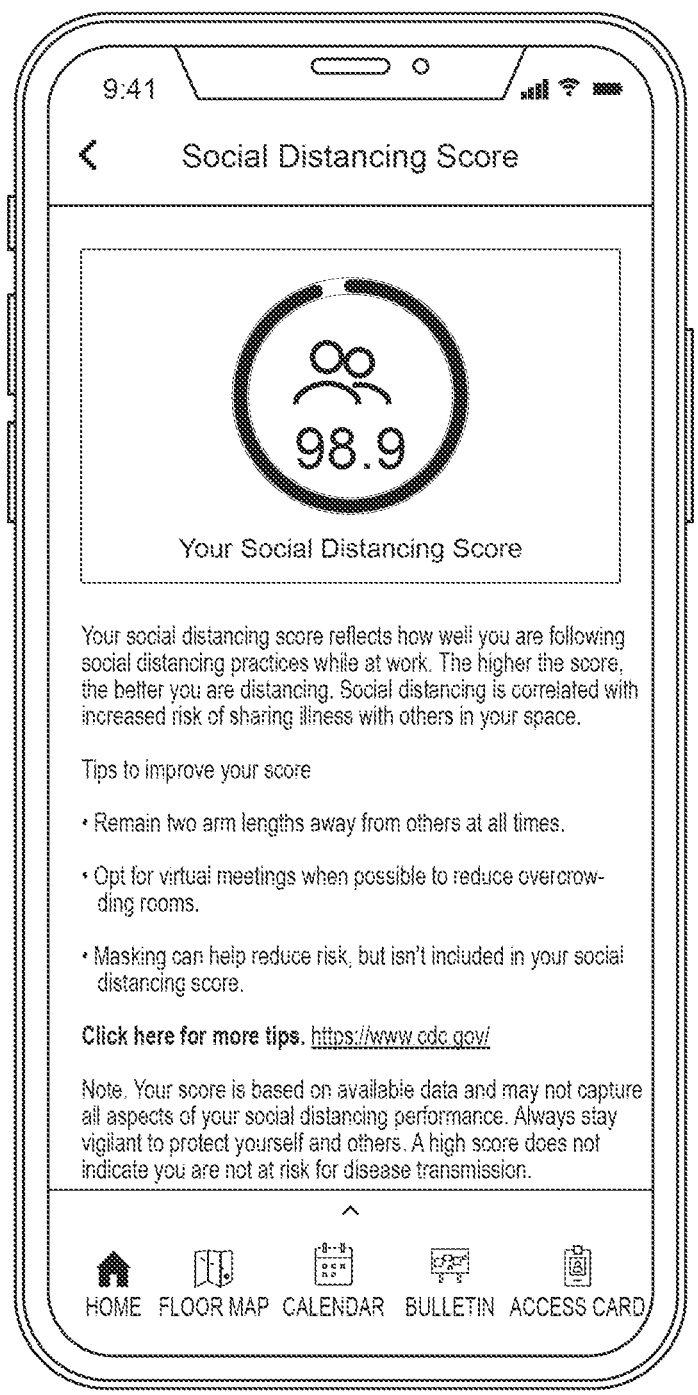
FIG. 28 is a schematic diagram of a social distancing score interface of the building disease control system of FIG.

Referring now to FIG. 28, a schematic diagram of a social distancing score interface 2800 is shown, according to an exemplary embodiment. The interface 2800 can be generated by the user interface manager 1112 and displayed on the user device 1102. The information generated for display within the interface 2800 can be configured by the user scoring service 1126. The interface 2800 can include the score generated by the user scoring service 1126 for a particular user. In this regard, the user scoring service 1126 can generate the user score as described with reference to FIG. 11 and FIGS. 13A-13B and cause a user to see their score by causing the interface 2800 which may be associated with the user to display the score. In some embodiments, the user can view the interface 2800 after interacting with the tile including the user score as shown in the home screens of FIGS. 24 and 25.

Referring now to FIGS. 29-31, user interfaces 2900-3100 illustrating key performance indicators for a building HVAC system, the performance of a chiller, and faults associated with a chiller are shown, according to an exemplary embodiment. The user interfaces 2900-3100 can be HVAC based interfaces. The interfaces 2900-3100 can be integrated within an application that also provides the disease control related interfaces, e.g., the interfaces and operations described with reference to FIGS. 11-28. The disease control related interfaces can be integrated in an application along with energy management, asset performance, financials and utility bill management, work order management, space performance analytics, global alarm management, wellness, tenant management and billing, digital signage, reporting, etc.

CONFIGURATION OF EXEMPLARY EMBODIMENTS

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

What is claimed is:

1. A building system of a building, the building system comprising one or more memory devices configured to store instructions thereon that, when executed by one or more processors, cause the one or more processors to:
   receive occupancy data of a plurality of occupants from an occupant tracking system, the occupancy data indicating locations of the plurality of occupants within a building space of the building;
   determine, based on the occupancy data, whether one or more occupants of the plurality of occupants have violated a social distancing policy that reduces a spread of an infectious disease within the building based on the locations of at least two of the plurality of occupants, the social distancing policy based on one or more characteristics of the building space; and
   perform one or more operations to improve compliance with the social distancing policy within the building in response to a determination that the one or more occupants have violated the social distancing policy by:
   adding a social distancing alert to a list of active alerts in the building; and
   providing the list of active alerts to a system.

2. The building system of claim 1, wherein the one or more operations include:
   generating a notification that includes an indication of the social distancing policy being violated; and
   sending the notification to user devices associated with the one or more occupants.

3. The building system of claim 1, wherein the one or more occupants include a first occupant and a second occupant;
   wherein the instructions cause the one or more processors to:
      record an encounter between the first occupant and the second occupant with a plurality of encounters between occupants of the plurality of occupants;
      receive an indication of one or more infected occupants of the plurality of occupants that are infected with the infectious disease; and
      analyze the plurality of encounters to identify one or more potentially infected occupants that have come into contact with the one or more infected occupants.

4. The building system of claim 1, wherein the instructions cause the one or more processors to:
   generate a space score for one space of a plurality of spaces of the building based on one or more parameters, the one or more parameters indicating a number of social distancing violations that have occurred within the one space; and
   cause a user device to display the space score for the one space.

5. The building system of claim 1, wherein providing the list of active alerts to a system comprises causing a building monitoring interface to display the list of active social distancing alerts.

6. The building system of claim 1, wherein the one or more occupants include a first occupant and a second occupant;
   wherein the instructions cause the one or more processors to:
      record a social distancing violation between the first occupant and the second occupant with a plurality of social distancing violations between the plurality of occupants;
      generate one or more trends that trend a plurality of social distancing violations over time; and
      cause a user interface to display the one or more trends.

7. The building system of claim 1, wherein the instructions cause the one or more processors to:
   determine a number of occupants in each space of a plurality of spaces of the building based on the occupancy data;
   determine whether the number of occupants in each space of the plurality of spaces is greater than or less than one or more levels, wherein the one or more levels indicate underutilization of a space, normal utilization of a space, or over utilization of a space based on a size of each space of the plurality of spaces; and
   generate a building layout interface that indicates the plurality of spaces and whether each space is underutilized, over utilized, or is normally utilization.

8. The building system of claim 1, wherein the one or more occupants include a first occupant and a second occupant;
   wherein the instructions cause the one or more processors to:
      record a social distancing violation between the first occupant and the second occupant with a plurality of social distancing violations between the plurality of occupants;

generate a first graphic element indicating proportions of time that an occupant of the plurality of occupants has spent in a plurality of locations of the building;

generate a second graphic element indicating proportions of social distancing violations between the occupant and each the plurality of occupants;

generate one or more third graphic elements that each indicate a proportion of social distancing violations between the occupant and each of the plurality of occupants at one location of the plurality of locations of the building; and generate a user interface including the first graphic element, the second graphic element, and the one or more third graphic elements.

9. The building system of claim 1, wherein the one or more occupants include a first occupant and a second occupant;

wherein the instructions cause the one or more processors to:

generate a table based on social distancing violations and the occupancy data, the table including a plurality of rows and a plurality of columns, wherein the plurality of rows each indicate an occupant of the plurality of occupants and the plurality of columns include:

a first column indicating a total time that each of the plurality of occupants have spent within the building;

a second column indicating a total amount of time that each of the plurality of occupants have spent engaging in the social distancing violations within the building;

a third column indicating a ratio between the total time that each of the plurality of occupants have spent within the building and the total amount of time that each of the plurality of occupants have spent engaging in the social distancing violations within the building;

a fourth column including an indication of a number of users that each user has performed a social distancing violation with; and a fifth column indicating a number of spaces that each user has performed a social distancing violation within.

10. The building system of claim 1, wherein the instructions cause the one or more processors to:

receive an indication of infection risk levels associated with a plurality of areas of the building; receive a starting location of a user within the building and a destination location within the building from a user device;

receive a risk tolerance level from the user device;

generate, based on the infection risk levels associated with the plurality of areas of the building, a route through the building from the starting location to the destination location that avoids one or more high risk areas of the building or passes through the one or more high risk areas of the building based on the risk tolerance level; and cause a user interface to display the route through the building.

11. The building system of claim 1, wherein the instructions cause the one or more processors to:

determine occupancy levels in each space of a plurality of spaces of the building over a historical time period based on the occupancy data; and generate a heat map that that indicates historical utilization of each space of the plurality of spaces over the historical time period.

12. The building system of claim 11, wherein the instructions cause the one or more processors to schedule building sanitization for the plurality of spaces of the building based on the heat map.

13. The building system of claim 1, wherein the instructions cause the one or more processors to:

generate a user score for one occupant of the plurality of occupants based on one or more parameters, the one or more parameters indicating a number of social distancing violations associated with the one occupant; and cause a user device to display the user score for the one occupant.

14. The building system of claim 13, wherein the one or more parameters include at least one of:

a roster adherence parameter indicating whether the one occupant has followed a roster schedule;

social distancing violations parameter indicating the number of social distancing violations associated with the one occupant;

a training awareness parameter indicating social distancing training that the one occupant has completed;

health parameters indicating health characteristics of the one occupant;

a supplies requisition parameter indicating health supplies that the one occupant has acquired;

a lone worker duress parameter indicating whether the one occupant has triggered a lone worker response request; or an infection level parameter indicating infection levels in a geographic area associated with a residence of the one occupant.

15. The building system of claim 1, wherein the building system further comprises:

the occupant tracking system, wherein the occupant tracking system comprises:

a plurality of transceivers each located within a space of the building, wherein the plurality of transceivers are configured to communicate with a plurality of badges to detect what space of the building the plurality of badges are located within; and the plurality of badges, wherein each badge of the plurality of badges is carried by one occupant of the plurality of occupants and includes an identifier linked to the one occupant.

16. The building system of claim 15, wherein a first badge of the plurality of badges is configured to:

wirelessly send a first identifier of the first badge to a second badge of the plurality of badges in response to the first badge being within a particular distance from the second badge;

wirelessly receive a second identifier of the second badge from the second badge in response to the first badge being within the particular distance from the second badge;

store a contact event in a memory device of the first badge, the contact event including the first identifier and the second identifier; and wirelessly communicate the contact event to a transceiver of the plurality of transceivers in response to the first badge being within another particular distance from the transceiver.

17. The building system of claim 15, wherein the plurality of transceivers include a transceiver that is mounted on a power outlet and is plugged into the power outlet, wherein the plurality of transceivers communicate with the plurality of badges via a first wireless communication protocol and communicate with the one or more processors via a second wireless communication protocol;

wherein the plurality of badges include a battery and a wireless radio, wherein the battery is configured to power the wireless radio.

18. A method comprising:
receiving, by a processing circuit, occupancy data of a plurality of occupants from an occupant tracking system, the occupancy data indicating locations of the plurality of occupants within a building space of a building;
determining, by the processing circuit, based on the occupancy data, whether one or more occupants of the plurality of occupants have violated a social distancing policy that reduces a spread of an infectious disease within the building based on the locations of at least two of the plurality of occupants, the social distancing policy based on one or more characteristics of the building space;
performing, by the processing circuit, one or more operations to improve compliance with the social distancing policy within the building in response to a determination that the one or more occupants have violated the social distancing policy;
determining, by the processing circuit, a number of occupants in a first space of a plurality of spaces of the building based on the occupancy data;
determining, by the processing circuit, whether the number of occupants in the first space of the plurality of spaces is greater than or less than one or more levels, wherein the one or more levels indicate underutilization of a space, normal utilization of a space, or over utilization of a space based on a size of the first space of the plurality of spaces; and
generating, by the processing circuit, a building layout interface that indicates the plurality of spaces and whether the first space is underutilized, over utilized, or is normally utilization.

19. The method of claim 18, further comprising:
generating, by the processing circuit, a space score for one space of a plurality of spaces of the building based on one or more parameters, the one or more parameters indicating a number of social distancing violations that have occurred within the one space; and
causing, by the processing circuit, a user device to display the space score for the one space.

20. The method of claim 18, wherein performing, by the processing circuit, the one or more operations to improve compliance with the social distancing policy comprising:
adding a social distancing alert to a list of active social distancing alerts in the building; and
causing a building monitoring interface to display the list of active social distancing alerts.

21. The method of claim 18, wherein the one or more occupants include a first occupant and a second occupant; wherein the method further comprises:
generating one or more trends that trend a plurality of social distancing violations over time; and
causing a user interface to include the one or more trends.

22. The method of claim 18, wherein the one or more occupants include a first occupant and a second occupant; wherein the method further comprises:
recording, by the processing circuit, a social distancing violation between the first occupant and the second occupant with a plurality of social distancing violations between the plurality of occupants;
generating, by the processing circuit, a first graphic element indicating proportions of time that an occupant of the plurality of occupants has spent in a plurality of locations of the building;
generating, by the processing circuit, a second graphic element indicating proportions of social distancing violations between the occupant and each the plurality of occupants;
generating, by the processing circuit, one or more third graphic elements that each indicate a proportion of social distancing violations between the occupant and each of the plurality of occupants at one location of the plurality of locations of the building; and
generating, by the processing circuit, a user interface including the first graphic element, the second graphic element, and the one or more third graphic elements.

23. One or more memory devices configured to store instructions thereon that, when executed by one or more processors, cause the one or more processors to:
receive occupancy data of a plurality of occupants from an occupant tracking system, the occupancy data indicating locations of the plurality of occupants within a building space of a building;
determine, based on the occupancy data, whether one or more occupants of the plurality of occupants have violated a social distancing policy that reduces a spread of an infectious disease within the building based on the locations of at least two of the plurality of occupants, the social distancing policy based on one or more characteristics of the building space;
perform one or more operations to improve compliance with the social distancing policy within the building in response to a determination that the one or more occupants have violated the social distancing policy;
determine occupancy levels in a plurality of spaces of the building over a historical time period based on the occupancy data; and
schedule building sanitization for the plurality of spaces of the building based on the occupancy levels.

24. The one or more memory devices of claim 23, wherein the instructions cause the one or more processors to perform the one or more operations to improve compliance with the social distancing policy by:
adding a social distancing alert to a list of active social distancing alerts in the building; and
causing a building monitoring interface to display the list of active social distancing alerts.

* * * * *